(12) United States Patent
Candito et al.

(10) Patent No.: US 11,161,854 B2
(45) Date of Patent: Nov. 2, 2021

(54) INDAZOLYL-SPIRO[2.2]PENTANE-CARBONITRILE DERIVATIVES AS LRRK2 INHIBITORS, PHARMACEUTICAL COMPOSITIONS, AND USES THEREOF

(71) Applicants: Merck Sharp & Dohme Corp., Rahway, NJ (US); David Annunziato Candito, Wrentham, MA (US); Thomas H. Graham, Somerville, MA (US); John Acton, Cranford, NJ (US); Ryan Wing-Kun Chau, Somerville, MA (US); Joanna L. Chen, Braintree, MA (US); J. Michael Ellis, Needham, MA (US); Peter H. Fuller, Ashland, MA (US); Anmol Gulati, Watertown, MA (US); Hakan Gunaydin, Somerville, MA (US); Solomon Kattar, Wakefield, MA (US); Mitchell Henry Keylor, Malden, MA (US); Blair T. Lapointe, Sudbury, MA (US); Ping Liu, Westfield, NJ (US); Weiguo Liu, Princeton, NJ (US); Joey L. Methot, Westwood, MA (US); Santhosh F. Neelamkavil, Edison, NJ (US); Vladimir Simov, South Boston, MA (US); Ling Tong, Warren, NJ (US); Harold B. Wood, Westfield, NJ (US)

(72) Inventors: David Annunziato Candito, Wrentham, MA (US); Thomas H. Graham, Somerville, MA (US); John Acton, Cranford, NJ (US); Ryan Wing-Kun Chau, Somerville, MA (US); Joanna L. Chen, Braintree, MA (US); J. Michael Ellis, Needham, MA (US); Peter H. Fuller, Ashland, MA (US); Anmol Gulati, Watertown, MA (US); Hakan Gunaydin, Somerville, MA (US); Solomon Kattar, Wakefield, MA (US); Mitchell Henry Keylor, Malden, MA (US); Blair T. Lapointe, Sudbury, MA (US); Ping Liu, Westfield, NJ (US); Weiguo Liu, Princeton, NJ (US); Joey L. Methot, Westwood, MA (US); Santhosh F. Neelamkavil, Edison, NJ (US); Vladimir Simov, South Boston, MA (US); Ling Tong, Warren, NJ (US); Harold B. Wood, Westfield, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 27 days.

(21) Appl. No.: 16/755,172

(22) PCT Filed: Oct. 8, 2018

(86) PCT No.: PCT/US2018/054789
§ 371 (c)(1),
(2) Date: Apr. 10, 2020

(87) PCT Pub. No.: WO2019/074809
PCT Pub. Date: Apr. 18, 2019

(65) Prior Publication Data
US 2021/0188863 A1    Jun. 24, 2021

Related U.S. Application Data

(60) Provisional application No. 62/570,791, filed on Oct. 11, 2017.

(51) Int. Cl.
*C07D 491/10* (2006.01)
*C07D 401/14* (2006.01)
(Continued)

(52) U.S. Cl.
CPC ......... *C07D 491/10* (2013.01); *C07D 401/14* (2013.01); *C07D 403/04* (2013.01);
(Continued)

(58) Field of Classification Search
CPC .. C07D 491/10; C07D 401/14; C07D 403/04; C07D 403/14
See application file for complete search history.

(56) References Cited

U.S. PATENT DOCUMENTS

2016/0326151 A1    11/2016    Gummadi

FOREIGN PATENT DOCUMENTS

| WO | 2008040753 A1 | 4/2008 |
| WO | 2016036586 A1 | 3/2016 |

OTHER PUBLICATIONS

International Search Report PCT/US2018/54790—dated Jan. 22, 2019, 12 pages.
(Continued)

Primary Examiner — Rebecca L Anderson
(74) Attorney, Agent, or Firm — Sylvia A. Ayler; Catherine D. Fitch

(57) ABSTRACT

The present invention is directed to substituted certain reversed indazolyl-spiro[2.2]pentane-carbonitrile derivatives of Formula (I): and pharmaceutically acceptable salts thereof, wherein R1, R2, R3, X, Y, and Z are as defined herein, which are potent inhibitors of LRRK2 kinase and may be useful in the treatment or prevention of diseases in which the LRRK2 kinase is involved, such as Parkinson's Disease and other diseases and disorders described herein. The invention is also directed to pharmaceutical compositions comprising these compounds and the use of these compounds and compositions in the prevention or treatment of such diseases in which LRRK-2 kinase is involved.

(Continued)

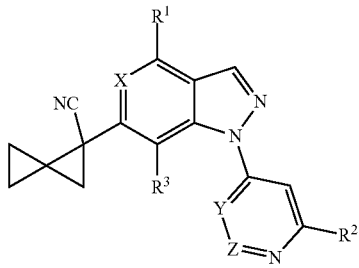

(I)

10 Claims, No Drawings

(51) Int. Cl.
C07D 403/04 (2006.01)
C07D 403/14 (2006.01)
C07D 405/14 (2006.01)
C07D 413/14 (2006.01)
C07D 487/08 (2006.01)
C07D 498/04 (2006.01)
C07D 498/10 (2006.01)
C07D 519/00 (2006.01)

(52) U.S. Cl.
CPC ......... *C07D 403/14* (2013.01); *C07D 405/14* (2013.01); *C07D 413/14* (2013.01); *C07D 487/08* (2013.01); *C07D 498/04* (2013.01); *C07D 498/10* (2013.01); *C07D 519/00* (2013.01)

(56) References Cited

OTHER PUBLICATIONS

Galatsis, Paul, Leucine-rich repeat kinase 2 inhibitors: a patent review (2014-2016), Expert Opinion on Therapeutic Patents, 2017, 667-676, 27(6).

INDAZOLYL-SPIRO[2.2]PENTANE-CARBONITRILE DERIVATIVES AS LRRK2 INHIBITORS, PHARMACEUTICAL COMPOSITIONS, AND USES THEREOF

BACKGROUND OF THE INVENTION

Parkinson's disease (PD) is a common neurodegenerative disease caused by progressive loss of mid-brain dopaminergic neurons leading to abnormal motor symptoms such as bradykinesia, rigidity and resting tremor. Many PD patients also experience a variety of non-motor symptoms including cognitive dysfunction, autonomic dysfunction, emotional changes and sleep disruption. The combined motor and non-motor symptoms of Parkinson's disease severely impact patient quality of life.

While the majority of PD cases are idiopathic, there are several genetic determinants such as mutations in SNCA, Parkin, PINK1, DJ-1 and LRRK2. Linkage analysis studies have demonstrated that multiple missense mutations in the Leucine-Rich Repeat Kinase 2 (LRRK2) gene lead to an autosomal late onset form of PD. LRRK2 is a 286 kDa cytoplasmic protein containing kinase and GTPase domains as well as multiple protein-protein interaction domains. See for example, Aasly et al., Annals of Neurology, Vol. 57(5), May 2005, pp. 762-765; Adams et al., Brain, Vol. 128, 2005, pp. 2777-85; Gilks et al., Lancet, Vol. 365, Jan. 29, 2005, pp. 415-416, Nichols et al., Lancet, Vol. 365, Jan. 29, 2005, pp. 410-412, and U. Kumari and E. Tan, FEBS journal 276 (2009) pp. 6455-6463.

In vitro biochemical studies have demonstrated that LRRK2 proteins harboring the PD associated proteins generally confer increased kinase activity and decreased GTP hydrolysis compared to the wild type protein (Guo et al., Experimental Cell Research, Vol, 313, 2007, pp. 3658-3670) thereby suggesting that small molecule LRRK2 kinase inhibitors may be able to block aberrant LRRK2-dependent signaling in PD. In support of this notion, it has been reported that inhibitors of LRRK2 are protective in models of PD (Lee et al., Nature Medicine, Vol 16, 2010, pp. 998-1000).

LRRK2 expression is highest in the same brain regions that are affected by PD. LRRK2 is found in Lewy bodies, a pathological hallmark of PD as well as other neurodegenerative diseases such as Lewy body dementia (Zhu et al., Molecular Neurodegeneration, Vol 30, 2006, pp. 1-17). Further, LRRK2 mRNA levels are increased in the striatum of MPTP-treated marmosets, an experimental model of Parkinson's disease, and the level of increased mRNA correlates with the level of L-Dopa induced dyskinesia suggesting that inhibition of LRRK2 kinase activity may have utility in ameliorating L-Dopa induced dyskinesias. These and other recent studies indicate that a potent, selective and brain penetrant LRRK2 kinase inhibitor could be a therapeutic treatment for PD. (Lee et al., Nat. Med. 2010 September; 16(9):998-1000; Zhu, et al., Mol. Neurodegeneration 2006 Nov. 30; 1:17; Daher, et al., J Biol Chem. 2015 Aug. 7; 290(32):19433-44; Volpicelli-Daley et al., J Neurosci. 2016 Jul. 13; 36(28):7415-27).

LRRK2 mutations have been associated with Alzheimer's-like pathology (Zimprach et al., Neuron. 2004 Nov. 18; 44(4):601-7) and the LRRK2 R1628P variant has been associated with an increased risk of developing AD (Zhao et al., Neurobiol Aging. 2011 November; 32(11):1990-3). Mutations in LRRK2 have also been identified that are clinically associated with the transition from mild cognitive impairment to Alzheimer's disease (see WO2007149798). Together these data suggest that LRRK2 inhibitors may be useful in the treatment of Alzheimer's disease and other dementias and related neurodegenerative disorders.

LRRK2 has been reported to phosphorylate tubulin-associated tau and this phosphorylation is enhanced by the kinase activating LRRK2 mutation G2019S (Kawakami et al., PLoS One. 2012; 7(1):e30834; Bailey et al., Acta Neuropathol. 2013 December; 126(6):809-27). Additionally, over expression of LRRK2 in a tau transgenic mouse model resulted in the aggregation of insoluble tau and its phosphorylation at multiple epitopes (Bailey et al., 2013). Hyperphosphorylation of tau has also been observed in LRRK2 R1441G overexpressing transgenic mice (Li et al., Nat Neurosci. 2009 July; 12(7):826-8). Inhibition of LRRK2 kinase activity may therefore be useful in the treatment of tauopathy disorders characterized by hyperphosphorylated of tau such as argyrophilic grain disease, Picks disease, corticobasal degeneration, progressive supranuclear palsy, inherited frontotemporal dementia and parkinson's linked to chromosome 17 (Goedert and Jakes Biochim Biophys Acta. 2005 Jan. 3).

A growing body of evidence suggests a role for LRRK2 in immune cell function in the brain with LRRK2 inhibitors demonstrated to attenuate microglial inflammatory responses (Moehle et al., J Neurosci. 2012 Feb. 1; 32(5): 1602-11). As neuroinflammation is a hallmark of a number of neurodegenerative diseases such PD, AD, MS, HIV-induced dementia, ALS, ischemic stroke, MS, traumatic brain injury and spinal cord injury, LRRK2 kinases inhibitors may have utility in the treatment of neuroinflammation in these disorders. Significantly elevated levels of LRRK2 mRNA have been observed in muscle biopsy samples taken from patients with ALS (Shtilbans et al., Amyotroph Lateral Scler. 2011 July; 12(4):250-6).

LRRK2 is also expressed in cells of the immune system and recent reports suggest that LRRK2 may play a role in the regulation of the immune system and modulation of inflammatory responses. LRRK2 kinase inhibitors may therefore be of utility in a number of diseases of the immune system such as lymphomas, leukemias, multiple sclerosis rheumatoid arthritis, systemic lupus erythematosus autoimmune hemolytic anemia, pure red cell aplasia, idiopathic thrombocytopenic pupura (ITP), Evans Syndrome, vasculitis, bullous skin disorder, type I diabetes mellitus, Sjorgen's syndrome, Delvic's disease, inflammatory myopathies (Engel at al., Pharmacol Rev. 2011 March; 63(1):127-56; Homam et al., Homam et al., Clin Neuromuscluar disease, 2010) and ankylosing spondylitis (Danoy et al., PLoS Genet. 2010 Dec. 2; 6(12)). Increased incidence of certain types of non-skin cancers such as renal, breast, lung, prostate, and acute myelogenous leukemia (AML) have been reported in patients with the LRRK2 G2019S mutation (Agalliu et al., JAMA Neurol. 2015 January; 72(1); Saunders-Pullman et al., Mov Disord. 2010 Nov. 15; 25(15):2536-41). LRRK2 has amplification and overexpression has been reported in papillary renal and thyroid carcinomas. Inhibiting LRRK2 kinase activity may therefore be useful in the treatment of cancer (Looyenga et al., Proc Natl Acad Sci USA. 2011 Jan. 25; 108(4):1439-44).

Genome-wide association studies also highlight LRRK2 in the modification of susceptibility to the chronic autoimmune Crohn's disease and leprosy (Zhang et al., The New England Jopuranl of Medicine, Vol 361, 2009, pp. 2609-2618; Umeno et al., Inflammatory Bowel Disease Vol 17, 2011, pp. 2407-2415).

SUMMARY OF THE INVENTION

The present invention is directed to certain indazolyl-spiro[2.2]pentane-carbonitrile derivatives, which are collectively or individually referred to herein as "compound(s) of the invention" or "compounds of Formula (I)", as described herein. LRRK2 inhibitors have been disclosed in the art, e.g., WO2016036586. Applicant has found, surprisingly and advantageously, that the compounds of Formula (I), each of which possess a spiro[2.2]pentanyl carbonitrile moiety, exhibit excellent LRRK2 inhibitory activity. In some embodiments, the compounds of the invention exhibit unexpectedly superior potency as inhibitors of LRRK2 kinase, as evidenced by the data reported herein. The compounds of the invention may be useful in the treatment or prevention of diseases (or one or more symptoms associated with such diseases) in which the LRRK2 kinase is involved, including Parkinson's disease and other indications, diseases and disorders as described herein. The invention is also directed to pharmaceutical compositions comprising a compound of the invention and to methods for the use of such compounds and compositions for the treatments described herein.

DETAILED DESCRIPTION OF THE INVENTION

For each of the following embodiments, any variable not explicitly defined in the embodiment is as defined in Formula (I) or (IA). In each of the embodiments described herein, each variable is selected independently of the other unless otherwise noted.

In one embodiment, the compounds of the invention have the structural Formula (I):

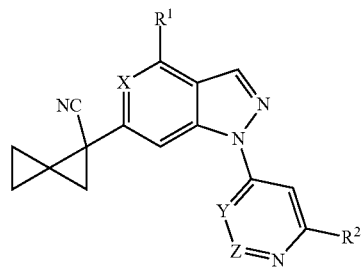

(I)

or a pharmaceutically acceptable salt thereof, wherein:
$R^1$ is H or F;
X is $C(R^X)$ or N;
$R^X$ is H, F, Cl, or —$(C_1$-$C_6)$alkyl;
=Y—Z= is =N—$C(R^Z)$=, =C(H)—$C(R^Z)$=, or =C(H)—N=;
$R^Z$ is H, F, —$(C_1$-$C_6)$alkyl, —$NH_2$, —$NH(C_1$-$C_6)$alkyl, —$N((C_1$-$C_6)$alkyl$)_2$, —$O(C_1$-$C_6)$alkyl, —$S(C_1$-$C_6)$alkyl, —$(C_1$-$C_6)$alkyl-OH, —$(C_1$-$C_6)$alkyl-O—$(C_1$-$C_6)$alkyl,

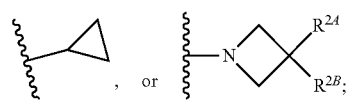

$R^2$ is —$(C_1$-$C_6)$alkyl, —$(C_1$-$C_6)$alkyl-OH,

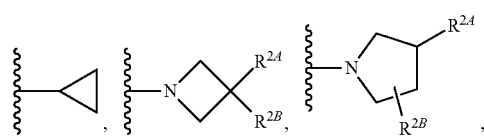

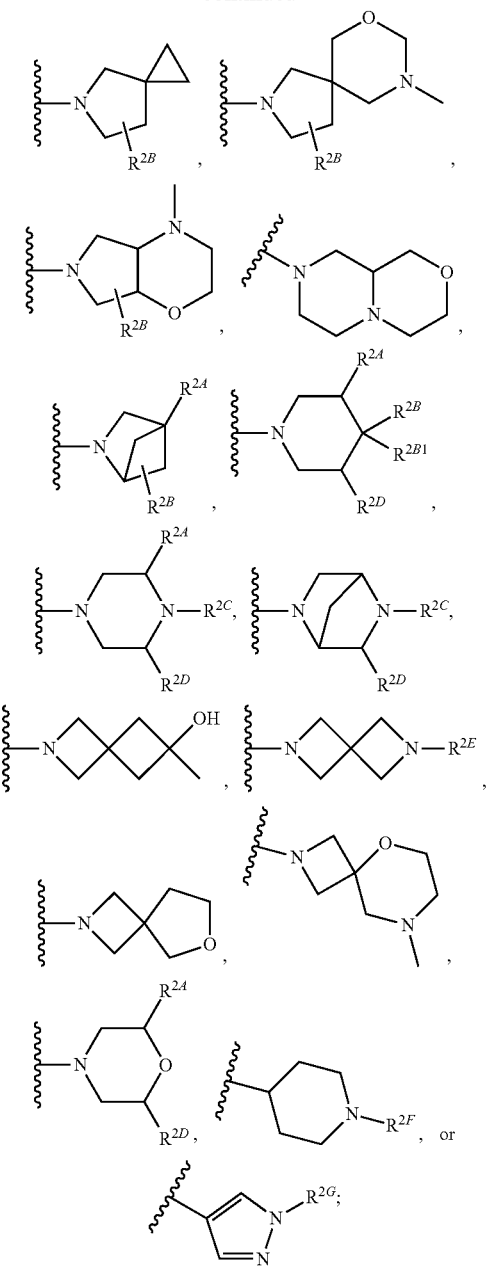

wherein:
$R^{2A}$ is H, F, —OH, —$(C_1$-$C_6)$alkyl, —$(C_1$-$C_6)$haloalkyl, —O—$(C_1$-$C_6)$alkyl, —$C(OH)((C_1$-$C_6)$alkyl$)_2$, —$(C_1$-$C_6)$alkyl-OH, —$(C_1$-$C_6)$alkyl-O—$(C_1$-$C_6)$alkyl, —$C((C_1$-$C_6)$alkyl$)_2$(OH), cyclopropyl, or

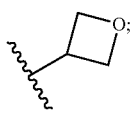 [SMILES: *C1COC1]

$R^{2B}$ is H, F, —OH, —$(C_1$-$C_6)$alkyl, —$C((C_1$-$C_6)$alkyl$)_2$(OH), —$(C_1$-$C_6)$alkyl-OH, —$(C_1$-$C_6)$alkyl-O—$(C_1$-$C_6)$alkyl, or

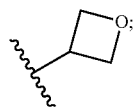

$R^{2B1}$ is H, F, or —($C_1$-$C_6$)alkyl;
$R^{2C}$ is H, —($C_1$-$C_6$)alkyl, —$SO_2$—($C_1$-$C_6$)alkyl,

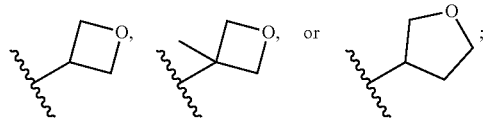

$R^{2D}$ is H, —($C_1$-$C_6$)alkyl, —($C_1$-$C_6$)alkyl-OH, or —($C_1$-$C_6$)alkyl-O—($C_1$-$C_6$)alkyl; and
$R^{2E}$ is H, —($C_1$-$C_6$)alkyl, —($C_1$-$C_6$)haloalkyl,

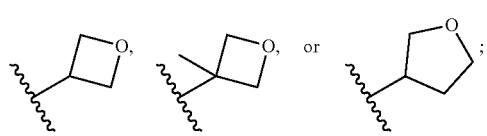

$R^{2F}$ is H, —($C_1$-$C_6$)alkyl, —($C_1$-$C_6$)fluoroalkyl, —($C_1$-$C_6$)alkyl-O—($C_1$-$C_6$)alkyl,

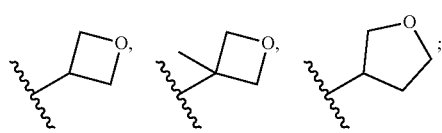

and
$R^{2G}$ is H, —($C_1$-$C_6$)alkyl, or —($C_1$-$C_6$)haloalkyl.

In one embodiment, the compounds of the invention have the structural Formula (I.1):

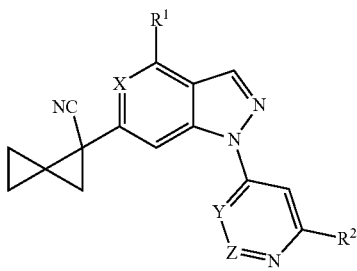

(I.1)

or a pharmaceutically acceptable salt thereof, wherein:
$R^1$ is H or F;
X is C($R^X$) or N;
$R^X$ is H, F, Cl, or $CH_3$;
=Y—Z= is =N—C($R^Z$)=, =C(H)—C($R^Z$)=, or =C(H)—N=;
$R^Z$ is H, —$CH_3$, —$NHCH_3$, —O—$CH_3$, —S—$CH_3$, —$CH_2O$—$CH_3$, or $R^2$ is

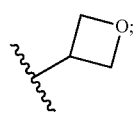

wherein:
$R^{2A}$ is H, F, —OH, —$CH_3$, —$OCH_3$, —C(OH)($CH_3$)$_2$, —$CH_2OH$, —$CH_2O$—$CH_3$, —C($CH_3$)$_2$(OH), cyclopropyl, or

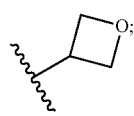

$R^{2B}$ is H, F, —OH, —$CH_3$, —C(OH)($CH_3$)$_2$, —$CH_2OH$—$CH_2O$—$CH_3$, or

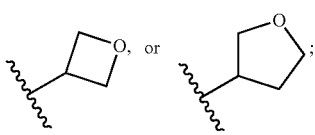 [SMILES: *C1COC1 ; *C1CCOC1]

$R^{2B1}$ is H, F, or $CH_3$;
$R^{2C}$ is H, —$CH_3$, —$SO_2CH_3$, and $R^{2D}$ is H, $CH_3$, —$CH_2OH$, or —$CH_2OCH_3$.

In another embodiment, the compounds of the invention have the structural Formula (I):

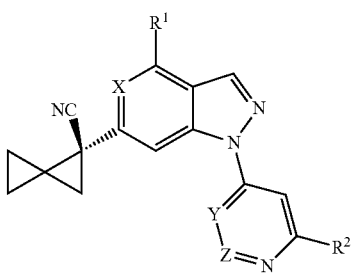

(I')

or a pharmaceutically acceptable salt thereof, wherein $R^1$, $R^2$, X, Y, and Z are as defined in Formula (I) or as in Formula (I.1).

In another embodiment, the compounds of the invention have the structural Formula (I"):

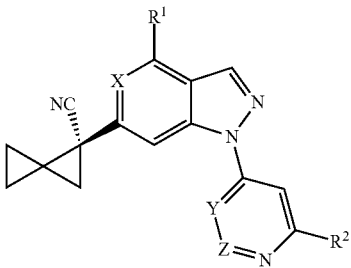

(I")

or a pharmaceutically acceptable salt thereof, wherein $R^1$, $R^2$, X, Y, and Z are as defined in Formula (I) or as in Formula (I.1).

In another embodiment, in Formula (I), X is $C(R^X)$ and the compounds of the invention have the structural Formula (IA):

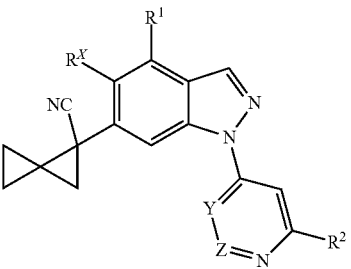

(IA)

or a pharmaceutically acceptable salt thereof, wherein:
$R^X$ is H, F, Cl, or $CH_3$; and
=Y—Z=, $R^1$, and $R^2$ are as defined in Formula (I) or as in Formula (I.1).

In another embodiment, in Formula (I'), X is $C(R^X)$ and the compounds of the invention have the structural Formula (IA'):

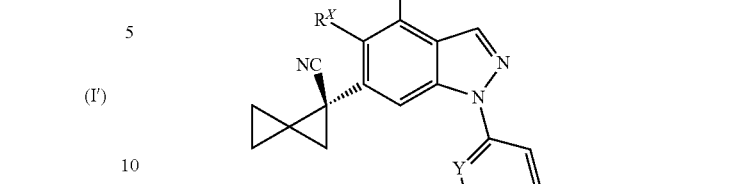

(IA')

or a pharmaceutically acceptable salt thereof, wherein:
$R^X$ is H, F, Cl, or $CH_3$; and
=Y—Z=, $R^1$, and $R^2$ are as defined in Formula (I) or as in Formula (I.1).

In another embodiment, in Formula (I"), X is $C(R^X)$ and the compounds of the invention have the structural Formula (IA"):

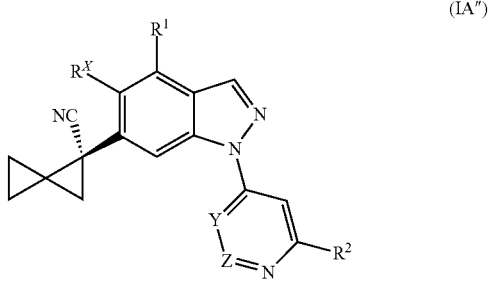

(IA")

or a pharmaceutically acceptable salt thereof, wherein:
$R^X$ is H, F, Cl, or $CH_3$; and
=Y—Z=, $R^1$, and $R^2$ are as defined in Formula (I) or as in Formula (I.1).

It shall be understood that =Y—Z=, in Formula (I) and each of the embodiments described herein which refer to =Y—Z=, the expression =Y—Z= refers to the portion of the moiety

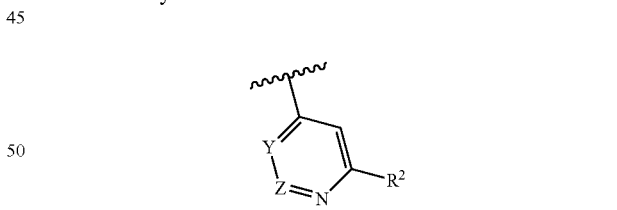

shown in the formula.

In another embodiment, in each of Formulas (IA), (IA') and (IA"):
=Y—Z= is =N—$C(R^Z)$=; and $R^Z$, $R^1$, and $R^2$ are as defined in Formula (I) or as in Formula (I.1). In an alternative of this embodiment, $R^1$ is H. In another alternative of this embodiment, $R^1$ is F.

In another embodiment, in each of Formulas (I), (I'), (I"), (IA), (IA') and (IA"):
=Y—Z= is =C(H)—$C(R^Z)$=; and $R^Z$, $R^1$, and $R^2$ are as defined in Formula (I) or as in Formula (I.1). In an alternative of this embodiment, $R^1$ is H. In another alternative of this embodiment, $R^1$ is F.

In another embodiment, in each of Formulas (IA), (IA') and (IA"):

=Y—Z= is =C(H)—N=; and $R^1$ and $R^2$ are as defined in Formula (I) or as in Formula (I.1). In an alternative of this embodiment, $R^1$ is H. In another alternative of this embodiment, $R^1$ is F.

In another embodiment, in Formula (I), X is N and the compounds of the invention have the structural Formula (IB):

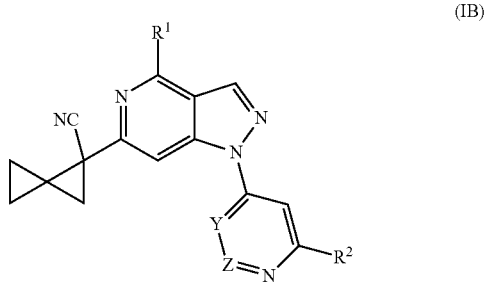

(IB)

or a pharmaceutically acceptable salt thereof, wherein:
=Y—Z=, $R^1$ and $R^2$ are as defined in Formula (I) or as in Formula (I.1).

In another embodiment, in Formula (I'), X is N and the compounds of the invention have the structural Formula (IB'):

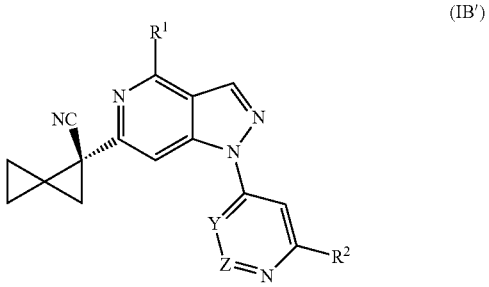

(IB')

or a pharmaceutically acceptable salt thereof, wherein:
=Y—Z=, $R^1$ and $R^2$ are as defined in Formula (I) or as in Formula (I.1).

In another embodiment, in Formula (I"), X is N and the compounds of the invention have the structural Formula (IB"):

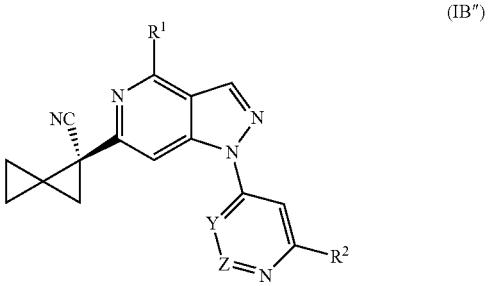

(IB")

or a pharmaceutically acceptable salt thereof, wherein:
=Y—Z=, $R^1$ and $R^2$ are as defined in Formula (I) or as in Formula (I.1).

In another embodiment, in each of Formulas (IB), (IB'), and (IB"):

=Y—Z= is =N—C($R^Z$)=; and $R^1$ and $R^2$ are as defined in Formula (I) or as in Formula (I.1).

In an alternative of this embodiment, $R^1$ is H. In another alternative of this embodiment, $R^1$ is F.

In another embodiment, in each of Formulas (IB), (IB'), and (IB"):

=Y—Z= is =C(H)—C($R^Z$)=; and $R^1$ and $R^2$ are as defined in Formula (I) or as in Formula (I.1). In an alternative of this embodiment, $R^1$ is H. In another alternative of this embodiment, $R^1$ is F.

In another embodiment, in each of Formulas (IB), (IB'), and (IB"):

=Y—Z= is =C(H)—N=; and $R^1$ and $R^2$ are as defined in Formula (I) or as in Formula (I.1).

In an alternative of this embodiment, $R^1$ is H. In another alternative of this embodiment, $R^1$ is F.

In another alternative embodiment, in each of Formulas (I), (I'), (I"), (IA), (IA'), (IA"), (IB), (IB'), and (IB"), and in each of the alternative embodiments thereof described above, $R^X$ (when present) is H, F, Cl, or $CH_3$.

In another alternative embodiment, in each of Formulas (I), (I'), (I"), (IA), (IA'), (IA"), (IB), (IB'), and (IB"), and in each of the alternative embodiments thereof described above, $R^Z$ (when present) is H, F, —$CH_3$, —$NH_2$, —$CH_2CH_3$, —$NHCH_3$, —O—$CH_3$, —S—$CH_3$, —$CH_2OH$, —$CH_2O$—$CH_3$, —$NHCH_3$,

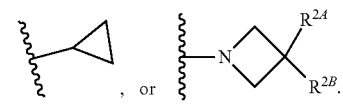

In another alternative embodiment, in each of Formulas (I), (I'), (I"), (IA), (IA'), (IA"), (IB), (IB'), and (IB), and in each of the alternative embodiments thereof described above, $R^{2A}$ is H, F, —OH, —$CH_3$, —$CHF_2$, $CH_3$, —$OCH_3$, —$C(OH)(CH_3)_2$, —$CH_2OH$, —$CH_2O$—$CH_3$, —$C(CH_3)_2$(OH), cyclopropyl, or;

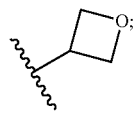 [SMILES: *C1COC1]

$R^{2B}$ is H, F, —OH, —$CH_3$, —$C(CH_3)_2(OH)$, —$CH_2OH$, —$CH_2O$—$CH_3$, or

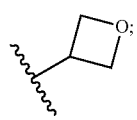 [SMILES: *C1COC1]

$R^{2B1}$ is H, F, or $CH_3$;

$R^{2C}$ is H, $-CH_3$, $-SO_2CH_3$,

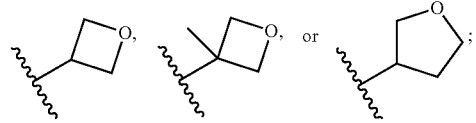

$R^{2D}$ is H, $CH_3$, $-CH_2OH$, or $-CH_2OCH_3$; and $R^{2E}$ is H, $CH_3$, $-CH_2CF_3$,

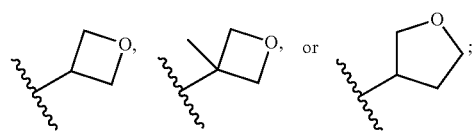

$R^{2F}$ is H, $-(C_1-C_6)$alkyl, $-(C_1-C_6)$fluoroalkyl, $-CH_2-O-CH_3$,

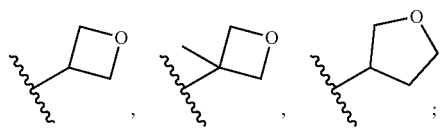

and $R^{2G}$ is H, $CH_3$, or $-CH_2CF_3$.

In another alternative embodiment, in each of Formulas (I), (I'), (I"), (IA), (IA'), (IA"), (IB), (IB'), and (IB"), and in each of the alternative embodiments thereof described above, $R^X$ (when present) is H, F, Cl, or $CH_3$;

$R^Z$ (when present) is H, F, $-CH_3$, $-NH_2$, $-CH_2CH_3$, $-NHCH_3$, $-O-CH_3$, $-S-CH_3$, $-CH_2OH$, $-CH_2O-CH_3$, $-NHCH_3$,

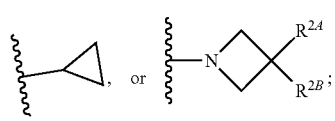

$R^{2A}$ (when present) is H, F, $-OH$, $-CH_3$, $-CHF_2$, $CH_3$, $-OCH_3$, $-C(OH)(CH_3)_2$, $-CH_2OH$, $-CH_2O-CH_3$, $-C(CH_3)_2(OH)$, cyclopropyl, or

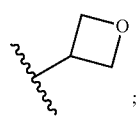 [SMILES: *C1COC1]

$R^{2B}$ (when present) is H, F, $-OH$, $-CH_3$, $-C(CH_3)_2$ (OH), $-CH_2OH$, $-CH_2O-CH_3$, or

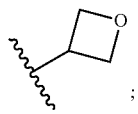 [SMILES: *C1COC1]

$R^{2B1}$ (when present) is H, F, or $CH_3$;

$R^{2C}$ (when present) is H, $-CH_3$, $-SO_2CH_3$,

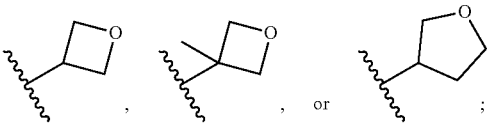

$R^{2D}$ (when present) is H, $CH_3$, $-CH_2OH$, or $-CH_2OCH_3$; and $R^{2E}$ (when present) is H, $CH_3$, $-CH_2CF_3$,

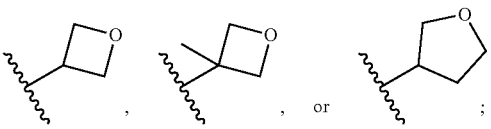

$R^{2F}$ (when present) is H, $-(C_1-C_6)$alkyl, $-(C_1-C_6)$fluoroalkyl, $-CH_2-CH_3$,

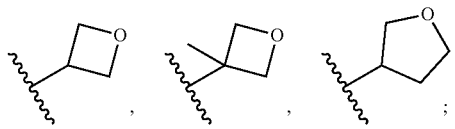

and $R^{2G}$ (when present) is H, $CH_3$, or $-CH_2CF_3$.

In another embodiment, the compounds of the invention include those identified herein as Examples in the tables below, and pharmaceutically acceptable salts thereof.

In another embodiment, the present invention provides pharmaceutical compositions comprising a pharmaceutically acceptable carrier and a compound of the invention or a pharmaceutically acceptable salt thereof.

In another embodiment, the present invention provides a method of treating a disease or disorder in which the LRRK2 kinase is involved, or one or more symptoms or conditions associated with said diseases or disorders, said method comprising administering to a subject (e.g., mammal, person, or patient) in need of such treatment an effective amount of a compound of the invention, or a pharmaceutically acceptable salt thereof, or pharmaceutically acceptable composition thereof. Non-limiting examples of such diseases or disorders, and symptoms associated with such diseases or disorders, each of which comprise additional independent embodiments of the invention, are described below.

Another embodiment provides the use of a compound of the invention, or a pharmaceutically acceptable salt thereof, and a pharmaceutically acceptable carrier, for the manufacture of a medicament for the treatment of Parkinson's Disease. The invention may also encompass the use of a compound of the invention, or a pharmaceutically acceptable salt thereof, and a pharmaceutically acceptable carrier, in therapy.

Another embodiment provides for medicaments or pharmaceutical compositions which may be useful for treating diseases or disorders in which LRRK2 is involved, such as Parkinson's Disease, which comprise a compound of the invention, or a pharmaceutically acceptable salt thereof, and a pharmaceutically acceptable carrier.

Another embodiment provides for the use of a compound of the invention which may be useful for treating diseases or disorders in which LRRK2 is involved, such as Parkinson's Disease.

Another embodiment provides a method for the manufacture of a medicament or a composition which may be useful for treating diseases or disorders in which LRRK2 is involved, such as Parkinson's Disease, comprising combining a compound of the invention with one or more pharmaceutically acceptable carriers.

The compounds of the invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. Unless a specific stereochemistry is indicated, the present invention is meant to encompass all such isomeric forms of these compounds.

The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration.

If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art.

Alternatively, any enantiomer of a compound may be obtained by stereoselective synthesis using optically pure starting materials or reagents of known configuration by methods well known in the art.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium (2H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

When a compound of the invention is capable of forming tautomers, all such tautomeric forms are also included within the scope of the present invention. For example, compounds including carbonyl —$CH_2C(O)$— groups (keto forms) may undergo tautomerism to form hydroxyl —$CH\!=\!C(OH)$— groups (enol forms). Both keto and enol forms, where present, are included within the scope of the present invention.

When any variable (e.g. $R^5$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is bicyclic, it is intended that the bond be attached to any of the suitable atoms on either ring of the bicyclic moiety.

It is understood that one or more silicon (Si) atoms can be incorporated into the compounds of the instant invention in place of one or more carbon atoms by one of ordinary skill in the art to provide compounds that are chemically stable and that can be readily synthesized by techniques known in the art from readily available starting materials. Carbon and silicon differ in their covalent radius leading to differences in bond distance and the steric arrangement when comparing analogous C-element and Si-element bonds. These differences lead to subtle changes in the size and shape of silicon-containing compounds when compared to carbon. One of ordinary skill in the art would understand that size and shape differences can lead to subtle or dramatic changes in potency, solubility, lack of off-target activity, packaging properties, and so on. (Diass, J. O. et al. Organometallics (2006) 5:1188-1198; Showell, G. A. et al. Bioorganic & Medicinal Chemistry Letters (2006) 16:2555-2558).

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted with one or more substituents" should be understood as meaning that the group in question is either unsubstituted or may be substituted with one or more substituents.

"($C_1$-$C_6$)Alkyl" means an aliphatic hydrocarbon group, which may be straight or branched, comprising 1 to 6 carbon atoms. Branched means that one or more lower alkyl groups such as methyl, ethyl or propyl, are attached to a linear alkyl chain. Non-limiting examples of alkyl groups include methyl, ethyl, n-propyl, isopropyl, n-butyl, i-butyl, and t-butyl.

"Haloalkyl" means an alkyl as defined above wherein one or more hydrogen atoms on the alkyl is replaced by a halogen atom. As appreciated by those of skill in the art, "halo" or "halogen" as used herein is intended to include chloro (Cl), fluoro (F), bromo (Br) and iodo (I). Chloro (Cl) and fluoro(F) halogens are generally preferred.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives wherein the parent compound is modified by making acid or base salts thereof. Salts in the solid form may exist in more than one crystal structure, and may also be in the form of hydrates. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. Salts derived from inorganic bases include aluminum, ammonium, calcium, copper, ferric, ferrous, lithium, magnesium, manganic salts, manganous, potassium, sodium, zinc, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. In one aspect of the invention the salts are citric, hydrobromic, hydrochloric, maleic, phosphoric, sulfuric, fumaric, and tartaric acids. Similarly, the salts of the acidic compounds are formed by reactions with the appropriate inorganic or organic base.

The terms "treating" or "treatment" (of, e.g., a disease, disorder, or conditions or associated symptoms, which together or individually may be referred to as "indications") as used herein include: inhibiting the disease, disorder or condition, i.e., arresting or reducing the development of the disease or its biological processes or progression or clinical symptoms thereof; or relieving the disease, i.e., causing regression of the disease or its biological processes or progression and/or clinical symptoms thereof. "Treatment" as used herein also refers to control, amelioration, or reduction of risks to the subject afflicted with a disease, disorder or condition in which LRRK2 is involved. The terms "preventing" or "prevention" or "prophylaxis" of a disease, disorder or condition as used herein includes: impeding the development or progression of clinical symptoms of the disease, disorder, or condition in a mammal that may be exposed to or predisposed to the disease, disorder or condition but does not yet experience or display symptoms of the disease, and the like.

As would be evident to those skilled in the art, subjects treated by the methods described herein are generally mammals, including humans and non-human animals (e.g., laboratory animals and companion animals), in whom the inhibition of LRRK2 kinase activity is indicated or desired. The term "therapeutically effective amount" means the amount of the subject compound that will elicit the biological or medical response of a tissue, system, animal or human that is being sought by the researcher, veterinarian, medical doctor or other clinician.

The term "composition" as used herein is intended to encompass a product comprising a compound of the invention or a pharmaceutically acceptable salt thereof, together with one or more additional specified ingredients in the specified amounts, as well as any product which results, directly or indirectly, from combination of the specified ingredients in the specified amounts. Such term in relation to a pharmaceutical composition, is intended to encompass a product comprising the active ingredient(s), which include a compound of the invention or a pharmaceutically acceptable salt thereof, optionally together with one or more additional active ingredients, and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a compound of the present invention, or a pharmaceutically acceptable salt thereof, and a pharmaceutically acceptable carrier. By "pharmaceutically acceptable" it is meant the carrier, diluent or excipient must be compatible with the other ingredients of the formulation and not deleterious to the recipient thereof.

As noted above, additional embodiments of the present invention are each directed to a method for the treatment a disease, disorder, or condition, or one or more symptoms thereof ("indications") in which the LRRK2 kinase is involved and for which the inhibition of LRRK2 kinase is desired, which method comprises administering to a subject in need of such treatment a therapeutically effective amount of a compound of the invention, or a pharmaceutically acceptable salt thereof, or a pharmaceutical composition comprising said compound or salt thereof.

In another embodiment, the present invention is directed to a method for the manufacture of a medicament for inhibition of LRRK2 receptor activity in a subject comprising combining a compound of the present invention, or a pharmaceutically acceptable salt thereof, with a pharmaceutical carrier or diluent.

One such embodiment provides a method of treating Parkinson's disease in a subject in need thereof, said method comprising administering to a subject in need of such treatment a therapeutically effective amount of a compound of the invention, or a pharmaceutically acceptable salt thereof, or a pharmaceutical composition comprising said compound or salt thereof. In one such embodiment, the subject is a human.

Another embodiment provides a method for the treatment or prophylaxis of neurologic damage associated with Parkinson's disease in a subject in need thereof. Another embodiment provides a method of treating or improving dopaminergic tone to provide symptomatic relief in a subject in need thereof, for example, in treating, alleviating, ameliorating, or managing motor and non-motor symptoms of Parkinson's disease.

Another embodiment provides a method for the treatment or prophylaxis of abnormal motor symptoms associated with Parkinson's disease (including but not limited to bradykinesia, rigidity and resting tremor). Another embodiment provides a method for the treatment or prophylaxis of abnormal non-motor symptoms associated with Parkinson's disease (including but not limited to cognitive dysfunction, autonomic dysfunction, emotional changes and sleep disruption); Lewy body dementia; and L-Dopa induced dyskinesias. Each said method independently comprises administering to a patient in need of such treatment an effective amount of a compound of the invention, or a pharmaceutically acceptable salt thereof, or pharmaceutically acceptable composition thereof.

Non-limiting examples of additional indications in which LRRK2 is involved and in which the treatment or prophylaxis of said indications in a subject in need thereof are contemplated include the following, each of which, alone or in combination, comprise additional embodiments of the invention: Alzheimer's disease, mild cognitive impairment, the transition from mild cognitive impairment to Alzheimer's disease, tauopathy disorders characterized by hyperphosphorylation of tau such as argyrophilic grain disease, Picks disease, corticobasal degeneration, progressive supranuclear palsy, inherited frontotemporal dementia, and Parkinson's disease linked to chromosome 17.

Additional indications include neuroinflammation, including neuroinflammation associated with of microglial inflammatory responses associated with multiple sclerosis, HIV-induced dementia, ALS, ischemic stroke, traumatic brain injury and spinal cord injury.

Additional indications include diseases of the immune system including lymphomas, leukemias, multiple sclerosis, rheumatoid arthritis, systemic lupus erythematosus, autoimmune hemolytic anemia, pure red cell aplasia, idiopathic thrombocytopenic pupura (ITP), Evans Syndrome, vasculitis, bullous skin disorder, type I diabetes mellitus, Sjorgen's syndrome, Delvic's disease, inflammatory myopathies, and ankylosing spondylitis.

Additional indications include renal cancer, breast cancer, lung cancer, prostate cancer, and acute myelogenous leukemia (AML) in subjects expressing the LRRK2 G2019S mutation.

Additional indications include papillary renal and thyroid carcinomas in a subject in whom LRRK2 is amplified or overexpressed.

Additional indications include chronic autoimmune diseases including Crohn's disease and leprosy.

The present invention includes within its scope prodrugs of the compounds of this invention. In general, such prodrugs will be functional derivatives of the compounds of this invention which are readily convertible in vivo into the required compound. Thus, in the methods of treatment of the present invention, the terms "administration of" or "administering a" compound shall encompass the treatment of the various conditions described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs," ed. H. Bundgaard, Elsevier, 1985. Metabolites of these compounds include active species produced upon introduction of compounds of this invention into the biological milieu.

The compounds of the present invention may be used in combination with one or more other drugs in the treatment, prevention, control, amelioration, or reduction of risk of diseases or conditions for which compounds of the invention or the other drugs may have utility, where the combination of the drugs together are safer or more effective than either drug alone. Such other drug(s) may be administered, by a route and in an amount commonly used therefore, contemporaneously or sequentially with a compound of Formula I. When a compound of Formula I is used contemporaneously with one or more other drugs, a pharmaceutical composition in unit dosage form containing such other drugs and the compound of Formula I is preferred. However, the combination therapy may also include therapies in which the compound of Formula I and one or more other drugs are administered on different overlapping schedules. It is also contemplated that when used in combination with one or more other active ingredients, the compounds of the present invention and the other active ingredients may be used in lower doses than when each is used singly. Accordingly, the pharmaceutical compositions of the present invention include those that contain one or more other active ingredients, in addition to a compound of Formula I.

For example, the present compounds may be used in conjunction with one or more additional therapeutic agents, for example: L-DOPA; dopaminergic agonists such as quinpirole, ropinirole, pramipexole, pergolide and bromocriptine; MAO-B inhibitors such as rasagiline, deprenyl and selegiline; DOPA decarboxylase inhibitors such as carbidopa and benserazide; and COMT inhibitors such as tolcapone and entacapone; or potential therapies such as an adenosine A2a antagonists, metabotropic glutamate receptor 4 modulators, or growth factors such as brain derived neurotrophic factor (BDNF), and a pharmaceutically acceptable carrier.

The above combinations include combinations of a compound of the present invention not only with one other active compound, but also with two or more other active compounds. Likewise, compounds of the present invention may be used in combination with other drugs that are used in the prevention, treatment, control, amelioration, or reduction of risk of the diseases or conditions for which compounds of the present invention are useful. Such other drugs may be administered, by a route and in an amount commonly used therefore, contemporaneously or sequentially with a compound of the present invention. When a compound of the present invention is used contemporaneously with one or more other drugs, a pharmaceutical composition containing such other drugs in addition to the compound of the present invention is preferred. Accordingly, the pharmaceutical compositions of the present invention include those that also contain one or more other active ingredients, in addition to a compound of the present invention.

The weight ratio of the compound of the present invention to the other active ingredient(s) may be varied and will depend upon the effective dose of each ingredient. Generally, an effective dose of each will be used. Thus, for example, when a compound of the present invention is combined with another agent, the weight ratio of the compound of the present invention to the other agent will generally range from about 1000:1 to about 1:1000, or from about 200:1 to about 1:200. Combinations of a compound of the present invention and other active ingredients will generally also be within the aforementioned range, but in each case, an effective dose of each active ingredient should be used.

In such combinations the compound of the present invention and other active agents may be administered separately or in conjunction. In addition, the administration of one element may be prior to, concurrent to, or subsequent to the administration of other agent(s), and via the same or different routes of administration.

The compounds of the present invention may be administered by oral, parenteral (e.g., intramuscular, intraperitoneal, intravenous, ICV, intracisternal injection or infusion, subcutaneous injection, or implant), by inhalation spray, nasal, vaginal, rectal, sublingual, buccal or topical routes of administration and may be formulated, alone or together, in suitable dosage unit formulations containing conventional non-toxic pharmaceutically acceptable carriers, adjuvants and vehicles appropriate for each route of administration. In addition to the treatment of warm-blooded animals the compounds of the invention are effective for use in humans.

The pharmaceutical compositions for the administration of the compounds of this invention may conveniently be presented in dosage unit form and may be prepared by any of the methods well known in the art of pharmacy. All methods include the step of bringing the active ingredient into association with the carrier which constitutes one or more accessory ingredients. In general, the pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound is included in an amount sufficient to produce the desired effect upon the process or condition of diseases. As used herein, the term "composition" is intended to encompass a product comprising the specified ingredients in the specified amounts, as well as any product which results, directly or indirectly, from combination of the specified ingredients in the specified amounts.

The pharmaceutical compositions containing the active ingredient may be in a form suitable for oral use, for example, as tablets, troches, lozenges, aqueous or oily suspensions, dispersible powders or granules, emulsions, solutions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia; and lubricating agents, for example magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,166,452; and 4,265,874 to form osmotic therapeutic tablets for control release. Oral tablets may also be formulated for immediate release, such as fast melt tablets or wafers, rapid dissolve tablets or fast dissolve films.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcellulose, hydroxy-propylmethylcellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents, such as sucrose or saccharin.

Oily suspensions may be formulated by suspending the active ingredient in a vegetable oil, for example *arachis* oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present.

The pharmaceutical compositions of the invention may also be in the form of oil-in-water emulsions. The oily phase may be a vegetable oil, for example olive oil or *arachis* oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents.

The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of the present invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

For topical use, creams, ointments, jellies, solutions or suspensions and the like, containing the compounds of the present invention are employed. Similarly, transdermal patches may also be used for topical administration.

The pharmaceutical composition and method of the present invention may further comprise other therapeutically active compounds as noted herein which are usually applied in the treatment of the above mentioned pathological conditions.

In the treatment, prevention, control, amelioration, or reduction of risk of conditions which require inhibition of LRRK2 kinase activity an appropriate dosage level will generally be about 0.01 to 500 mg per kg patient body weight per day which can be administered in single or multiple doses. A suitable dosage level may be about 0.01 to 250 mg/kg per day, about 0.05 to 100 mg/kg per day, or about 0.1 to 50 mg/kg per day. Within this range the dosage may be 0.05 to 0.5, 0.5 to 5 or 5 to 50 mg/kg per day. For oral administration, the compositions may be provided in the form of tablets containing 1.0 to 1000 milligrams of the active ingredient, particularly 1.0, 5.0, 10.0, 15.0. 20.0, 25.0, 50.0, 75.0, 100.0, 150.0, 200.0, 250.0, 300.0, 400.0, 500.0, 600.0, 750.0, 800.0, 900.0, and 1000.0 milligrams of the active ingredient for the symptomatic adjustment of the dosage to the patient to be treated. The compounds may be administered on a regimen of 1 to 4 times per day, or may be administered once or twice per day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Methods for preparing the compounds of this invention are illustrated in the following Schemes and Examples. Starting materials are made according to procedures known in the art or as illustrated herein.

Preparative Examples

The compounds of the present invention can be prepared readily according to the following schemes and specific examples, or modifications thereof, using readily available starting materials, reagents and conventional synthesis procedures. In these reactions, it is also possible to make use of variants which are themselves known to those of ordinary skill in this art but are not mentioned in detail. The general procedures for making the compounds claimed in this invention can be readily understood and appreciated by one skilled in the art from viewing the following Schemes and descriptions.

General Schemes

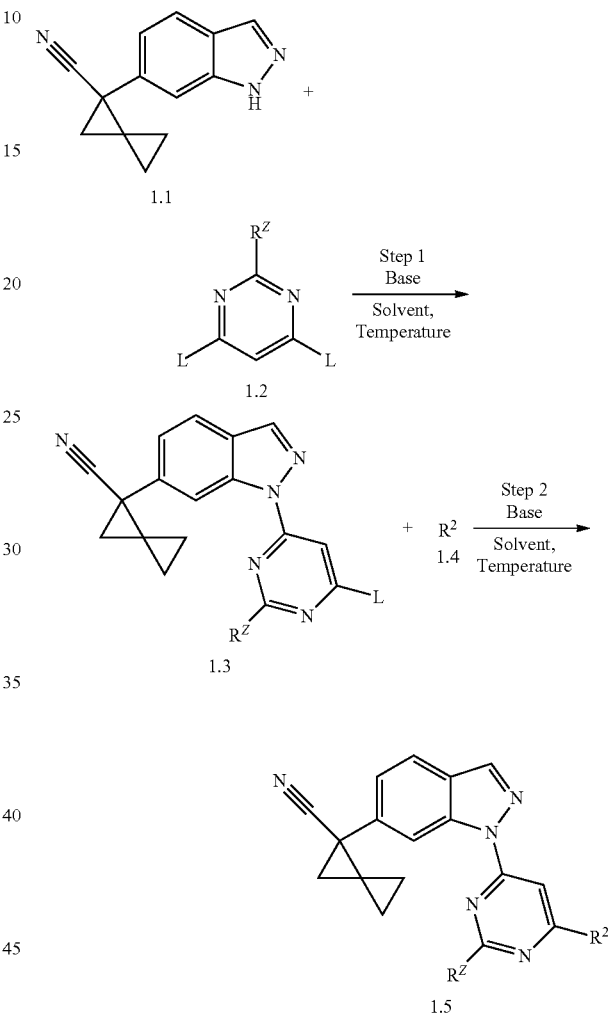

One general strategy for the synthesis of products of type 1.5 is via a two-step procedure outlined in General Scheme 1, wherein L is a halogen and $R^Z$ and $R^2$ are defined in Formula I. Building block 1.1 and building blocks of type 1.2 are combined with a base such as, cesium carbonate, sodium hydride or potassium carbonate in solvents such as, DMF or DMA. Heating the reaction at the appropriate temperature can provide intermediates of type 1.3. These intermediates are isolated or the second reaction can be performed in the same vessel without isolation of intermediate 1.3. Intermediates of type 1.3 and different amines of type 1.4 are combined and under the action of bases such as cesium carbonate or DIPEA, in appropriate solvent such as DMA, DMF or DMSO, with heating at the appropriate temperature, produces products of type 1.5. Products of type 1.5 can be purified by silica gel chromatography, preparative reverse-phase HPLC or SFC.

General Scheme 2

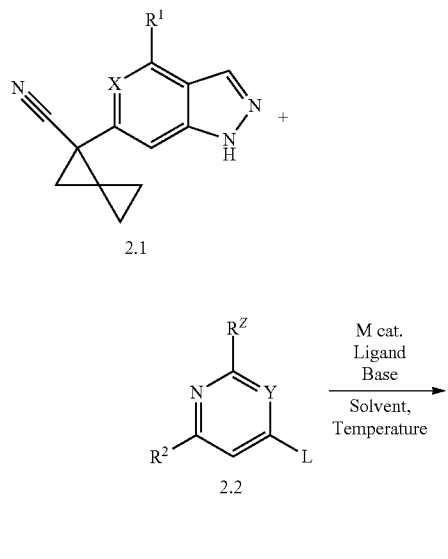

One general strategy for the synthesis of products of type 2.3 is outlined in General Scheme 2, wherein L is a halogen and $R^1$, $R^2$, $R^Z$, X and Y are as defined in Formula I. Combination of building block 2.1 and building blocks of type 2.2 under the action of an appropriate metal catalyst, ligand, base, solvent and temperature can produce products of type 2.3. Products of type 2.3 can be purified by silica gel chromatography, preparative reverse-phase HPLC or SFC.

General Scheme 3

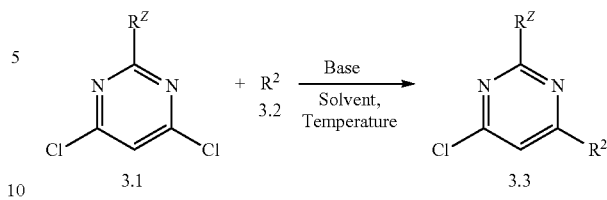

One general strategy for the synthesis of products of type 3.3 is outlined in General Scheme 3, wherein $R^Z$ and $R^2$ are as defined in Formula I. Pyrimidines 3.1 are combined with various amines of type 3.2 with the appropriate base and solvent and are heated for an appropriate amount of time to provide products 3.3. Bases such as, potassium carbonate or DIPEA, and solvents such as, DMF, DMSO, MeCN, DMA and NMP can be used. Products of type 3.3 can be purified by silica gel chromatography, preparative reverse-phase HPLC, SFC, precipitation or can be used without purification.

General Scheme 4

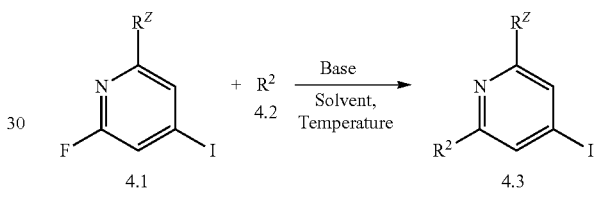

One general strategy for the synthesis of products of type 4.3 is outlined in General Scheme 4, wherein $R^Z$ and $R^2$ are as defined in Formula I. Combination pyridines 4.1 with various amines of type 4.2 under the action of bases such as potassium carbonate, triethylamine or DIPEA, and solvents such as, DMF, DMSO, MeCN, DMA and NMP after heating to the appropriate temperature, products of type 4.3 are obtained. Products of type 4.3 can be purified by silica gel chromatography, preparative reverse-phase HPLC, SFC, precipitation or used without purification.

Experimentals

Abbreviations used in the experimentals may include, but are not limited to the following:

| | |
|---|---|
| AcOH | Acetic Acid |
| AdBrettPHos-Pd-G3 | Di-Ad-BrettPhos-G3-Palladacycle, [2-(Di-1-adamantylphosphino)-2',4',6'-triisopropyl-3,6-dimethoxybiphenyl][2-(2'-amino-1,1'-biphenyl)]palladium(II) methanesulfonate (MFCD27952546) 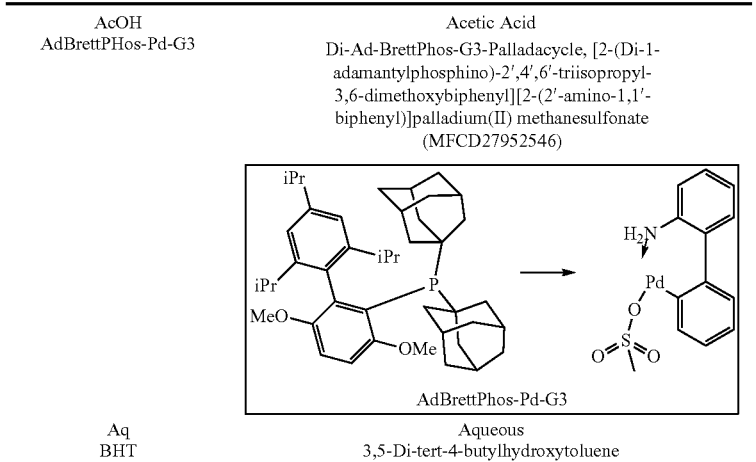 |
| Aq | Aqueous |
| BHT | 3,5-Di-tert-4-butylhydroxytoluene |

-continued

| | |
|---|---|
| CPME | Cyclopentyl methyl ether |
| DAST | Diethylaminosulfur trifluoride |
| DCE | Dichloroethane |
| DCM | Dichloromethane |
| DIPA | N,N-Diisopropylamine |
| DIPEA | N,N-Diisopropylethylamine |
| DMA | Dimethylacetamide |
| DMEA | Dimethylethylamine |
| DMF | Dimethylformamide |
| DMSO | Dimethyl sulfoxide |
| EtOAc | Ethyl acetate |
| ESI | Electrospray ionization |
| H | Hours |
| HPLC | High performance liquid chromatography |
| IPA | Isopropyl alcohol |
| Josiphos-SL-J009-1-Pd-G3 | {(R)-1-[(Sp)-2-(Dicyclohexylphosphino)ferrocenyl]ethyldi-tert-butylphosphine}[2-(2′-amino-1,1′-biphenyl)]palladium(II) methanesulfonate (MFCD27978424) |

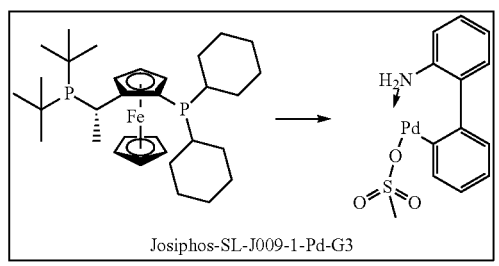
Josiphos-SL-J009-1-Pd-G3

| | |
|---|---|
| LCMS | Liquid chromatography-mass spectrometry |
| LiHMDS | Lithium bis(trimethylsilyl)amide |
| MeCN | Acetonitrile |
| MeOH | Methanol |
| MS | Mass spectrometry |
| NiXantPhos | 4,6-Bis(diphenylphosphino)-10H-phenoxazine, 4,6-Bis(diphenylphosphino)phenoxazine (MFCD03788937) |

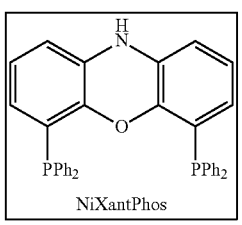
NiXantPhos

| | |
|---|---|
| NiXantPhos-Pd-G3 | MFCD28144626 |

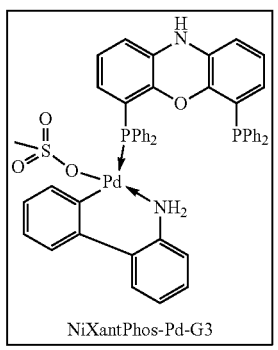
NiXantPhos-Pd-G3

| | |
|---|---|
| tBu-Xphos-Pd-G4 | 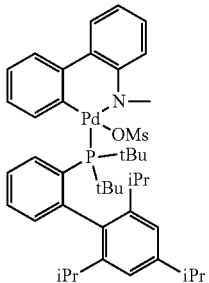 |
| NMP | N-Methyl-2-pyrrolidone |
| Pd₂dba₃ | Tris(dibenzylideneacetone)dipalladium(0) |
| Pd-C | Palladium on Carbon |
| PE | Petroleum Ether |
| Psi | Pounds per square inch |
| RT | Retention time |
| Rt | Room temperature |
| SFC | Supercritical Fluid Chromatography |
| Si-DPP-Pd | SiliaCat DPP-Pd Heterogeneous Catalyst (R390-100), supplier Silicycle |
| TFA | Trifluoroacetic acid |
| THF | Tetrahydrofuran |
| TLC | Thin Layer Chromatography |

General Experimental Information:

Unless otherwise noted, all reactions are magnetically stirred.

Unless otherwise noted, when diethyl ether is used in the experiments described below, it is Fisher ACS certified material and is stabilized with BHT.

Unless otherwise noted, "concentrated" means evaporating the solvent from a solution or mixture using a rotary evaporator or vacuum pump.

Unless otherwise noted, flash chromatography is carried out on an Isco, Analogix, or Biotage automated chromatography system using a commercially available cartridge as the column. Columns may be purchased from Isco, Analogix, Biotage, Varian, or Supelco and are usually filled with silica gel as the stationary phase. Reverse phase prep-HPLC conditions can be found at the end of experimental section. Aqueous solutions were concentrated on a Genevac or were lyophilized.

Unless otherwise noted, all LRRK2 $IC_{50}$ data presented in tables refers to the LRRK2 G2019S Km ATP LanthaScreen™ Assay that is described in the Biological Assay section.

Preparation of Common Intermediates

Preparation of Intermediate A.3, (3R,4s,5S)-3,4,5-trimethylpiperidin-4-ol, HCl Salt Scheme A

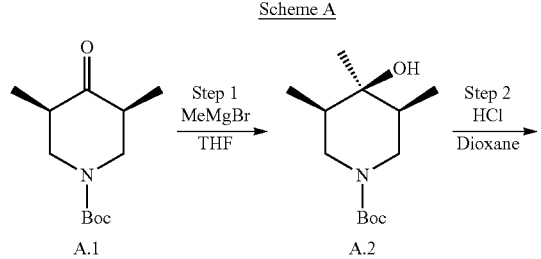

-continued

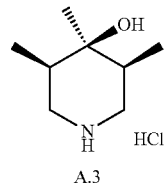

Step 1—Synthesis of A.2, tert-butyl (3R,4s,5S)-4-hydroxy-3,4,5-trimethylpiperidine-1-carboxylate A 5000-mL 4-necked round-bottom flask was charged with tert-butyl (3R,5S)-3,5-dimethyl-4-oxopiperidine-1-carboxylate (200 g, 880 mmol) and THF (2 L). This was followed by the addition of MeMgBr (1.4 M THF/Toluene, 733 mL) dropwise with stirring at −50° C. The resulting solution was stirred for 2 h at room temperature. The reaction was then quenched by the addition of saturated $NH_4Cl_{(aq)}$ (1 L). The resulting solution was extracted with EtOAc (2×2 L) and the organic layers combined and dried over anhydrous $Na_2SO_4$. The resulting mixture was washed with heptane (1×500 mL) to afford tert-butyl (3R,4s,5S)-4-hydroxy-3,4,5-trimethylpiperidine-1-carboxylate.

Step 2—Synthesis of A.3, (3R,4s,5S)-3,4,5-trimethylpiperidin-4-ol

A 2-L 4-necked round-bottom flask was charged with tert-butyl (3R,4s,5S)-4-hydroxy-3,4,5-trimethylpiperidine-1-carboxylate (170 g, 699 mmol), and MeOH (500 mL). This was followed by the addition of hydrogen chloride (4M in dioxane, 200 mL) dropwise with stirring at room temperature. The resulting solution was stirred for 2 h at room temperature. The resulting mixture was concentrated under vacuum. The resulting mixture was washed with methyl tert-butyl ether (1×500 mL) to afford (3R,4s,5S)-3,4,5-trimethylpiperidin-4-ol as an HCl salt. MS (ESI) m/z calc'd for $C_8H_{18}NO$ $[M+H]^+$ 144 found 144.

Preparation of Intermediate B.4, 2-(2-azabicyclo[2.1.1]hexan-4-yl)propan-2-ol, TFA Salt

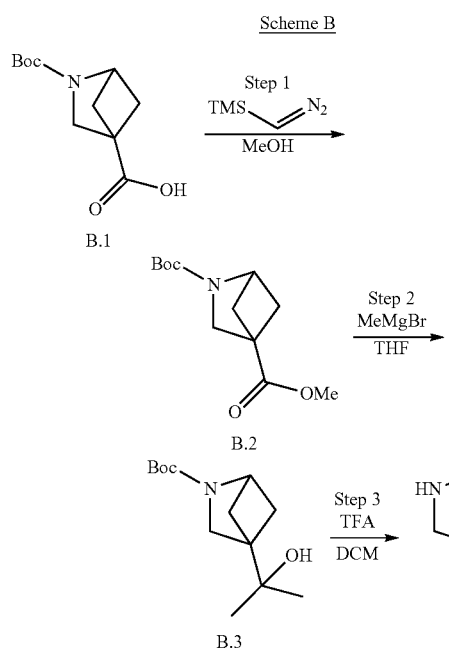

Step 1—Synthesis of B.2, 2-(tert-butyl) 4-methyl 2-azabicyclo[2.1.1]hexane-2,4-dicarboxylate (Trimethylsilyl)diazomethane (2M in hexanes, 2.34 mL, 4.68 mmol) was added to a solution of 2-(tert-butoxycarbonyl)-2-azabicyclo[2.1.1]hexane-4-carboxylic acid (0.532 g, 2.34 mmol) in MeOH (5 mL) at room temperature. The reaction was stirred for 1 h. Additional (Trimethylsilyl) diazomethane (2M in hexanes, 2.340 mL, 4.68 mmol) was added until a yellow color persisted and the solution was stirred overnight. The reaction was quenched with a few drops of acetic acid and a solution of aqueous citric acid (2M, 10 mL) was added to give pH=2 (litmus test). The mixture was diluted with ethyl acetate (250 mL), layers were separated and the organic layer was washed with saturated aqueous sodium hydrogen carbonate (2×250 mL), and then brine (1×250 mL). The organic layer was dried over Na$_2$SO$_4$, filtered and concentrated to afford 2-(tert-butyl) 4-methyl 2-azabicyclo[2.1.1]hexane-2,4-dicarboxylate. This material was carried on without further purification.

Step 2—Synthesis of B.3, tert-butyl 4-(2-hydroxypropan-2-yl)-2-azabicyclo[2.1.1]hexane-2-carboxylate Methylmagnesium bromide (3M in ether, 1.95 ml, 5.85 mmol) was added to a solution of 2-(tert-butyl) 4-methyl 2-azabicyclo[2.1.1]hexane-2,4-dicarboxylate, from step 1, in THF (10 ml) at 0° C. The reaction was warmed to room temperature and stirred overnight. The mixture was quenched with saturated aqueous ammonium chloride (50 mL) and the mixture was diluted with ethyl acetate (100 mL). The organic layer was washed with brine (3×50 mL), dried over Na$_2$SO$_4$, filtered and concentrated to afford tert-butyl 4-(2-hydroxypropan-2-yl)-2-azabicyclo[2.1.1] hexane-2-carboxylate. This material was carried on without further purification.

Step 3—Synthesis of B.4, 2-(2-azabicyclo[2.1.1] hexan-4-yl)propan-2-ol, TFA Salt The crude tert-butyl 4-(2-hydroxypropan-2-yl)-2-azabicyclo[2.1.1]hexane-2-carboxylate from above was diluted with DCM (10.00 ml) and treated with TFA (9.01 ml, 117 mmol) at room temperature. The reaction was stirred overnight and concentrated to afford 2-(2-azabicyclo[2.1.1] hexan-4-yl)propan-2-ol as a TFA salt. $^1$H NMR (400 MHz, DMSO-d$_6$) δ 8.97 (bs, 2H), 4.06 (s, 1H), 3.21-2.97 (m, 2H), 1.96-1.76 (m, 2H), 1.51-1.32 (m, 2H), 1.11 (s, 6H).

Preparation of intermediate C.3, (R)-2-methyl-1-(oxetan-3-yl)piperazine, TFA Salt

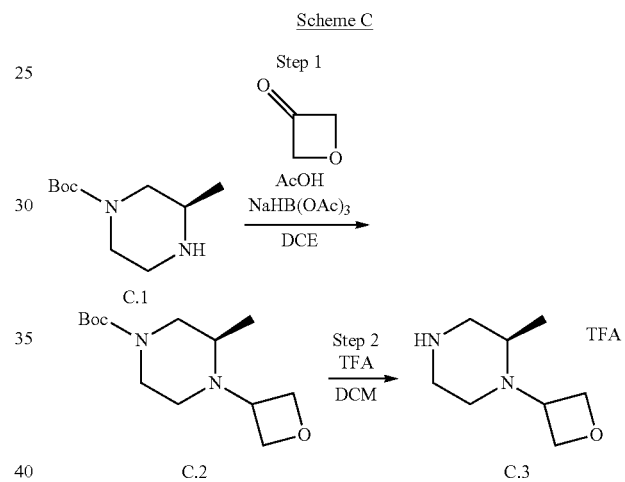

Step 1—Synthesis of C.2, (R)-tert-butyl 3-methyl-4-(oxetan-3-yl)piperazine-1-carboxylate A mixture containing (R)-tert-butyl 3-methylpiperazine-1-carboxylate (500 mg, 2.50 mmol) and oxetan-3-one (0.36 g, 5.0 mmol) in dichloroethane (10 mL) was treated with acetic acid (0.20 mL, 3.5 mmol) followed by sodium triacetoxyborohydride (1.0 g, 4.7 mmol). The reaction mixture was stirred at room temperature for 15 h, then diluted with DCM (30 mL) and washed with water (3×50 mL). The organic layer was dried over Na$_2$SO$_4$, filtered and concentrated to provide (R)-tert-butyl 3-methyl-4-(oxetan-3-yl)piperazine-1-carboxylate. This material was used without further purification.

Step 2—Synthesis of C.3, (R)-2-methyl-1-(oxetan-3-yl)piperazine, TFA Salt

A solution of (R)-tert-butyl 3-methyl-4-(oxetan-3-yl)piperazine-1-carboxylate (500 mg, 1.95 mmol) in DCM (2 mL) was treated with TFA (0.2 mL). The solution was aged for 2 h and then concentrated to provide (R)-2-methyl-1-(oxetan-3-yl)piperazine as a TFA salt. $^1$H NMR (400 MHz, DMSO-d$_6$) δ 9.00 (br s, 2H), 4.53-4.66 (m, 4H), 4.15 (br m, 1H), 3.27-3.38 (m, 2H), 3.09 (m, 2H), 2.93 (m, 2H), 2.59 (m, 1H), 1.00 (d, J=4 Hz, 3H).

Preparation of intermediate D.3,
(S)-2-methyl-1-(oxetan-3-yl)piperazine, TFA Salt Scheme D

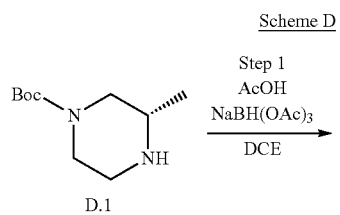

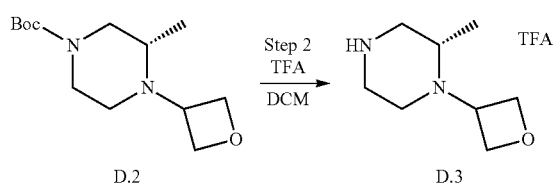

Step 1—Synthesis of D.2, tert-butyl(S)-3-methyl-4-(oxetan-3-yl)piperazine-1-carboxylate (S)-tert-butyl 3-methylpiperazine-1-carboxylate (3.0 g, 15 mmol) was taken up in DCE (30 mL). Acetic acid (1.2 mL, 21 mmol) and 3-oxetanone (1.8 mL, 30 mmol) were added and the reaction mixture was stirred for 1 h at room temperature. Sodium triacetoxyborohydride (6.1 g, 29 mmol) was added and the reaction mixture was stirred at room temperature for an additional 12 h. The reaction mixture was diluted with DCM and washed with water (3×100 mL). The organic phase was dried with magnesium sulfate, and concentrated under reduced pressure to afford tert-butyl (S)-3-methyl-4-(oxetan-3-yl)piperazine-1-carboxylate. This material was used without further purification.

Step 2—Synthesis of D.3,
(S)-2-methyl-1-(oxetan-3-yl)piperazine, TFA Salt (S)-tert-butyl 3-methyl-4-(oxetan-3-yl)piperazine-1-carboxylate (2.9 g, 11 mmol) was taken up in DCM (9 mL). Trifluoroacetic acid (2.0 mL, 26 mmol) was added and the reaction mixture was stirred at room temperature overnight. The crude reaction mixture was diluted in DCM and concentrated under reduced pressure to afford (S)-2-methyl-1-(oxetan-3-yl)piperazine as a TFA salt $^1$H NMR (499 MHz, DMSO-d$_6$) δ 8.82 (s, 2H), 4.57 (dd, J=6.1 Hz, 2H), 4.52 (dd, J=6.5 Hz, 2H), 3.95-3.89 (m, 1H), 3.26 (d, J=12.6 Hz, 1H), 3.19 (d, J=12.5 Hz, 1H), 3.07-2.97 (m, 1H), 2.88 (d, J=12.4 Hz, 1H), 2.83-2.76 (m, 1H), 2.73-2.65 (m, 1H), 2.42-2.30 (m, 1H), 0.92 (d, J=6.4 Hz, 3H).

Preparation of Intermediate E.3,
cis-2-(4-fluoropyrrolidin-3-yl)propan-2-ol, TFA Salt Scheme E

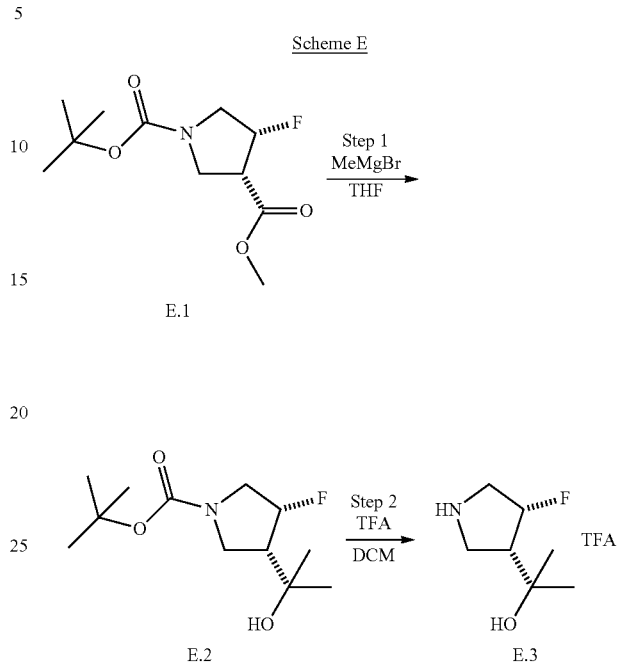

Step 1—Synthesis of E.2, cis-tert-butyl 3-fluoro-4-(2-hydroxypropan-2-yl)pyrrolidine-1-carboxylate Methylmagnesium bromide (3.37 ml, 10.11 mmol) was added dropwise over 20 min to a solution of racemic-cis-1-tert-butyl 3-methyl 4-fluoropyrrolidine-1,3-dicarboxylate (500 mg, 2.02 mmol) in THF (15 ml) at 0° C. (ice bath). The mixture was brought to room temperature and stirred for 3 h. The mixture was quenched with saturated aqueous ammonium chloride solution (dropwise at first) (15 ml). The organic phase was separated and the aqueous phase extracted with EtOAc (2×10 mL). The organic extracts were combined, washed with water (1×10 mL) and brine (1×10 mL), dried over magnesium sulfate, and filtered and concentrated to provide cis-tert-butyl 3-fluoro-4-(2-hydroxypropan-2-yl)pyrrolidine-1-carboxylate. This material was used as is without further purification.

Step 2—Synthesis of E.3,
cis-2-(4-fluoropyrrolidin-3-yl)propan-2-ol

To a solution of cis-tert-butyl 3-fluoro-4-(2-hydroxypropan-2-yl)pyrrolidine-1-carboxylate (100 mg, 0.404 mmol) in DCM (2 mL) was added TFA (0.2 mL). The mixture was stirred at room temperature for 3 hours. The reaction mixture was evaporated to dryness under a stream of N$_{2(g)}$ to provide racemic-cis-2-(4-fluoropyrrolidin-3-yl)propan-2-ol, which was used immediately in the next step. MS(ESI) m/z calc'd for C$_7$H$_{15}$FNO [M+H]$^+$ 148 found 148.

Preparation of Intermediate F.3, (2R,6S)-2,6-dimethyl-1-(oxetan-3-yl)piperazine, TFA Salt

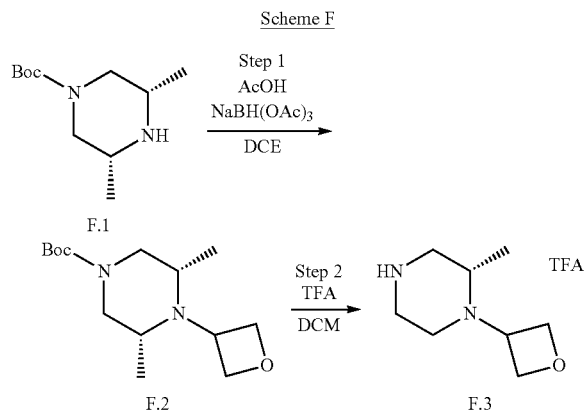

Step 1—Synthesis of F.2, tert-butyl (3R,5S)-3,5-dimethyl-4-(oxetan-3-yl)piperazine-1-carboxylate A mixture containing (3S,5R)-tert-butyl 3,5-dimethylpiperazine-1-carboxylate (500 mg, 2.33 mmol) and oxetan-3-one (0.40 g, 5.6 mmol) in dichloroethane (10 mL) was treated with acetic acid (0.20 mL, 3.5 mmol) and stirred at 50° C. for two hours, then cooled to room temperature. Sodium triacetoxyborohydride (1.0 g, 4.7 mmol) was added and the reaction mixture stirred at room temperature for 15 h. The crude reaction mixture was diluted with DCM (50 mL) and washed with water (3×50 mL). The organic layer was dried over $Na_2SO_4$, filtered and concentrated to provide tert-butyl (3R,5S)-3,5-dimethyl-4-(oxetan-3-yl)piperazine-1-carboxylate.

Step 2—Synthesis of F.3, (2R,6S)-2,6-dimethyl-1-(oxetan-3-yl)piperazine, TFA Salt A mixture containing (3S,5R)-tert-butyl 3,5-dimethyl-4-(oxetan-3-yl)piperazine-1-carboxylate (225 mg, 0.832 mmol) in dichloromethane (3 mL) was treated with trifluoroacetic acid (1 mL), and the solution was aged 2 hours and concentrated to provide (2R,6S)-2,6-dimethyl-1-(oxetan-3-yl)piperazine as a TFA salt. $^1$H NMR (400 MHz, DMSO-$d_6$) 9.03 (br, 2H), 4.67 (m, 2H), 4.58 (m, 2H), 4.32 (m, 1H), 3.20 (m, 2H), 2.88-3.27 (br m, 4H), 1.03 (d, 6H, J=8.0 Hz).

Preparation of Intermediate G.3, (S)-3-(difluoromethyl)pyrrolidine, Hydrochloride Salt

Scheme G

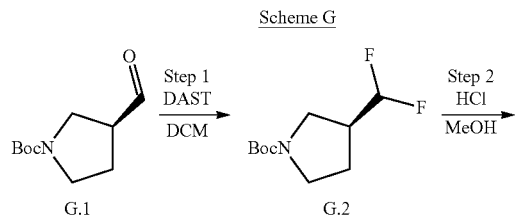

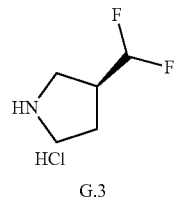

Step 1—Synthesis of G.2, tert-butyl (S)-3-(difluoromethyl)pyrrolidine-1-carboxylate To a solution of (S)-tert-butyl 3-formylpyrrolidine-1-carboxylate (200 mg, 1.00 mmol) in anhydrous DCM (2 mL) was added DAST (0.4 mL, 3 mmol), and the resulting mixture was stirred at 0° C. under $N_{2(g)}$ for 1 h. The reaction mixture was poured into water (5 mL) and extracted with DCM (3×10 mL), dried over $Na_2SO_4$, filtered and concentrated. The crude product was purified by prep-TLC (EtOAc/Hexane) to provide (S)-tert-butyl 3-(difluoromethyl)pyrrolidine-1-carboxylate.

Step 2—Synthesis of G.3, (S)-3-(difluoromethyl)pyrrolidine, Hydrochloride Salt To a solution of (S)-tert-butyl 3-(difluoromethyl)pyrrolidine-1-carboxylate (150 mg, 0.678 mmol) in anhydrous MeOH (1 mL) was added HCl (4 M in MeOH, 1 mL), and the resulting mixture was stirred at 30° C. for 2 h. The reaction was concentrated to provide (S)-3-(difluoromethyl)pyrrolidine which was used without further purification. MS(ESI) m/z calc'd for $C_5H_{15}F_2N$ [M+H]$^+$ 122 found 122.

Preparation of Intermediate H.4, 2-(3-methoxypyrrolidin-3-yl)propan-2-ol, TFA Salt

Scheme H

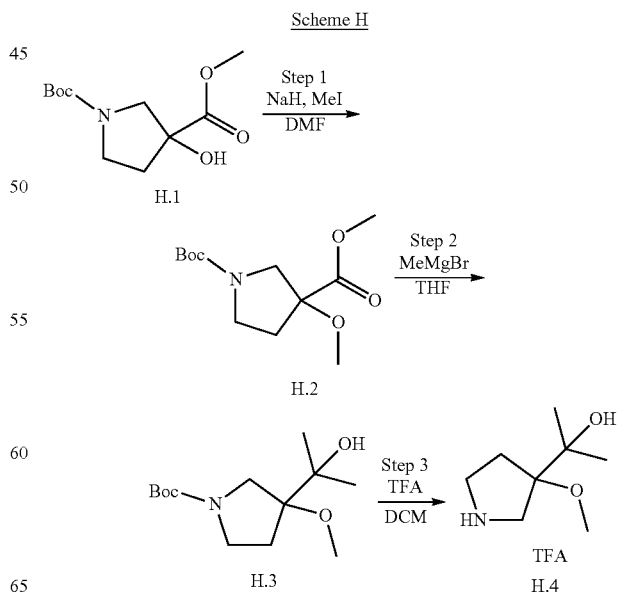

Step 1—Synthesis of Intermediate H.2, 1-(tert-butyl) 3-methyl 3-methoxypyrrolidine-1,3-dicarboxylate To a solution of 1-(tert-butyl) 3-methyl 3-hydroxypyrrolidine-1,3-dicarboxylate (250 mg, 1.02 mmol) in DMF (5 mL) was added NaH (81.53 mg, 2.04 mmol) at 0° C. The reaction was stirred for 10 min, and methyl iodide (434 mg, 3.06 mmol) was added. The resulting mixture was stirred at 28° C. for 3 h. The mixture was poured into water (20 mL) and extracted with EtOAc (3×30 mL). The organic layer was washed with brine (3×20 mL), dried over $Na_2SO_4$, filtered and concentrated to provide 1-(tert-butyl) 3-methyl 3-methoxypyrrolidine-1,3-dicarboxylate which was used without purification.

Step 2—Synthesis of Intermediate H.3, tert-butyl 3-(2-hydroxypropan-2-yl)-3-methoxypyrrolidine-1-carboxylate To a solution of 1-(tert-butyl) 3-methyl 3-methoxypyrrolidine-1,3-dicarboxylate (235 mg, 0.906 mmol) in anhydrous THF (10 mL) was added MeMgBr (0.906 mL, 2.72 mmol) dropwise at 0° C. The resulting mixture was stirred at 0° C. for 1 h. The reaction mixture was poured into water (10 mL) and extracted with EtOAc (3×30 mL). The organic layer was washed with brine (3×10 mL), dried over $Na_2SO_4$, filtered and concentrated to provide tert-butyl 3-(2-hydroxypropan-2-yl)-3-methoxypyrrolidine-1-carboxylate which was used in the next step without purification.

Step 3—Synthesis of Intermediate H.4, 2-(3-methoxypyrrolidin-3-yl)propan-2-ol, TFA Salt To a solution of tert-butyl 3-(2-hydroxypropan-2-yl)-3-methoxypyrrolidine-1-carboxylate (205 mg, 0.790 mmol) in anhydrous DCM (3 mL) was added to TFA (1 mL), the resulting mixture was stirred at 27° C. for 2 h. The reaction mixture was concentrated to provide 2-(3-methoxypyrrolidin-3-yl)propan-2-ol, TFA salt which was used without purification. MS(ESI) m/z calc'd for $C_8H_{18}NO_2$ $[M+H]^+$ 160 found 160.

Preparation of Intermediate I.3, 6-methyl-2-azaspiro[3.3]heptan-6-ol, HCl Salt

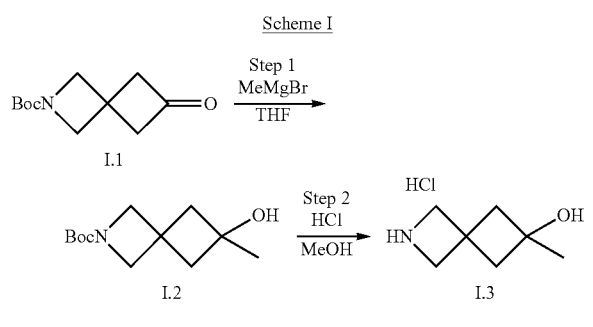

Scheme I

Step 1—Synthesis of Intermediate I.2, tert-butyl 6-hydroxy-6-methyl-2-azaspiro[3.3]heptane-2-carboxylate To a solution of tert-butyl 6-oxo-2-azaspiro[3.3]heptane-2-carboxylate (200 mg, 946 µmol) in anhydrous THF (3 mL) at 0° C. was added MeMgBr (3 M in ether, 1.3 mL, 3.9 mmol), and the resulting mixture was stirred at 0° C. for 2 h. The reaction mixture was poured into water (10 mL) and extracted with EtOAc (3×10 mL), dried over $Na_2SO_4$, filtered and concentrated to provide tert-butyl 6-hydroxy-6-methyl-2-azaspiro[3.3]heptane-2-carboxylate which was used in the next step directly without further purification.

Step 2—Synthesis of Intermediate I.3, 6-methyl-2-azaspiro[3.3]heptan-6-ol, HCl Salt To a solution of tert-butyl 6-hydroxy-6-methyl-2-azaspiro[3.3]heptane-2-carboxylate (150 mg, 659 µmol) in anhydrous MeOH (2 mL) was added HCl (4 M in MeOH, 2 mL), and the mixture was stirred at 30° C. for 2 h. The reaction was concentrated to afford 6-methyl-2-azaspiro[3.3]heptan-6-ol, HCl Salt which was used in the next step directly without further purification. MS(ESI) m/z calc'd for $C_7H_{14}NO$ $[M+H]^+$ 128 found 128.

Preparation of intermediate J.4, 2-(2-methylpyrrolidin-3-yl)propan-2-ol, TFA Salt

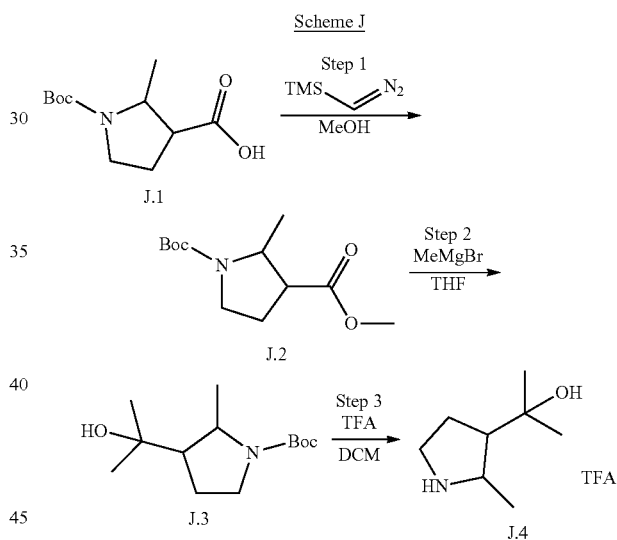

Scheme J

Step 1—Synthesis of Intermediate J.2, 1-(tert-butyl) 3-methyl 2-methylpyrrolidine-1,3-dicarboxylate To a solution of 1-(tert-butoxycarbonyl)-2-methylpyrrolidine-3-carboxylic acid (500 mg, 2.18 mmol) in anhydrous MeOH (10 mL) was added (Trimethylsilyl)diazomethane (1.64 mL, 3.27 mmol) drop wise, and the resulting mixture was stirred at 27° C. for 1 h. The reaction mixture was concentrated to provide 1-(tert-butyl) 3-methyl 2-methylpyrrolidine-1,3-dicarboxylate which was used without further purification.

Step 2—Synthesis of Intermediate J.3, tert-butyl 3-(2-hydroxypropan-2-yl)-2-methylpyrrolidine-1-carboxylate To a solution of tert-butyl 1-(tert-butyl) 3-methyl 2-methylpyrrolidine-1,3-dicarboxylate (500 mg, 2.06 mmol) in anhydrous THF (10 mL) was added MeMgBr (2.06 mL, 6.17 mmol) drop wise at 0° C. and the resulting mixture was stirred at 0° C. for 1 hour. The reaction mixture was poured into water (10 mL) and extracted with EtOAc (3×30 mL). The organic layer was washed with brine (3×10 mL), dried over Na$_2$SO$_4$, filtered and concentrated. The residue was purified by silica gel chromatography (gradient elution: 0-30% EtOAc/petroleum ether) to provide tert-butyl 3-(2-hydroxypropan-2-yl)-2-methylpyrrolidine-1-carboxylate.

Step 3—Synthesis of Intermediate J.4, 2-(2-methylpyrrolidin-3-yl)propan-2-ol, TFA Salt To a solution of tert-butyl 3-(2-hydroxypropan-2-yl)-2-methylpyrrolidine-1-carboxylate (350 mg, 1.44 mmol) in anhydrous DCM (3 mL) was added to TFA (1 mL). The resulting mixture was stirred at 27° C. for 2 h. The reaction mixture was concentrated to give 2-(2-methylpyrrolidin-3-yl)propan-2-ol, TFA salt which was used without further purification. MS(ESI) m/z calc'd for C$_8$H$_{18}$NO [M+H]$^+$ 144 found 144.

Preparation of intermediate K.5, 2-(4-methylpyrrolidin-3-yl)propan-2-ol

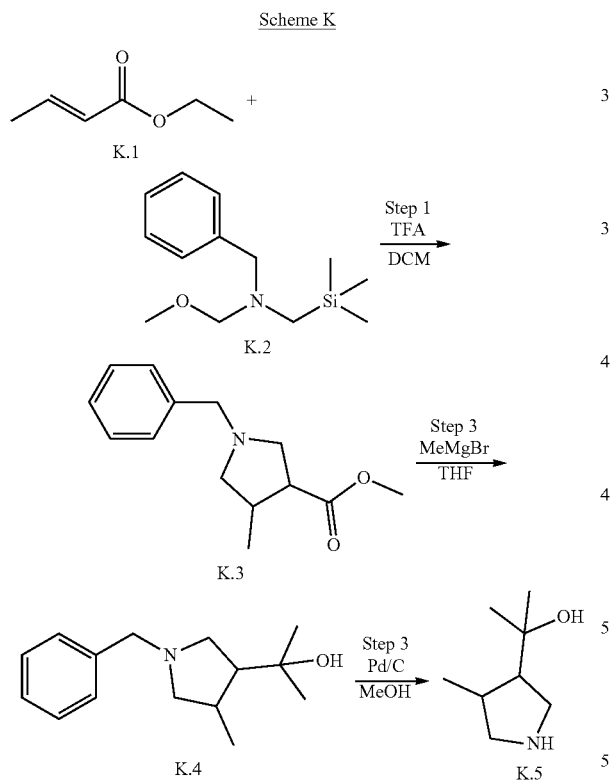

Step 1—Synthesis of Intermediate K.3, methyl 1-benzyl-4-methylpyrrolidine-3-carboxylate To a mixture of ethyl (E)-but-2-enoate (1.0 g, 8.8 mmol) and N-benzyl-1-methoxy-N-((trimethylsilyl)methyl)methanamine (3.12 g, 13.1 mmol) in anhydrous DCM (15 mL) was added TFA (100 mg, 0.876 mmol), and the resulting mixture was stirred at 28° C. for 16 hours. The reaction mixture was concentrated and the residue was purified by silica gel chromatography (gradient elution: 0-25% EtOAc/petroleum ether) to give methyl 1-benzyl-4-methylpyrrolidine-3-carboxylate.

Step 2—Synthesis of Intermediate K.4, 2-(1-benzyl-4-methylpyrrolidin-3-yl)propan-2-ol To a solution of methyl 1-benzyl-4-methylpyrrolidine-3-carboxylate (700 mg, 2.83 mmol) in anhydrous THF (10 mL) was added MeMgBr (3 M in ether, 2.83 mL, 8.49 mmol) drop wise at 0° C., and the resulting mixture was stirred at 0° C. for 1 hour. The reaction mixture was poured into water (10 mL) and extracted with EtOAc (3×30 mL). The organic layer was washed with brine (3×10 mL), dried over Na$_2$SO$_4$, filtered and concentrated. The residue was purified by silica gel chromatography (gradient elution: 0-25% EtOAc/petroleum ether) to give 2-(1-benzyl-4-methylpyrrolidin-3-yl)propan-2-ol.

Step 3—Synthesis of Intermediate K.5, 2-(4-methylpyrrolidin-3-yl)propan-2-ol

To a solution of 2-(1-benzyl-4-methylpyrrolidin-3-yl)propan-2-ol (520 mg, 2.23 mmol) in MeOH (10 mL) was added Pd—C (52.9 mg, 0.445 mmol) under N$_2$ protection. The mixture was evacuated and backfilled with H$_{2(g)}$ (3×) and then the solution was stirred under 15 psi at 28° C. for 4 h. The suspension was filtered through a pad of Celite® (diatomaceous earth) and the pad was washed with MeOH (3×15 mL). The filtrate was concentrated to provide 2-(4-methylpyrrolidin-3-yl)propan-2-ol which was used without further purification. MS(ESI) m/z calc'd for C$_8$H$_{18}$NO [M+H]$^+$ 144 found 144.

Preparation of intermediate L.3, (R)-2-(1-(6-chloropyrimidin-4-yl)pyrrolidin-3-yl)propan-2-ol

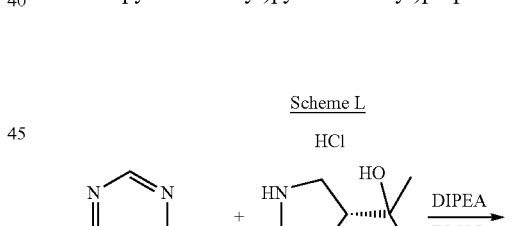

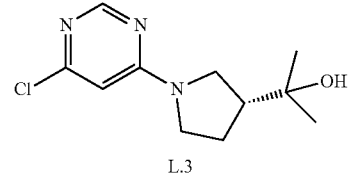

4,6-dichloropyrimidine (1.49 g, 10.0 mmol) was suspended in DMSO (15 mL). (R)-2-(pyrrolidin-3-yl)propan-2-ol hydrochloride (1.82 g, 11.0 mmol) and DIPEA (4.37 ml, 25.0 mmol) were added and then heated to 90° C. overnight. The reaction was cooled to room temperature, ethyl acetate (100 mL) was added and the reaction was filtered. The filtrate was washed with water (3×50 mL), dried over sodium sulfate, filtered and concentrated. The crude material was purified by silica gel column chromatography [gradient elution: 15-60% (3:1 EtOAc:EtOH)/hexanes] to provide (R)-2-(1-(6-chloropyrimidin-4-yl)pyrrolidin-3-yl)propan-2-ol. MS (ESI) m/z calc'd for $C_{11}H_{17}ClN_3O$ [M+H]$^+$ 242 found 24.

Compounds in Table 1 were prepared according to General Scheme 3 and Scheme L above. In general the products can be purified by silica gel chromatography, reverse phase prep-HPLC, precipitation, SFC, or used without purification after a typical workup.

TABLE 1

Intermediates According to General Scheme 3 and Scheme L

| Entry | Structure Name | Observed m/z [M + H]$^+$ |
|---|---|---|
| L.4 | 4-chloro-6-((3S,5R)-3,5-dimethyl-4-(oxetan-3-yl)piperazin-1-yl)pyrimidine | 283 |
| L.5 | 2-(2-(6-chloropyrimidin-4-yl)-2-azabicyclo[2.1.1]hexan-4-yl)propan-2-ol | 254 |
| L.6 | (S)-4-chloro-6-(3-methyl-4-(oxetan-3-yl)piperazin-1-yl)pyrimidine | 269 |
| L.7 | (R)-4-chloro-6-(3-methyl-4-(oxetan-3-yl)piperazin-1-yl)pyrimidine | 269 |

TABLE 1-continued

Intermediates According to General Scheme 3 and Scheme L

| Entry | Structure<br>Name | Observed m/z<br>[M + H]⁺ |
|---|---|---|
| L.8 | (3S,4s,5R)-1-(6-chloropyrimidin-4-yl)-3,4,5-trimethylpiperidin-4-ol | 256 |
| L.9 | 1-(6-chloropyrimidin-4-yl)-3-methylazetidin-3-ol | 200 |
| L.10 | racemic-2-(4-(6-chloropyrimidin-4-yl)morpholin-2-yl)propan-2-ol | 258 |
| L.11 | 2-(1-(6-chloropyrimidin-4-yl)azetidin-3-yl)propan-2-ol | 228 |
| L.12 | 4-chloro-6-(3-methoxyazetidin-1-yl)-2-(methoxymethyl)pyrimidine | 244 |

TABLE 1-continued

Intermediates According to General Scheme 3 and Scheme L

| Entry | Structure Name | Observed m/z [M + H]+ |
|---|---|---|
| L.13 | 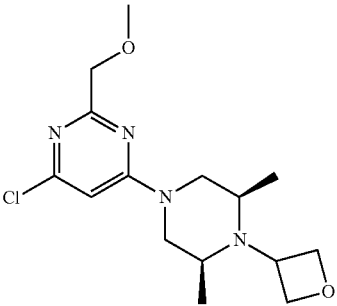<br>4-chloro-6-((3S,5R)-3,5-dimethyl-4-(oxetan-3-yl)piperazin-1-yl)-2-(methoxymethyl)pyrimidine | 327 |
| L.14 | 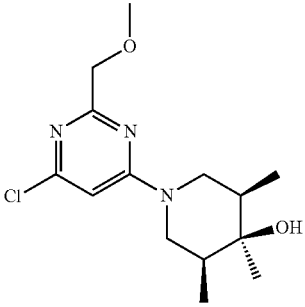<br>(3S,4s,5R)-1-(6-chloro-2-(methoxymethyl)pyrimidin-4-yl)-3,4,5-trimethylpiperidin-4-ol | 300 |
| L.15 | 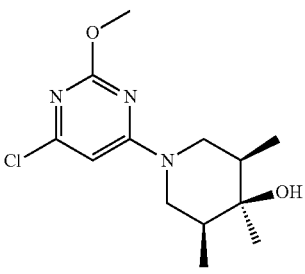<br>(3S,4s,5R)-1-(6-chloro-2-methoxypyrimidin-4-yl)-3,4,5-trimethylpiperidin-4-ol | 286 |
| L.16 | 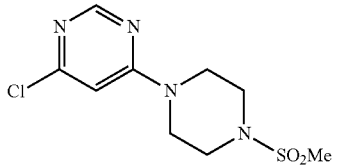<br>4-chloro-6-(4-(methylsulfonyl)piperazin-1-yl)pyrimidine | 277 |
| L.17 | 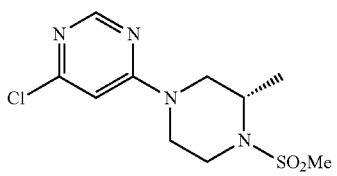<br>(S)-4-chloro-6-(3-methyl-4-(methylsulfonyl)piperazin-1-yl)pyrimidine | 291 |

TABLE 1-continued

Intermediates According to General Scheme 3 and Scheme L

| Entry | Structure Name | Observed m/z [M + H]+ |
|---|---|---|
| L.18 | 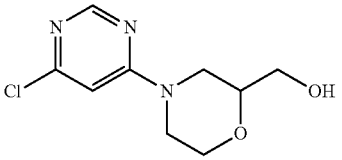 racemic-(4-(6-chloropyrimidin-4-yl)morpholin-2-yl)methanol | 230 |
| L.19 | 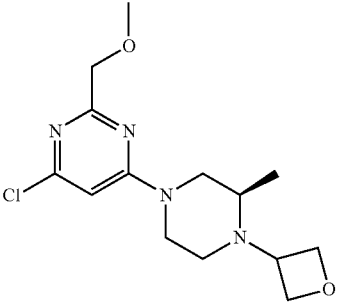 (R)-4-chloro-2-(methoxymethyl)-6-(3-methyl-4-(oxetan-3-yl)piperazin-1-yl)pyrimidine | 313 |
| L.20 | 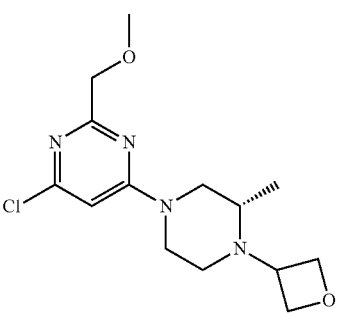 (S)-4-chloro-2-(methoxymethyl)-6-(3-methyl-4-(oxetan-3-yl)piperazin-1-yl)pyrimidine | 313 |
| L.21 | 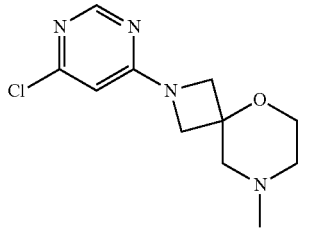 2-(6-chloropyrimidin-4-yl)-8-methyl-5-oxa-2,8-diazaspiro[3.5]nonane | 255 |
| L.22 | 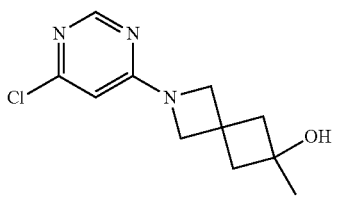 2-(6-chloropyrimidin-4-yl)-6-methyl-2-azaspiro[3.3]heptan-6-ol | 240 |

TABLE 1-continued

Intermediates According to General Scheme 3 and Scheme L

| Entry | Structure Name | Observed m/z [M + H]+ |
|---|---|---|
| L.23 | 4-chloro-2-methyl-6-(4-(3-methyloxetan-3-yl)piperazin-1-yl)pyrimidine | 283 |
| L.24 | (S)-8-(6-chloro-2-methylpyrimidin-4-yl)octahydropyrazino[2,1-c][1,4]oxazine | 269 |

Preparation of Intermediate M.1-1 to M.1-4, 2-((2S or 2R, 3R or 3S)-1-(6-chloropyrimidin-4-yl)-2-methylpyrrolidin-3-yl)propan-2-ol Scheme M

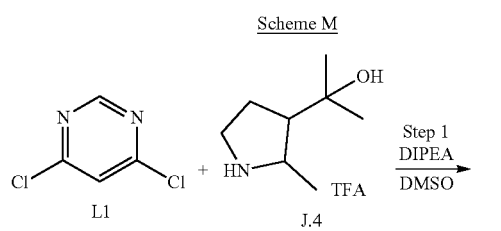

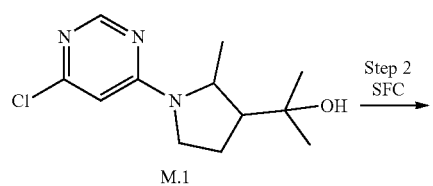

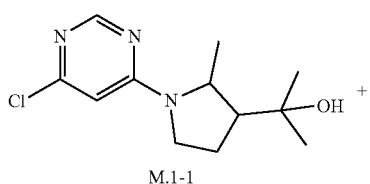

-continued

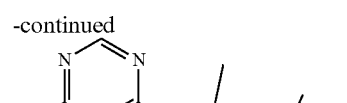
M.1-2

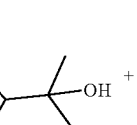
+

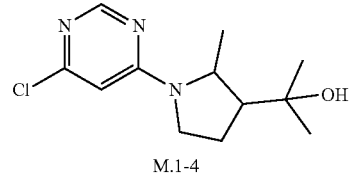
M.1-3

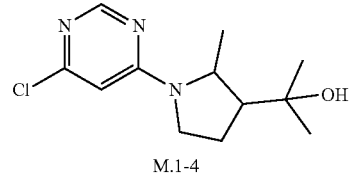
M.1-4

Step 1—Synthesis of Intermediate M.1, 2-(1-(6-chloropyrimidin-4-yl)-2-methylpyrrolidin-3-yl)propan-2-ol (Mixture of 4 Isomers)

To a solution of 4,6-dichloropyrimidine in IPA (10 mL) was added 2-(2-methylpyrrolidin-3-yl)propan-2-ol, TFA salt (J.4) (197 mg, 1.32 mmol) and DIPEA (512 mg, 3.96 mmol). The resulting mixture was stirred at 90° C. for 3 hours. The reaction mixture was poured into water (20 mL) and extracted with EtOAc (3×40 mL). The organic layer was washed with brine (3×20 mL), dried over Na₂SO₄, filtered and concentrated. The residue was purified by silica gel chromatography (gradient elution: 0-30% EtOAc/petroleum ether) to give 2-(1-(6-chloropyrimidin-4-yl)-2-methylpyrrolidin-3-yl)propan-2-ol as a mixture of 4 stereoisomers.

Step 2-Resolution of Isomers

The crude racemic 2-(1-(6-chloropyrimidin-4-yl)-2-methylpyrrolidin-3-yl)propan-2-ol (300 mg, 1.08 mmol) was purified by CHIRAL-Prep-SFC [Column: CHIRALPAK AD, 3×25 cm (10 μm); 30% EtOH/CO$_2$; Flow rate: 60 mL/min; 220 nm; RT1:3.77 min (M.1-1); RT2: 5.00 min (M.1-2); RT3:5.64 min (M.1-3); RT4: 5.80 min (M.1-4)].

M.1-1:
RT: 3.77 min. MS(ESI) m/z calc'd for $C_{12}H_{19}ClN_3O$ [M+H]$^+$ 256 found 256.
M.1-2:
RT: 5.00 min. MS(ESI) m/z calc'd for $C_{12}H_{19}ClN_3O$ [M+H]$^+$ 256 found 256.
M.1-3:
RT: 5.64 min. MS(ESI) m/z calc'd for $C_{12}H_{19}ClN_3O$ [M+H]$^+$ 256 found 256.
M.1-3:
RT: 5.80 min. MS(ESI) m/z calc'd for $C_{12}H_{19}ClN_3O$ [M+H]$^+$ 256 found 256.

Compounds in Table 2 were prepared according to General Scheme 3 and Scheme M

TABLE 2

Compounds Prepared According to General Scheme 3 and Scheme M

| Entry | Structure Name | Observed m/z [M + H]$^+$ |
|---|---|---|
| M.2-1 | 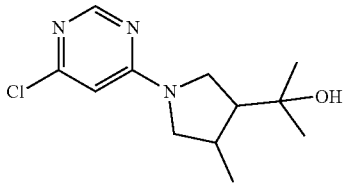<br>2-((3R or 3S,4R or 4S)-1-(6-chloropyrimidin-4-yl)-4-methylpyrrolidin-3-yl)propan-2-ol | 256 |
| M.2-2 | 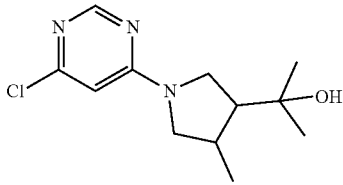<br>2-((3R or 3S,4R or 4S)-1-(6-chloropyrimidin-4-yl)-4-methylpyrrolidin-3-yl)propan-2-ol | 256 |
| M.3-1 | 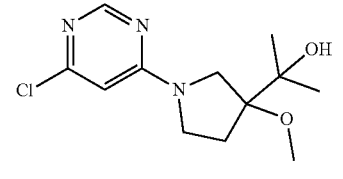<br>(R or S)-2-(1-(6-chloropyrimidin-4-yl)-3-methoxypyrrolidin-3-yl)propan-2-ol | 272 |
| M.3-2 | 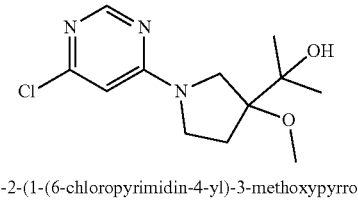<br>(R or S)-2-(1-(6-chloropyrimidin-4-yl)-3-methoxypyrrolidin-3-yl)propan-2-ol | 272 |

TABLE 2-continued

Compounds Prepared According to General Scheme 3 and Scheme M

| Entry | Structure Name | Observed m/z [M + H]+ |
|---|---|---|
| M.4-1 | 2-((3(S or R),4(R or S))-1-(6-chloropyrimidin-4-yl)-4-fluoropyrrolidin-3-yl)propan-2-ol | 260 |
| M.4-2 | 2-((3(S or R),4(R or S))-1-(6-chloropyrimidin-4-yl)-4-fluoropyrrolidin-3-yl)propan-2-ol | 260 |
| M.5-1 | (4aS,7aR or 4aR,7aS)-6-(6-chloro-2-methylpyrimidin-4-yl)-4-methyloctahydropyrrolo[3,4-b][1,4]oxazine | 268 |
| M.5-1 | (4aS,7aR or 4aR,7aS)-6-(6-chloro-2-methylpyrimidin-4-yl)-4-methyloctahydropyrrolo[3,4-b][1,4]oxazine | 268 |

M.2-1/M.2-2

The crude racemic 2-(1-(6-chloropyrimidin-4-yl)-4-methylpyrrolidin-3-yl)propan-2-ol was resolved by CHIRAL-Prep-SFC [Column: CHIRALPAK C2, 3×25 cm (10 μm); 35% EtOH/CO$_2$; Flow rate: 60 mL/min; 220 nm; RT1: 4.64 min (M.2-1); RT2:4.98 min (M.2-2)]

M.3-1/M.3-2:

The crude racemic 2-(1-(6-chloropyrimidin-4-yl)-3-methoxypyrrolidin-3-yl)propan-2-ol was resolved by CHIRAL-Prep-SFC [Column: CHIRALPAK AS-H, 3×25 cm (10 μm); 25% IPA/C$_2$; Flow rate: 60 mL/min; 220 nm; RT1: 2.74 min (M.3-1); RT2: 3.22 min (M.3-2)]

M.4-1/M.4-2:

The crude cis-2-(1-(6-chloropyrimidin-4-yl)-4-fluoropyrrolidin-3-yl)propan-2-ol was resolved by CHIRAL-Prep-SFC [Column: CHIRALPAK AD-H, 4.6×250 mm (10 μm); 45% EtOH/CO$_2$; Flow rate: 50 mL/min; 210 nm; RT1: 2.91 min (M.4-1); RT2: 3.56 min (M.4-2)]

M.5-1/M.5-2:

The crude 4aS,7aR or 4aR,7aS)-6-(6-chloro-2-methylpyrimidin-4-yl)-4-methyloctahydropyrrolo[3,4-b][1,4]oxazine was resolved by CHIRAL-Prep-SFC [Column: CCA 21×250 mm; 15% MeOH/CO$_2$; Flow rate: 70 mL/min; 210 nM; RT1: 2.5 min (M.5-1); RT2: 3.3 min (M.5-2)]

Preparation of Intermediate M.5-1 and M.5-2, (S or R)-5-(6-chloropyrimidin-4-yl)-5-azaspiro[2.4]heptan-7-ol Scheme N

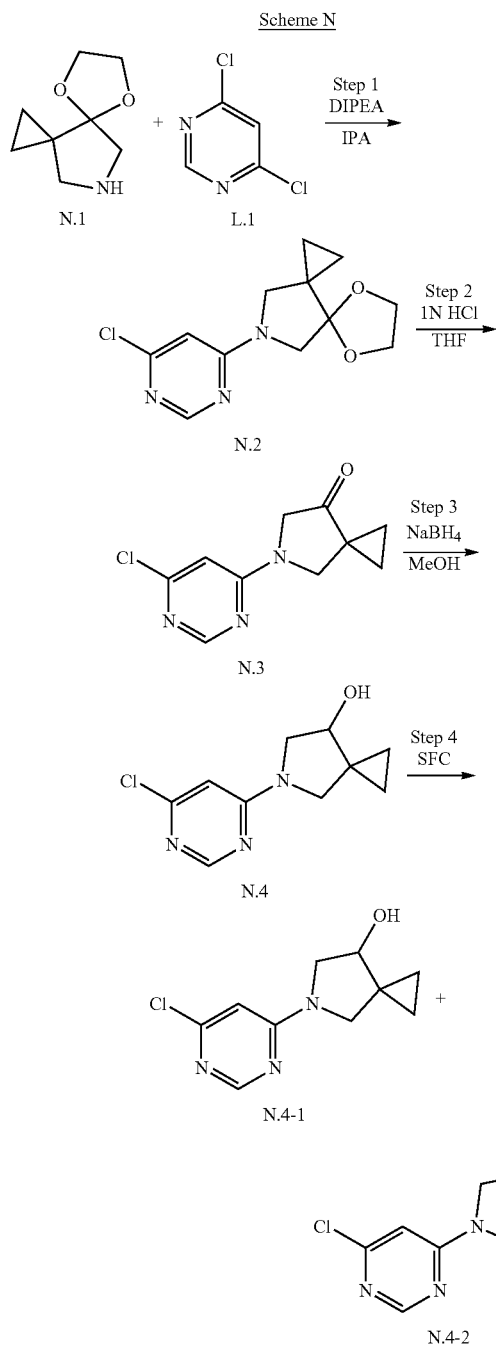

Step 1—Synthesis of Intermediate N.2, 10-(6-chloropyrimidin-4-yl)-5,8-dioxa-10-azadispiro[2.0.4⁴.3³]undecane To a solution of 4,6-dichloropyrimidine (200 mg, 1.29 mmol) in IPA (10 mL) was added 5,8-dioxa-10-azadispiro[2.0.4⁴.3³]undecane (192 mg, 1.29 mmol) and DIPEA (500 mg, 3.87 mmol). The resulting mixture was stirred at 90° C. for 3 hours. The reaction mixture was poured into water (20 mL) and extracted with EtOAc (3×40 mL). The organic layer was washed with brine (3×20 m), dried over Na₂SO₄, filtered and concentrated to provide 10-(6-chloropyrimidin-4-yl)-5,8-dioxa-10-azadispiro[2.0.4⁴.3³] which was used without further purification.

Step 2—Synthesis of Intermediate N.3, 5-(6-chloropyrimidin-4-yl)-5-azaspiro[2.4]heptan-7-one To a solution of 10-(6-chloropyrimidin-4-yl)-5,8-dioxa-10-azadispiro[2.0.4⁴.3³]undecane (310 mg, 1.16 mmol) in THF (5 mL) was added 1N HCl (2 mL). The resulting mixture was stirred at 70° C. for 2 h. The reaction mixture was poured into saturated aqueous NaHCO₃ (15 mL) and extracted with EtOAc (3×30 mL). The organic layer was washed with brine (3×20 mL), dried over Na₂SO₄, filtered and concentrated to provide 5-(6-chloropyrimidin-4-yl)-5-azaspiro[2.4]heptan-7-one which was used without further purification.

Step 3—Synthesis of Intermediate N.4, 5-(6-chloropyrimidin-4-yl)-5-azaspiro[2.4]heptan-7-ol To a solution of 5-(6-chloropyrimidin-4-yl)-5-azaspiro[2.4]heptan-7-one (230 mg, 1.03 mmol) in anhydrous MeOH (5 mL) and DCM (5 mL) was added NaBH₄ (2.06 mmol, 77.81 mg). The resulting mixture was stirred at 28° C. under N₂(g) for 2 h. The reaction mixture was poured into water (20 mL) and extracted with EtOAc (3×30 mL). The organic layer was washed with brine (3×10 m), dried over Na₂SO₄, filtered and concentrated. The residue was purified by silica gel chromatography (gradient elution: 0-48% EtOAc/PE) to provide 5-(6-chloropyrimidin-4-yl)-5-azaspiro[2.4]heptan-7-ol.

Step 4—Resolution of Intermediate N.4

Racemic 5-(6-chloropyrimidin-4-yl)-5-azaspiro[2.4]heptan-7-ol was resolved by CHIRAL-Prep-SFC [Column: CHIRALPAK IC, 3×25 cm (10 μm); 40% IPA/CO₂; Flow rate: 80 mL/min; 220 nm; RT1:3.59 min (N.5-1); RT2: 3.95 min (N.5-2)].

N.4-1

RT: 3.59 min. MS(ESI) m/z calc'd for C₁₀H₁₃ClN₃O [M+H]⁺ 226 found 226.

N.4-2

RT: 3.95 min. MS(ESI) m/z calc'd for C₁₀H₁₃ClN₃O [M+H]⁺ 226 found 226.

Preparation of Intermediate O.5-1 and 0.5-2, 4-choro-6-((R)-3-methyl-4-((S or R)-tetrahydrofuran-3-yl)piperazin-1-yl)pyrimidine Scheme O

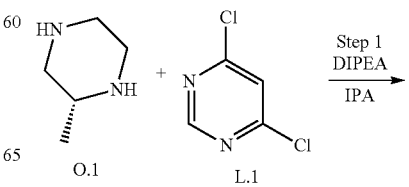

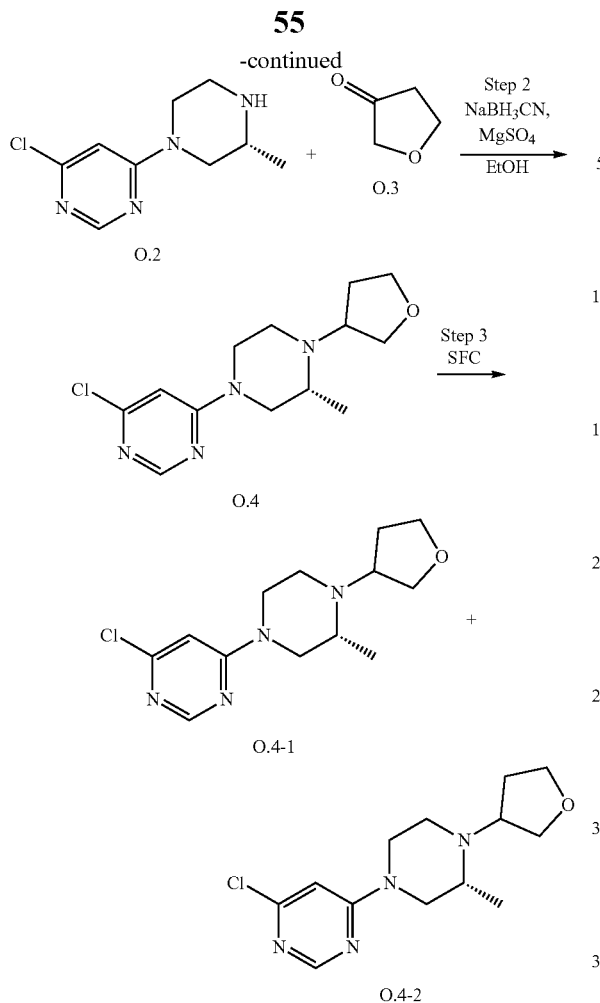

vide racemic-4-chloro-6-((3R)-3-methyl-4-(tetrahydrofuran-3-yl)piperazin-1-yl)pyrimidine.

Step 3-Resolution of Intermediate O.4

Racemic 4-chloro-6-((3R)-3-methyl-4-(tetrahydrofuran-3-yl)piperazin-1-yl)pyrimidine was purified by CHIRAL-Prep-SFC [Column: CHIRALPAK AD, 3×25 cm (10 μm); 25% EtOH/$CO_2$; Flow rate: 50 mL/min; 220 nm; RT1:4.11 (0.5-1) min; RT2: 4.37 min (0.5-2)].

O.4-1

RT: 4.11 min. MS(ESI) m/z calc'd for $C_{13}H_{20}ClN_4O$ [M+H]$^+$ 283 found 28.

O.4-2

RT: 4.37 min. MS(ESI) m/z calc'd for $C_{13}H_{20}ClN_4O$ [M+H]$^+$ 283 found 283.

TABLE 3

Compound Prepared According to Scheme O

| Entry | Structure Name | Observed m/z [M + H]$^+$ |
|---|---|---|
| O.5-1 | 4-chloro-6-((S)-3-methyl-4-((R or S)-tetrahydrofuran-3-yl)piperazin-1-yl)pyrimidine | 283 |
| O.5-2 | 4-chloro-6-((S)-3-methyl-4-((R or S)-tetrahydrofuran-3-yl)piperazin-1-yl)pyrimidine | 283 |

O.5-1/O.5-2

4-chloro-6-((3S)-3-methyl-4-(tetrahydrofuran-3-yl)piperazin-1-yl)pyrimidine was resolved by CHIRAL-Prep-SFC [Column: CHIRALPAK AD, 3×25 cm (10 μm); 30% EtOH/$CO_2$; Flow rate: 50 mL/min; 220 nm; RT1:4.95 min (0.6-1); RT2: 5.28 min (0.6-2)]

Preparation of Intermediate P.2, 2-(2-(4-iodopyridin-2-yl)-2-azabicyclo[2.1.1]hexan-4-yl)propan-2-ol Step 1—Synthesis of Intermediate O.2, (R)-4-chloro-6-(3-methylpiperazin-1-yl)pyrimidine To a solution of 4,6-dichloropyrimidine (100 mg, 0.998 mmol) in IPA (5 mL) was added (R)-2-methylpiperazine (149 mg, 1 mmol) and DIPEA (387 mg, 3 mmol). The resulting mixture was stirred at 90° C. for 2 h. The reaction mixture was poured into water (20 mL) and extracted with EtOAc (3×40 mL), the organic layer was washed with brine (3×20 mL), dried over $Na_2SO_4$, filtered and concentrated to provide (R)-4-chloro-6-(3-methylpiperazin-1-yl)pyrimidine which was used without further purification.

Step 2—Synthesis of Intermediate O.4, (4-chloro-6-((3R)-3-methyl-4-(tetrahydrofuran-3-yl)piperazin-1-yl)pyrimidine To a solution of (R)-4-chloro-6-(3-methylpiperazin-1-yl)pyrimidine (170 mg, 0.849 mmol) in anhydrous EtOH (5 mL) was added dihydrofuran-3(2H)-one (219 mg, 2.55 mmol), AcOH (76 mg, 1.3 mmol), $MgSO_4$ (1.7 mmol, 204 mg) and $NaBH_3CN$ (2.55 mmol, 160.02 mg). The resulting mixture was stirred at 90° C. under $N_{2(g)}$ for 2 h. The reaction mixture was poured into water (20 mL) and extracted with EtOAc (3×30 mL). The organic layer was washed with brine (3×10 m), dried over $Na_2SO_4$, filtered and concentrated. The residue was purified by silica gel chromatography (gradient elution: 0-100% EtOAc/PE) to pro- Scheme P

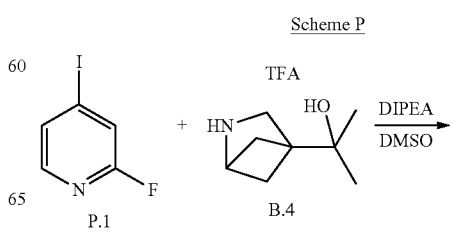

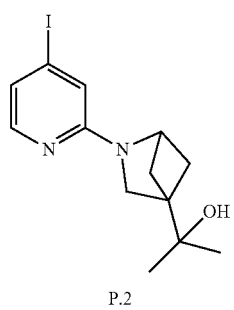

P.2

2-fluoro-4-iodopyridine (446 mg, 2.00 mmol) was suspended in DMSO (3.00 mL). 2-(2-azabicyclo[2.1.1]hexan-4-yl)propan-2-ol, TFA salt (476 mg, 2.00 mmol) and DIPEA (1.05 mL, 6.00 mmol) were added and the reaction was heated to 150° C. for 2.5 h. The reaction was cooled to room temperature, diluted with ethyl acetate (20 mL) and filtered. The filtrate was washed with water (3×20 mL), dried over sodium sulfate, filtered and evaporated. The crude material was purified by silica gel column chromatography (gradient elution: 15-60% (3:1 EtOAc:EtOH)/hexanes) to provide 2-(2-(4-iodopyridin-2-yl)-2-azabicyclo[2.1.1]hexan-4-yl)propan-2-ol. MS (ESI) m/z calc'd for $C_{13}H_{18}IN_2O$ $[M+H]^+$ 345.1 found 345.0.

Compounds in Table 4 were prepared according to general Scheme 4 and Scheme P

TABLE 4

Compounds Prepared According to General Scheme 4 and Scheme P

| Entry | Structure Name | Observed m/z [M + H]⁺ |
|---|---|---|
| P.3 | (R)-2-(1-(4-iodopyridin-2-yl)pyrrolidin-3-yl)propan-2-ol | 333 |
| P.4 | 1-(4-iodopyridin-2-yl)-4-(methylsulfonyl)piperazine | 367 |
| P.5 | 2-(2-(6-fluoro-4-iodopyridin-2-yl)-2-azabicyclo[2.1.1]hexan-4-yl)propan-2-ol | 363 |
| P.6 | (S)-4-(6-fluoro-4-iodopyridin-2-yl)-2-methyl-1-(oxetan-3-yl)piperazine | 378 |

59

TABLE 4-continued

Compounds Prepared According to General Scheme 4 and Scheme P

| Entry | Structure Name | Observed m/z [M + H]+ |
|---|---|---|
| P.7 | 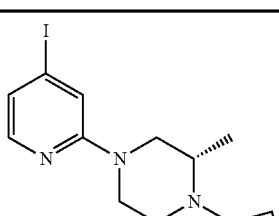<br>(S)-4-(4-iodopyridin-2-yl)-2-methyl-1-(oxetan-3-yl)piperazine | 360 |

Preparation of Intermediate Q.3, Q.3-1, Q.3-2, 1-(H-indazol-6-yl)spiro[2.2]pentane-1-carbonitrile, (R or S)-1-(H-indazol-6-yl)spiro[2.2]pentane-1-carbonitrile Scheme Q

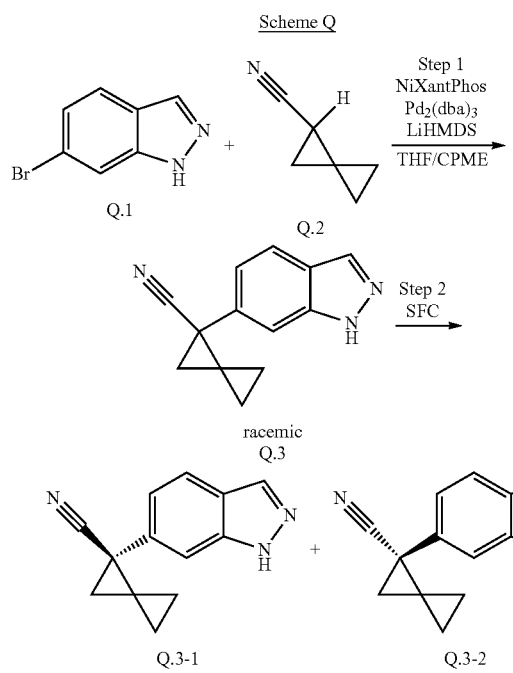

Step 1—Synthesis of Racemic Q.3, 1-(1H-indazol-6-yl)spiro[2.2]pentane-1-carbonitrile A 5000-mL 4-necked round-bottom flask was purged with nitrogen and maintained under an inert atmosphere. The vessel was charged with THF (2800 mL), and sparged with nitrogen for 10 min. Pd$_2$(dba)$_3$ (45.78 g, 50.12 mmol) and NiXantPhos (55.35 g, 100.24 mmol) were charged in the vessel, and the resulting solution was stirred for 20 min at room temperature. Another 10-L 4-necked round-bottom flask was purged with nitrogen and maintained under an inert atmosphere. The vessel was charged with CPME (2800 mL), and sparged with nitrogen for 10 min. The vessel was then charged with 6-bromo-1H-indazole (197.5 g, 1002.4 mmol) and spiro[2.2]pentane-1-carbonitrile (140 g, 1503 mmol). The resulting solution was stirred for 10 min at room temperature. The solution of catalyst was then added to the substrate solution under nitrogen, and the solution was placed in a cool water bath (~20° C.). LiHMDS (1M THF, 3000 ml, 3000 mmol) was added dropwise over 30 min under nitrogen, keeping the temperature of the solution below 25° C. The resulting solution was stirred for 2 h at 80° C. The reaction mixture was cooled to 20° C. with a water/ice bath and quenched by the addition of aqueous saturated ammonium chloride solution (10 L). The resulting solution was extracted with ethyl acetate (2×2000 mL), dried over anhydrous sodium sulfate and concentrated. The crude material was purified by silica gel column chromatography (33% EtOAc/petroleum ether) to provide 1-(1H-indazol-6-yl)spiro[2.2]pentane-1-carbonitrile.

Step 2-Resolution of 1-(1H-indazol-6-yl)spiro[2.2]pentane-1-carbonitrile

The crude racemic 1-(1H-indazol-6-yl)spiro[2.2]pentane-1-carbonitrile (152 g, 0.73 mmol) was purified by CHIRAL-Prep-SFC [Column: CHIRALPAK AD-H, 5×25 cm (5 μm); 50% MeOH/CO$_2$; Flow rate: 170 mL/min; 220 nm; RT1: 4.29 min (Q.3-1); RT2: 6.69 min (Q.3-2)].

Q.3-1, (R)-1-(1H-indazol-6-yl)spiro[2.2]pentane-1-carbonitrile

MS (ESI) m/z calc'd for C$_{13}$H$_{12}$N$_3$ [M+H]+ 210 found 210]. $^1$H NMR (400 MHz, CDCl$_3$) δ 8.08 (1H, s), 7.74-7.72 (1H, d), 7.59 (1H, s), 7.01-6.99 (1H, d), 2.31-2.29 (1H, d), 1.86-1.85 (1H, d), 1.37-1.02 (4H, m). The stereochemistry was assigned to be (R) by vibrational circular dichroism analysis (VCD).

Q.3-2, (S)-1-(1H-indazol-6-yl)spiro[2.2]pentane-1-carbonitrile

MS (ESI) m/z calc'd for C$_{13}$H$_{12}$N$_3$ [M+H]+ 210 found 210]. $^1$H NMR (400 MHz, CDCl$_3$) δ 8.08 (1H, s),7.74-7.71 (1H, d), 7.59 (1H, s), 7.01-6.98 (1H, d),2.30-2.29 (1H, d),1.86-1.85 (1H, d),1.37-1.05 (4H m). The stereochemistry was assigned to be (S) by vibrational circular dichroism analysis (VCD).

Preparation of Intermediate R.3, 1-(1H-pyrazolo[4,3-c]pyridin-6-yl)spiro[2.2]pentane-1-carbonitrilecarbonitrile

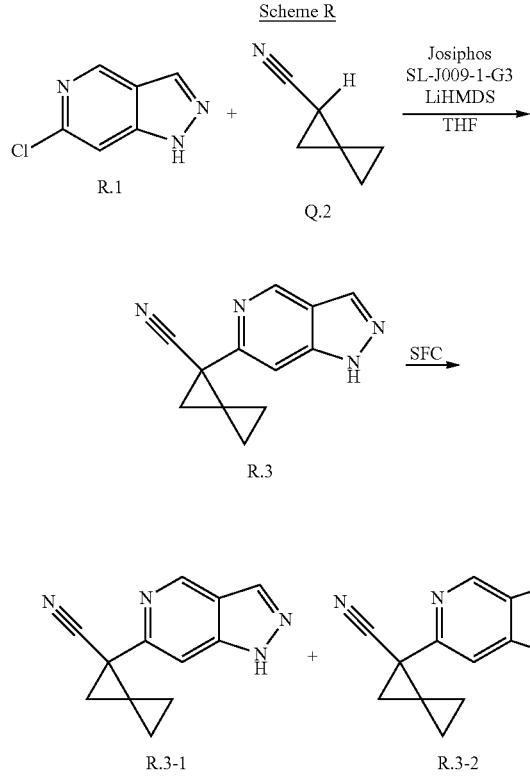

Preparation of Intermediate S.3, S.3-1 and S.3-2, 1-(4-fluoro-1H-indazol-6-yl)spiro[2.2]pentane-1-carbonitrile, (R or S)-1-(4-fluoro-1H-indazol-6-yl)spiro[2.2]pentane-1-carbonitrile

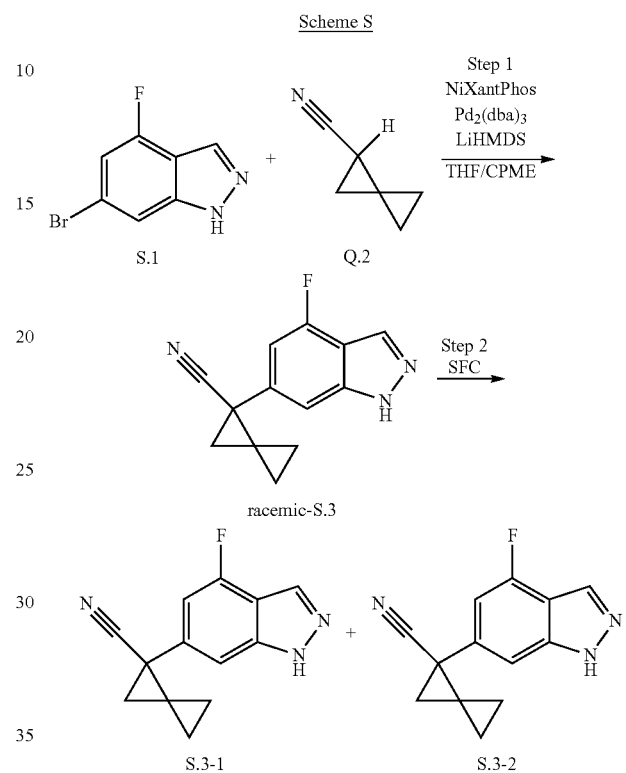

To a vessel was added 6-chloro-1H-pyrazolo[4, 3c]pyridine (500 mg, 3.26 mmol) and Josiphos SL-J009-1-G3-palladacycle (150 mg, 0.163 mmol) and the reaction was purged with argon. THF (8.14 mL) was then added and the reaction was further purged with argon. Spiro[2.2]pentane-1-carbonitrile (455 mg, 4.88 mmol) was added to the reaction followed by a dropwise addition of lithium bis(trimethylsilyl)amide (1.0M in THF, 8.140 mL, 8.14 mmol). The reaction was then heated to 80° C. for 3 hours. The reaction was then cooled, diluted with ethyl acetate (40 mL), and washed with saturated ammonium chloride (2×100 mL) and brine (1×100 mL). The organic layer was dried over anhydrous sodium sulfate, filtered and concentrated. The residue was purified by silica gel chromatography (gradient elution 0-100% EtOAc/Hexane) to afford the title compound. MS (ESI) calc'd for $C_{12}H_{11}N_4$ [M+H]$^+$: 211.1 found: 211.2 $^1$H NMR (600 MHz, DMSO-$d_6$) δ 13.39 (s, 1H), 9.02 (s, 1H), 8.26 (s, 1H), 7.40 (s, 1H), 2.25 (dd, J=23.6, 4.1 Hz, 3H), 1.14 (s, 4H).

Step 2-Resolution of 1-(1H-pyrazolo[4,3-c]pyridin-6-yl)spiro[2.2]pentane-1-carbonitrilecarbonitrile The crude racemic 1-(1H-pyrazolo[4,3-c]pyridin-6-yl)spiro[2.2]pentane-1-carbonitrilecarbonitrile was purified by CHIRAL-Prep-SFC [Column: IC, 3×15 cm; 35% EtOH/CO$_2$; Flow rate: 65 mL/min; 220 nm; RT1:3.36 min (R.3-1); RT2: 4.0 min (R.3-2)].

Step 1—Synthesis of intermediate S.3, 1-(4-fluoro-1H-indazol-6-yl)spiro[2.2]pentane-1-carbonitrile A 50-mL round-bottom flask was purged with nitrogen and maintained under an inert atmosphere. The vessel was charged with Pd$_2$(dba)$_3$ (213 mg, 0.23 mmol), NiXantPhos (257 mg, 0.46 mmol), and CPME (7 mL). The resulting solution was stirred for 10 min at room temperature. The vessel was then charged with 6-bromo-4-fluoro-1H-indazole (500 mg, 2.33 mmol), and spiro[2.2]pentane-1-carbonitrile (325 mg, 3.49 mmol). The resulting solution was stirred for 5 min at room temperature. LiHMDS (1.5 M in THF, 4.65 ml, 6.98 mmol) was added dropwise over 5 min under nitrogen. The resulting solution was stirred for 4 h at 50° C. The reaction mixture was cooled to 23° C., and quenched by the addition of aqueous saturated ammonium chloride solution (20 mL). The resulting solution was extracted with ethyl acetate (3×20 mL), dried over anhydrous sodium sulfate, filtered and concentrated. The crude material was purified by silica gel column chromatography (gradient elution: 0-100% (3:1 EtOAc:EtOH)/hexanes) to provide racemic 1-(4-fluoro-1H-indazol-6-yl)spiro[2.2]pentane-1-carbonitrile, MS (ESI) m/z calc'd for $C_{13}H_{11}FN_3$ [M+H]$^+$ 228.1 found 228.2].

Step 2-Resolution of S.3

The racemic 1-(4-fluoro-1H-indazol-6-yl)spiro[2.2]pentane-1-carbonitrile (500 mg, 2.33 mmol) was purified by CHIRAL-Prep-SFC [Column: IGx, 21×250 mm; 25% (MeOH/0.25% DMEA)/CO$_2$; Flow rate: 70 mL/min; 254 nm. RT1:2.5 min (S.3-1); RT2: 3.8 min S.3-2)].

Preparation of Intermediate T.3, 1-(5-fluoro-1H-indazol-6-yl)spiro[2.2]pentane-1-carbonitrile Scheme T

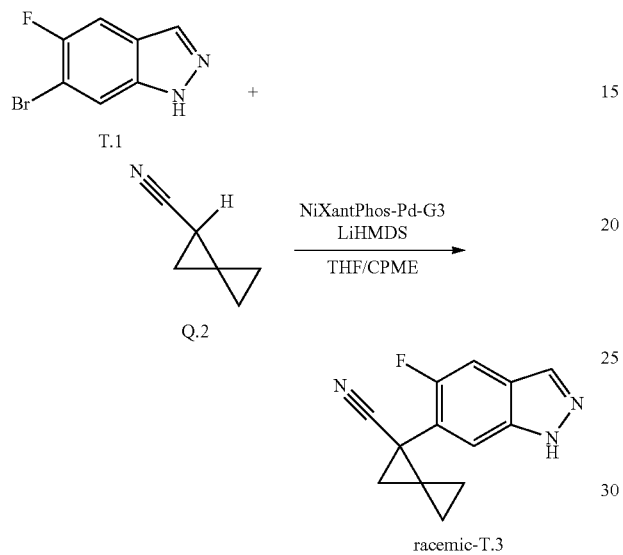

racemic-T.3

NiXantPhos-Pd-G3 (48.2 mg, 0.0520 mmol) and 6-bromo-5-fluoro-1H-indazole (225 mg, 1.05 mmol) were charged in a vessel and the vessel was evacuated and backfilled with argon (3×). THF (2.6 mL) was added and the reaction was stirred for 5 min at room temperature. A solution of spiro[2.2]pentane-1-carbonitrile (146 mg, 1.57 mmol)) in CPME (2.6 mL) was added followed by the dropwise addition of LiHMDS (3.1 mL, 3.1 mmol) at room temperature. The reaction was heated to 60° C. for 3 h. The crude material was purified by silica gel column chromatography (gradient elution: 0-100% EtOAc:/hexanes) to provide racemic 1-(5-fluoro-1H-indazol-6-yl)spiro[2.2]pentane-1-carbonitrile. MS (ESI) m/z calc'd for C$_{13}$H$_{11}$FN$_3$ [M+H]$^+$ 228 found 228.

Preparation of Intermediate U.3, 4-chloro-6-(1-(oxetan-3-yl)piperidin-4-yl)pyrimidine Scheme U

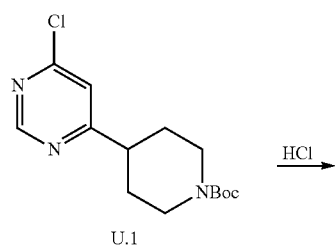

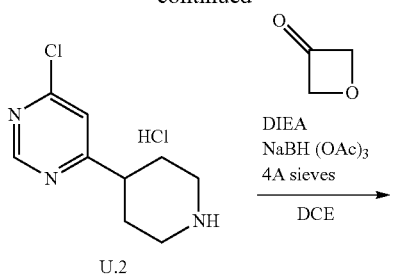

Step 1—Synthesis of U.2
4-(6-chloropyrimidin-4-yl)piperidine Hydrochloride tert-butyl 4-(6-chloropyrimidin-4-yl)piperidine-1-carboxylate (225 mg, 0.756 mmol) was dissolved in dioxane (1.5 mL) (used sonication to aid dissolution), and hydrogen chloride (4M in dioxane, 1.5 mL, 6.00 mmol) was added. The reaction mixture was allowed to stir at room temperature overnight. The reaction was diluted with Et$_2$O and the precipitated solids were filtered and washed with additional Et$_2$O. The remaining solid was dried in vacuo for about 3 hours, and then used in the subsequent step without further purification.

Step 2—Synthesis of U.3 4-chloro-6-(1-(oxetan-3-yl)piperidin-4-yl)pyrimidine 4-chloro-6-(piperidin-4-yl)pyrimidine hydrochloride (60 mg, 0.256 mmol) was dissolved/suspended in CH$_2$Cl$_2$ (1.0 mL) and DIEA (0.045 mL, 0.256 mmol). Oxetan-3-one (0.033 mL, 0.513 mmol) and 75 mg of dried and activated 4A molecular sieves were then added. After 1 hour, the reaction was treated with sodium triacetoxyborohydride (103 mg, 0.487 mmol), and stirred overnight. The reaction was quenched with aq. NaHCO$_3$ and extracted with DCM. The combined organics were dried over sodium sulfate, filtered and concentrated in vacuo. The resulting crude material was purified by silica gel chromatography eluting with 3:1 EtOAc:EtOH in DCM to give the title compound. MS(ESI) m/z calc'd for C$_{12}$H$_{16}$ClN$_3$O [M+H]$^+$ 254 found 254.

Preparation of Intermediate V.4-1 (S or R)-1-(1-(2-methyl-6-(methylsulfonyl)pyrimidin-4-yl)-1H-pyrazolo[4,3-c]pyridin-6-yl)spiro[2.2]pentane-1-carbonitrile and (S or R)-1-(1-(2-methyl-6-(methylsulfonyl)pyrimidin-4-yl)-1H-pyrazolo[4,3-c]pyridin-6-yl)spiro[2.2]pentane-1-carbonitrile V.4-2

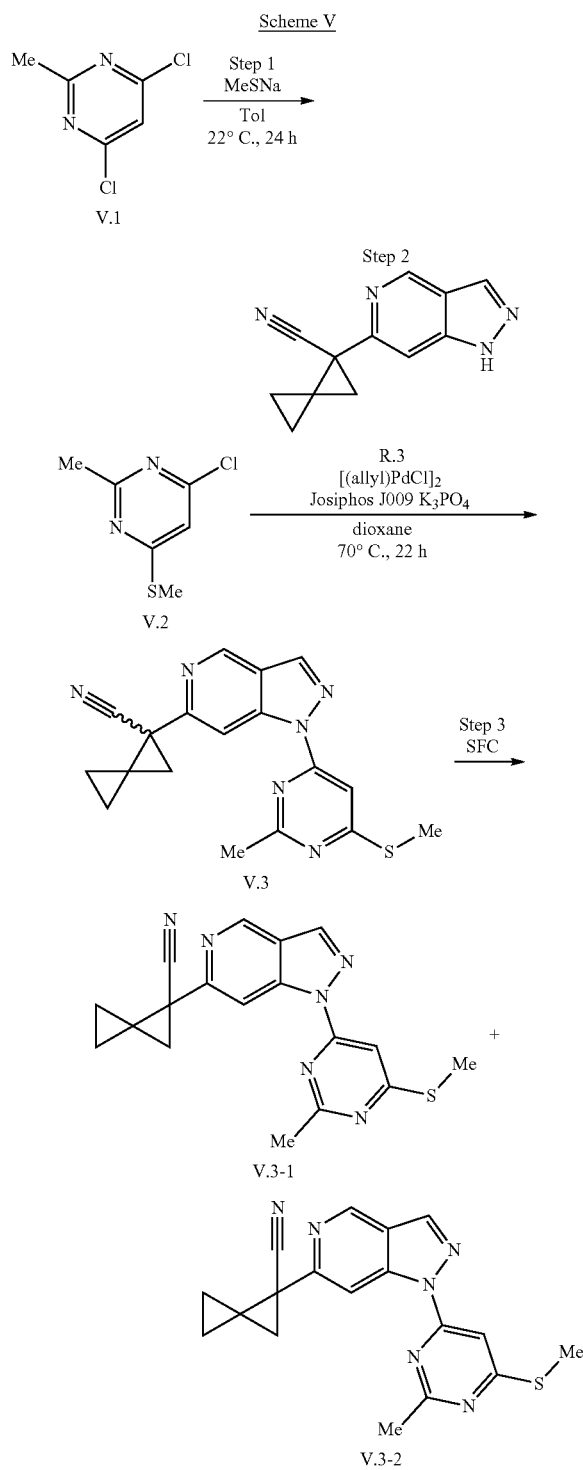

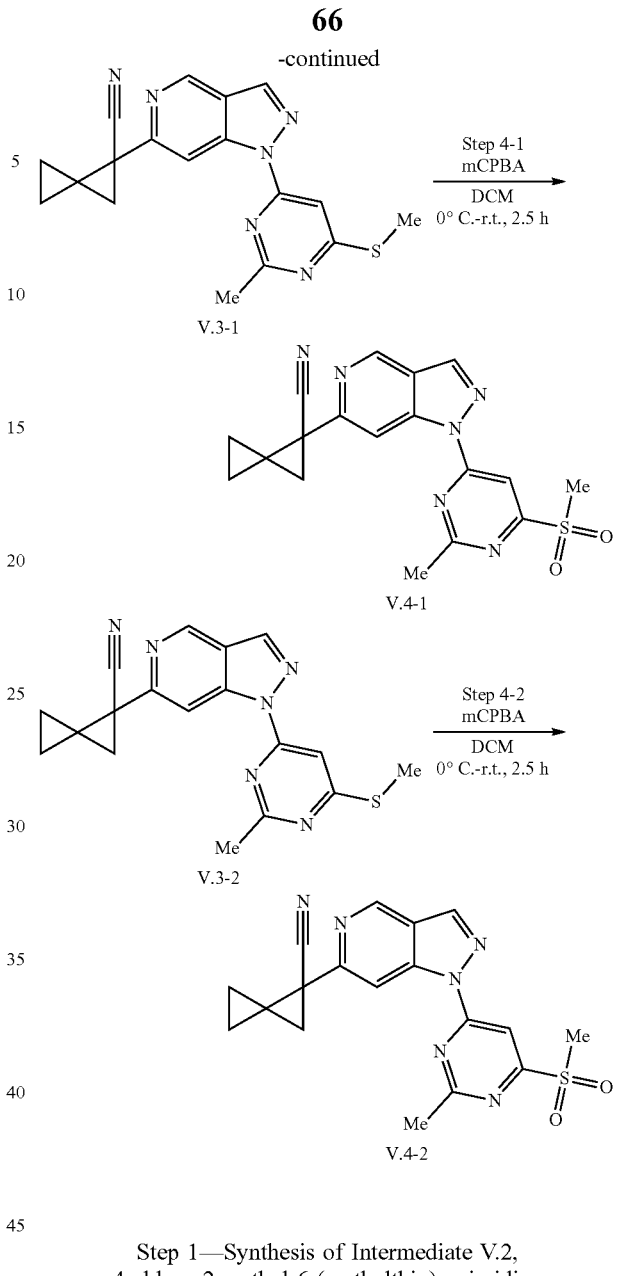

Step 1—Synthesis of Intermediate V.2, 4-chloro-2-methyl-6-(methylthio)pyrimidine A 5-L 3-necked round-bottom flask was purged and maintained under an inert atmosphere of nitrogen. The vessel was charged with 4,6-dichloro-2-methylpyrimidine (200 g) and MeSNa (86 g) in toluene (2 L). The resulting solution was stirred for 24 h at room temperature. The resulting solution was diluted with 3 L of water. The resulting solution was extracted with ethyl acetate (2×2 L) dried over anhydrous sodium sulfate and concentrated under vacuum. The residue was purified by column chromatography on silica gel eluting with ethyl acetate/petroleum ether (1:10-1:5). This provided 4-chloro-2-methyl-6-(methylsulfanyl) pyrimidine.

Step 2—Synthesis of Intermediate V.3, 1-(1-(2-methyl-6-(methylthio)pyrimidin-4-yl)-1H-pyrazolo[4,3-c]pyridin-6-yl)spiro[2.2]pentane-1-carbonitrile A 5-L 4-necked round-bottom flask was purged and maintained under an inert atmosphere of nitrogen. The vessel was charged with 4-chloro-2-methyl-6-(methylsulfanyl)pyrimidine (83 g), 1-[1H-pyrazolo[4,3-c]pyridin-6-yl]spiro[2.2]pentane-1-carbonitrile (100 g), $K_3PO_4$ (300 g), Josiphos J009 (26 g) and [(allyl)PdCl]$_2$ (8.7 g) in dioxane (2 L). The resulting solution was stirred for overnight at 70° C. The solids were filtered and the resulting mixture was concentrated under vacuum. The crude product was re-crystallized from EA: PE: EtOH (1:4:1). This provided 1-[1-[2-methyl-6-(methylsulfanyl)pyrimidin-4-yl]-1H-pyrazolo[4,3-c]pyridin-6-yl]spiro[2.2]pentane-1-carbonitrile.

Step 3—Resolution of V.3

1-[1-[2-methyl-6-(methylsulfanyl)pyrimidin-4-yl]-1H-pyrazolo[4,3-c]pyridin-6-yl]spiro[2.2]pentane-1-carbonitrile (V.3) was purified by Prep-SFC with the following conditions: Column, CHIRALPAK AS-H5×25 cm, 5 um S90ASHSCY-UC00120455; mobile phase, A: $CO_2$ 55% B: IPA 45%; Detector, UV. This resulted in (1S or 1R)-1-[1-[2-methyl-6-(methylsulfanyl)pyrimidin-4-yl]-1H-pyrazolo[4,3-c]pyridin-6-yl]spiro[2.2]pentane-1-carbonitrile V.3-1 and (1S or 1R)-1-[1-[2-methyl-6-(methylsulfanyl)pyrimidin-4-yl]-1H-pyrazolo[4,3-c]pyridin-6-yl]spiro[2.2]pentane-1-carbonitrile V.3-2.

Step 4-1—Synthesis of Intermediate V.4-1 (S or R)-1-(1-(2-methyl-6-(methylsulfonyl)pyrimidin-4-yl)-1H-pyrazolo[4,3-c]pyridin-6-yl)spiro[2.2]pentane-1-carbonitrile A 2-L 4-necked round-bottom flask purged and maintained with an inert atmosphere of nitrogen. The vessel was charged with (1S or R)-1-[1-[2-methyl-6-(methylsulfanyl)pyrimidin-4-yl]-1H-pyrazolo[4,3-c]pyridin-6-yl]spiro[2.2]pentane-1-carbonitrile (V.3-1) in DCM (1 L). This was followed by the addition of m-CPBA (33 g) in several batches at 0° C. The resulting solution was stirred for 10 min at 0° C. in an ice/salt bath. The resulting solution was allowed to stir for an additional 2 h at room temperature. The reaction progress was monitored by LCMS. The reaction mixture was cooled to 0° C. with an ice/salt bath and the reaction was then quenched by the addition of aqueous $NaHCO_3$ (1 L). The resulting solution was extracted with DCM (2×500 mL), dried over anhydrous sodium sulfate and concentrated under vacuum. The residue was purified by column chromatography on silica gel eluting with EtOH:EA:PE (1:1:4). This provided (1S or 1R)-1-[1-(6-methanesulfonyl-2-methylpyrimidin-4-yl)-1H-pyrazolo[4,3-c]pyridin-6-yl]spiro[2.2]pentane-1-carbonitrile. CHIRAL-Analytical-SFC [Column: CHIRALPAK IF-3, 3×100 mm (3 μm); 20%[MeOH/DCM (1:1)/(0.1% DEA)]/$CO_2$; Flow rate: 2 m/min; 240 nm; RT1:3.71 min (V.4-1); RT2: 4.31 min (V.4-2)]. MS (ES, m/z) calc'd for $C_{18}H_{17}N_6O_2S$ [M+H]$^+$ 381 found 381. $^1$H NMR (400 MHz, CDCl$_3$) δ 9.08 (1H, s), 8.98 (1H, s), 8.47 (1H, s), 8.39 (1H, s), 3.37 (3H, s), 2.94 (3H, s), 2.46-2.47 (1H, d, J=4.2 Hz), 2.32-2.33 (1H, d, J=3.9 Hz), 1.21-1.37 (3H, m), 0.96-1.00 (1H, m).

Step 4-2—Synthesis of Intermediate V.4-2 (S or R)-1-(1-(2-methy-6-(methylsulfonyl)pyrimidin-4-yl)-1H-pyrazolo[4,3-c]pyridin-6-yl)spiro[2.2]pentane-1-carbonitrile A 2-L 3-necked round-bottom flask purged and maintained with an inert atmosphere of nitrogen. The vessel was charged with (1R or 1S)-1-[1-[2-methyl-6-(methylsulfanyl)pyrimidin-4-yl]-1H-pyrazolo[4,3-c]pyridin-6-yl]spiro[2.2]pentane-1-carbonitrile (22 g) in DCM (1 L). This was followed by the addition of m-CPBA (33 g) in several batches at 0° C. The resulting solution was stirred for 10 min at 0° C. in an ice/salt bath. The resulting solution was allowed to stir for an additional 2 h at room temperature. The reaction progress was monitored by LCMS. The reaction mixture was cooled with a water/ice bath. The reaction was then quenched by the addition of aqueous $NaHCO_3$ (1 L). The resulting solution was extracted with dichloromethane (2×500 mL) and the organic layers combined and dried over anhydrous sodium sulfate and concentrated under vacuum. The residue was purified by column chromatography on silica gel eluting with EtOH:EA:PE (1:1:4). This provided (R or S)-1-(1-(2-methyl-6-(methylsulfonyl)pyrimidin-4-yl)-1H-pyrazolo[4,3-c]pyridin-6-yl)spiro[2.2]pen-tane-1-carbonitrile. CHIRAL-Analytical-SFC [Column: CHIRALPAK IF-3, 3×100 mm (3 μm); 20%[MeOH/DCM (1:1)/(0.1% DEA)]/$CO_2$; Flow rate: 2 mL/min; 240 nm; RT1:3.71 min (V.4-1); RT2: 4.31 min (V.4-2)]. MS (ES, m/z) calc'd for $C_{18}H_{17}N_6O_2S$ [M+H]$^+$ 381 found 381. $^1$H NMR (400 MHz, CDCl$_3$) δ 9.08 (1H, s), 8.98 (1H, s), 8.47 (1H, s), 8.39 (1H, s), 3.33 (3H, s), 2.94 (3H, s), 2.46-2.47 (1H, d, J=3.6 Hz), 2.32-2.33 (1H, d, J=3.9 Hz), 1.23-1.37 (3H, m), 0.96-1.00 (1H, m).

Preparation of Intermediate W.4 (2-(2,2,2-trifluoroethyl)-2,6-diazaspiro[3.3]heptane

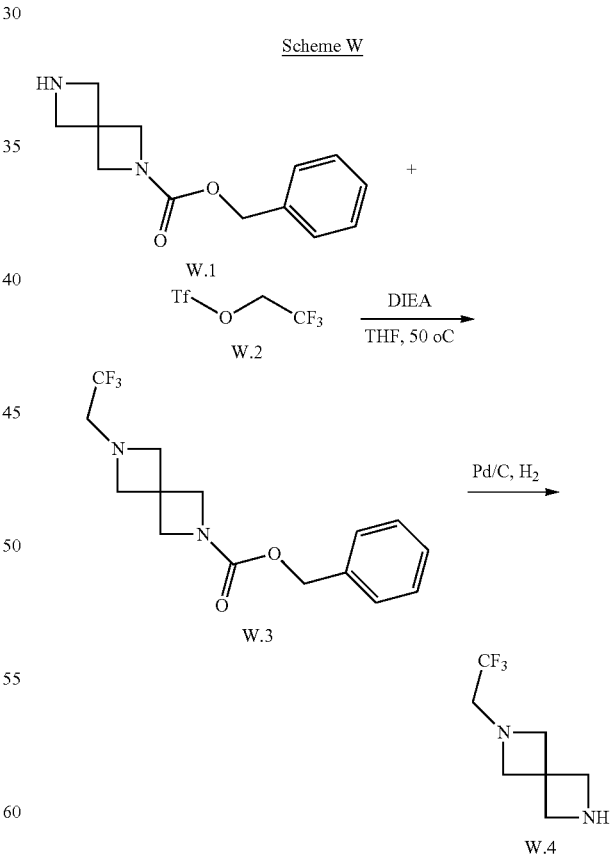

Scheme W

Benzyl 2,6-diazaspiro[3.3]heptane-2-carboxylate, HCl (2.92 g, 10.87 mmol), THF (25 ml), DIEA (9.49 ml, 54.3 mmol), and 2,2,2-trifluoroethyl trifluoromethanesulfonate (3.13 ml, 21.73 mmol) were added to a round-bottom flask.

The flask was fitted with a Findensor™ air condenser and the resulting mixture was allowed to stir overnight at 50° C. The reaction mixture was concentrated under reduced pressure. The residue was purified by column chromatography on silica (0-70% 3:1 Ethyl Acetate:Ethanol/Hexane). The desired fractions were pooled and concentrated under reduced pressure to afford benzyl 6-(2,2,2-trifluoroethyl)-2,6-diazaspiro[3.3]heptane-2-carboxylate. MS (ESI) m/z calc'd for $C_{15}H_{17}F_3N_2O_2$ [M+H]$^+$ 315 found 315.

Pd—C (0.339 g, 0.318 mmol) was added to a flask containing benzyl 6-(2,2,2-trifluoroethyl)-2,6-diazaspiro[3.3]heptane-2-carboxylate (1 g, 3.18 mmol) dissolved in EtOH (15 ml). The slurry was evacuated and purged with hydrogen (6 times), and then allowed to stir for 2 hours at room temperature. The reaction mixture was backfilled with argon, and then filtered through a plug of Celite®. The eluent was concentrated under reduced pressure to afford 2-(2,2,2-trifluoroethyl)-2,6-diazaspiro[3.3]. MS (ESI) m/z calc'd for $C_7H_{11}F_3N_2$ [M+H]$^+$ 181 found 181.

Preparation of intermediate X.5, 2-(6-chloro-2-methylpyrimidin-4-yl)-6-(oxetan-3-yl)-2,6 diazaspiro[3.3]heptane

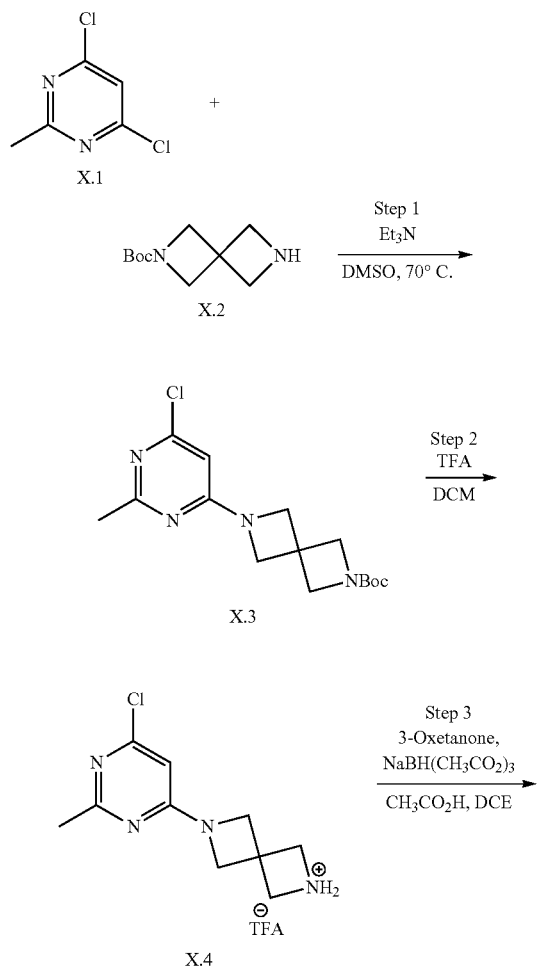

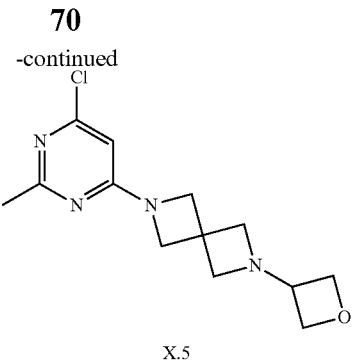

Step 1—Synthesis of Intermediate X.3, tert-butyl 6-(6-chloro-2-methylpyrimidin-4-yl)-2,6-diazaspiro[3.3]heptane-2-carboxylate To a solution of 4,6-dichloro-2-methylpyrimidine (1000 mg, 6.13 mmol) in anhydrous DMSO (8.35 mL) at rt was added triethylamine (2.65 mL, 15.4 mmol), and tert-butyl 2,6-diazaspiro[3.3]heptane-2-carboxylate, oxalic acid- (1762 mg, 6.13 mmol). The resulting mixture was stirred at 70° C. for 12 h. The reaction mixture was cooled to rt, and poured into water (10 mL. The resulting slurry was filtered through Celite®, and the solid precipitate was dried in vacuo to yield crude tert-butyl 6-(6-chloro-2-methylpyrimidin-4-yl)-2,6-diazaspiro[3.3]heptane-2-carboxylate, X.3 that was used without further purification. MS(ESI) m/z calc'd for $C_{15}H_{22}ClN_4O_2$ [M+H]$^+$ 325 found 325.

Step 2—Synthesis of Intermediate X.4, 2-(6-chloro-2-methylpyrimidin-4-yl)-2,6-diazaspiro[3.3]heptane, TFA Salt To a solution of tert-butyl 6-(6-chloro-2-methylpyrimidin-4-yl)-2,6-diazaspiro[3.3]heptane-2-carboxylate, X.3 (1700 mg, 5.23 mmol) in anhydrous DCM (17.4 mL) was added TFA (17.4 mL). The mixture was stirred at rt for 12 h. The reaction mixture was concentrated in vacuo to afford 2-(6-chloro-2-methylpyrimidin-4-yl)-2,6-diazaspiro[3.3]heptane, TFA salt, X.4 which was used in the step without further purification. MS(ESI) m/z calc'd for $C_{10}H_{14}ClN_4$ [M+H]$^+$ 225 found 225.

Step 3—Synthesis of Intermediate X.5, 2-(6-chloro-2-methylpyrimidin-4-yl)-6-(oxetan-3-yl)-2,6-diazaspiro[3.3]heptane To a solution of 2-(6-chloro-2-methylpyrimidin-4-yl)-2,6-diazaspiro[3.3]heptane, TFA salt, X.4 (3000 mg, 8.86 mmol) in anhydrous DCE (25.7 mL) was added 3-oxetanone (1277 mg, 17.71 mmol), acetic acid (0.96 mL, 16.8 mmol), and then sodium triacetoxyborohyride (2816 mg, 13.3 mmol). The mixture was stirred at rt for 12 h. The reaction was diluted with DCM (15 mL), washed with water (15 m), and dried over solid Na$_2$SO$_4$, and then filtered through Celite®. The organics were concentrated in vacuo to yield crude material that was purified using SiO$_2$ chromatography (0 to 100% EtOAc:EtOH (3:1) in hexanes gradient) to afford 2-(6-chloro-2-methylpyrimidin-4-yl)-6-(oxetan-3-yl)-2,6-diazaspiro[3.3]heptane, X.5. MS(ESI) m/z calc'd for $C_{13}H_{18}ClN_4O$ [M+H]$^+$ 281 found 281.

Preparation of Y.4 (4aS,7aR) or (4aR,7aS)-4-Methyloctahydropyrrolo[3,4-b][1,4]oxazine

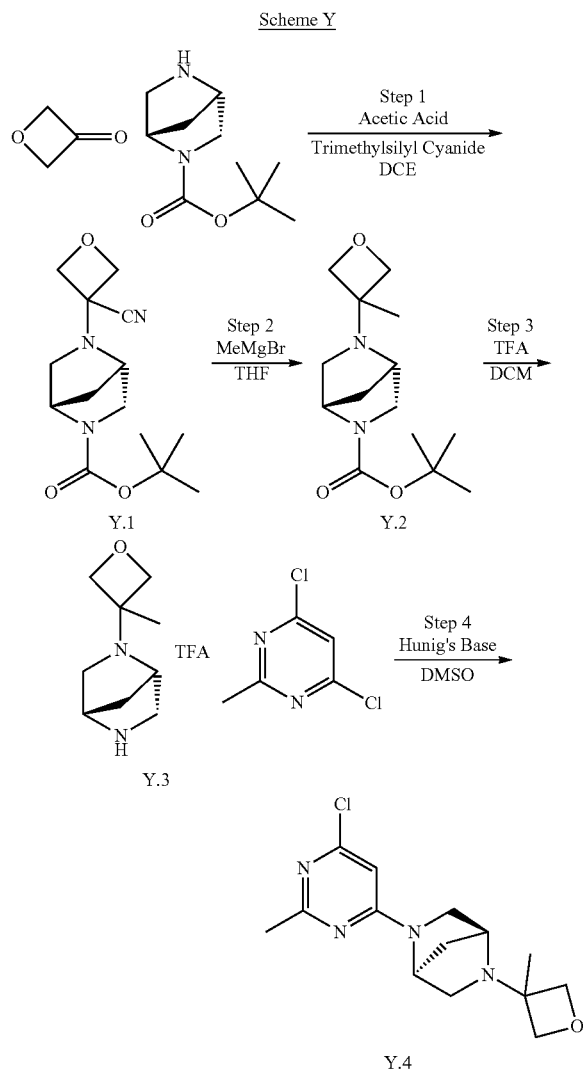

Step 1: Synthesis of Intermediate, Y.1, tert-butyl (1S,4S)-5-(3-cyanooxetan-3-yl)-2,5-diazabicyclo[2.2.1]heptane-2-carboxylate To a 20 mL reaction vial with magnetic stir bar under an atmosphere of $N_2$ was charged (1S,4S)-tert-butyl 2,5-diazabicyclo[2.2.1]heptane-2-carboxylate (300 mg, 1.513 mmol). 3-Oxetanone (0.133 mL, 2.270 mmol) was then added followed by addition of acetic acid (0.104 mL, 1.816 mmol). The vial was stirred at 65° C. for 30 min after which trimethylsilyl cyanide (0.243 mL, 1.816 mmol) was added. The reaction vessel was stirred at 65° C. for an additional 16 h, and then cooled to rt. The reaction mixture was diluted with DCM and 1M NaOH. The layers were separated, and the aqeuous layer was extracted with DCM (2×). The combined organics were then dried over magnesium sulfate, and concentrated in vacuo. The crude residue was purified using $SiO_2$ chromatography (hexanes/Ethyl Acetate, 0-100% gradient) to afford (1S,4S)-tert-butyl 5-(3-cyanooxetan-3-yl)-2,5-diazabicyclo[2.2.1]heptane-2-carboxylate. MS (ESI) m/z calc'd for $C_{14}H_{21}N_3O_3$ [M+H]$^+$ 280, found 280.

Step 2: Preparation of Y.2 tert-butyl (1S,4S)-5-(3-methyloxetan-3-yl)-2,5-diazabicyclo[2.2.1]heptane-2-carboxylate To a 20 mL reaction vial with magnetic stir bar under an atmosphere of $N_2$ was added (1S,4S)-tert-butyl 5-(3-cyanooxetan-3-yl)-2,5-diazabicyclo[2.2.1]heptane-2-carboxylate (348 mg, 1.246 mmol) and THF (6.2 mL). Methylmagnesium bromide (2.076 mL, 6.23 mmol) was added, and the reaction mixture was heated to 65° C. overnight. The reaction mixture was allowed to cool to room temperature, quenched with 1 M NaOH, and diluted with DCM. The layers were separated, and the aqueous phase was extracted with DCM. The combined organic layers were dried over solid $Na_2SO_4$, filtered, and concentrated in vacuo. The crude residue was purified using $SiO_2$ chromatography (0-100% Ethyl Acetate in Hexanesgradient) to yield (1S,4S)-tert-butyl 5-(3-methyloxetan-3-yl)-2,5-diazabicyclo[2.2.1]heptane-2-carboxylate. MS (ESI) m/z calc'd for $C_{14}H_{24}N_2O_3$ [M+H]$^+$ 269, found 269.

Step 3: Preparation of Y.3, (1S,4S)-2-(3-methyloxetan-3-yl)-2,5 diazabicyclo[2.2.1]heptane, TFA Salt To a 20 mL reaction vial with magnetic stir bar was added (1S,4S)-tert-butyl 5-(3-methyloxetan-3-yl)-2,5-diazabicyclo[2.2.1]heptane-2-carboxylate (450 mg, 1.677 mmol), DCM (3 mL), and TFA (1 mL, 13.07 mmol). The reaction mixture was stirred at room temperature overnight, and then concentrated in vacuo to afford crude (1S,4S)-2-(3-methyloxetan-3-yl)-2,5-diazabicyclo[2.2.1]heptane, 2TFA that was in a subsequent step without any further purification. MS (ESI) m/z calc'd for $C_9H_{16}N_2O$ [M+H]$^+$ 169, found 169.

Step 4: Preparation of Y.4, (1S,4S)-2-(6-chloro-2-methylpyrimidin-4-yl)-5-(3-methyloxetan-3-yl)-2,5-diazabicyclo[2.2.1]heptane A 20 mL vial equipped with magnetic stir bar was charged with (1S,4S)-2-(3-methyloxetan-3-yl)-2,5-diazabicyclo[2.2.1]heptane, 2TFA (321 mg, 0.810 mmol), 4,6-dichloro-2-methylpyrimidine (120 mg, 0.736 mmol), DMSO (1 mL), and N,N-diisopropylethylamine (0.641 mL, 3.68 mmol). The reaction mixture was stirred at 80° C. overnight, and then cooled to rt. The mixture was diluted with DCM and water. The layers were separated, and the aqeuous layer was extracted with DCM. The combined organic layers were dried over solid $Na_2SO_4$, filtered, and concentrated in vacuo to yield crude (1S,4S)-2-(6-chloro-2-methylpyrimidin-4-yl)-5-(3-methyloxetan-3-yl)-2,5-diazabicyclo[2.2.1]heptane that was used in subsequent steps without any purification. MS (ESI) m/z calc'd for $C_{14}H_{19}ClN_4O$ [M+H]$^+$ 295 found 295.

Preparation of Intermediate Z.6

Scheme Z

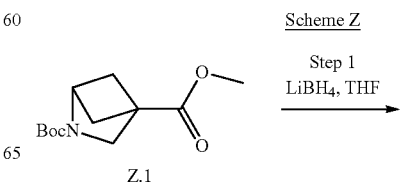

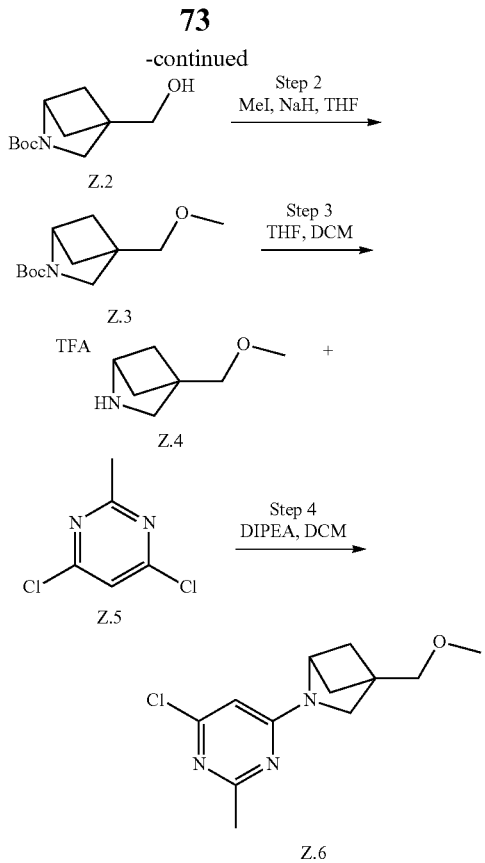

Step 1—Synthesis of Z.2, tert-butyl 4-(hydroxymethyl)-2-azabicyclo[2.1.1]hexane-2-carboxylate A solution of 2-(tert-butyl) 4-methyl 2-azabicyclo[2.1.1]hexane-2,4-dicarboxylate (1.02 g, 4.23 mmol) in THF (6.80 ml) was added lithium borohydride (4.23 ml, 8.45 mmol). The mixture was allowed to stir at 23° C. The reaction was diluted with DCM and washed with water. The organic layer dried over $Na_2SO_4$, filtered and concentrated to provide tert-butyl 4-(hydroxymethyl)-2-azabicyclo[2.1.1]hexane-2-carboxylate as a colorless oil. Proceeded to step 2 without further purification.

Step 2—Synthesis of Z.3, tert-butyl 4-(methoxymethyl)-2-azabicyclo[2.1.1]hexane-2-carboxylate To a solution of tert-butyl 4-(hydroxymethyl)-2-azabicyclo[2.1.1]hexane-2-carboxylate (641 mg, 3.01 mmol) in THF (6.290 mL) was added sodium hydride (144 mg, 3.61 mmol), the mixture was stirred at room temperature for 10 min before iodomethane (0.187 mL, 3.01 mmol) was added dropwise. Reaction mixture was allowed to stir at 23° C. The reaction was diluted in DCM and added saturated $NH_4Cl$. The aqueous layer was extracted with DCM (3×15 mL). The combined organic layer was washed with brine and dried over $Na_2SO_4$, filtered and concentrated to give tert-butyl 4-(methoxymethyl)-2-azabicyclo[2.1.1]hexane-2-carboxylate which was used without purification.

Step 3—Synthesis of Z.4, 4-(methoxymethyl)-2-azabicyclo[2.1.1]hexane, TFA

To a solution of tert-butyl 4-(methoxymethyl)-2-azabicyclo[2.1.1]hexane-2-carboxylate (660 mg, 2.90 mmol) in DCM (10 mL) was added trifluoroacetic acid (0.662 mL, 8.71 mmol). The reaction mixture was allowed to stir at 23° C. for 60 min and then concentrated to dryness to afford 4-(methoxymethyl)-2-azabicyclo[2.1.1]hexane, TFA. Submitted to last step without purification.

Step 4—Preparation of Z.6, 2-(6-chloro-2-methylpyrimidin-4-yl)-4-(methoxymethyl)-2-azabicyclo[2.1.1]hexane To a solution of 4-(methoxymethyl)-2-azabicyclo[2.1.1]hexane, TFA (1.23 g, 5.10 mmol) in DCM (12.75 ml) was added DIPEA (4.44 ml, 25.5 mmol) and 4,6-dichloro-2-methylpyrimidine (0.831 g, 5.10 mmol). The mixture was allowed to stir at 23° C. The reaction was diluted with DCM and added saturated $NH_4Cl$. The aqueous layer was extracted with DCM (3×15 mL), and the combined organic layer was washed with brine then dried over $Na_2SO_4$, filtered and concentrated to dryness. The residue was purified by silica gel chromatography (gradient elution: 0-40% EtOAc/Hex). The fractions were pooled and concentrated to afford 2-(6-chloro-2-methylpyrimidin-4-yl)-4-(methoxymethyl)-2-azabicyclo[2.1.1]hexane. MS (ESI) m/z calc'd for $C_{12}H_{16}ClN_3O$ $[M+H]^+$ 253 found 253.

EXAMPLES

Preparation of Examples 1.4-1 and 1.4-2, (R or S)-1-(1-(6-((R)-3-(2-hydroxypropan-2-yl)pyrrolidin-1-yl)pyrimidin-4-yl)-1H-indazol-6-yl)spiro[2.2]pentane-1-carbonitrile, +isomer

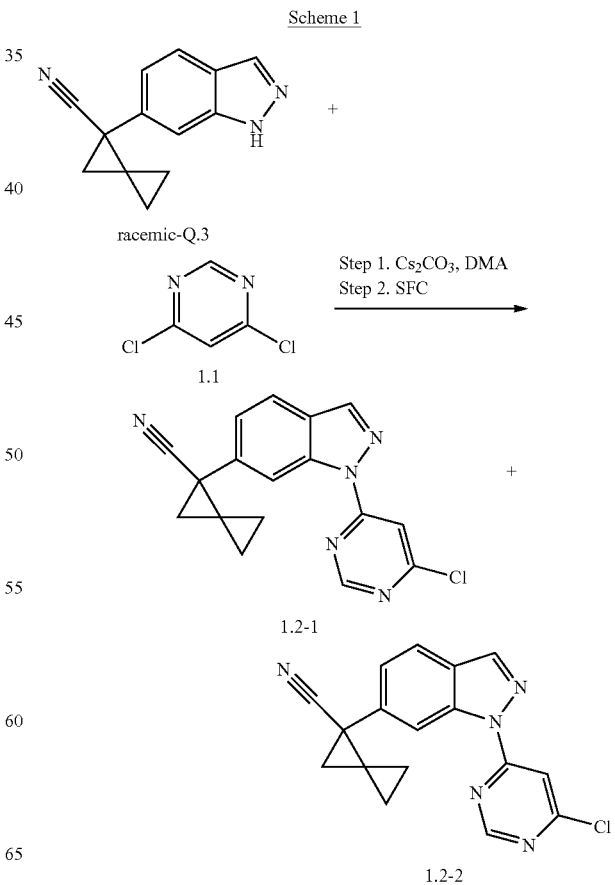

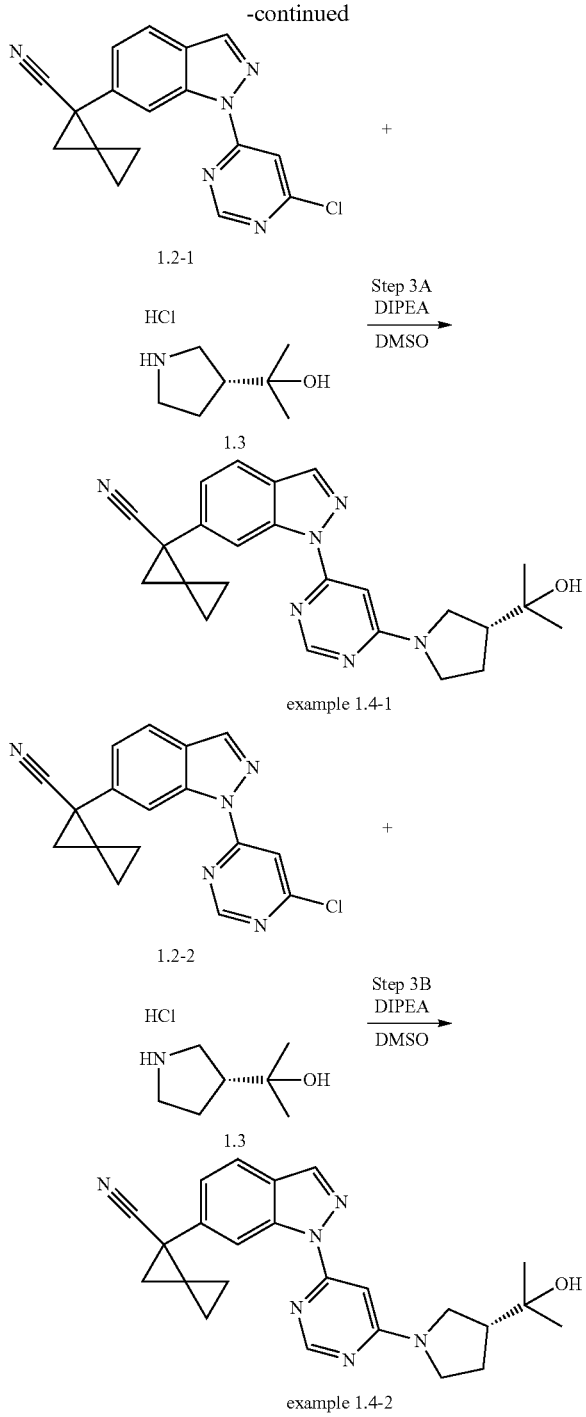

Step 1—Synthesis of Intermediate 1.2-1 and 1.2-2, 1-(1-(6-chloropyrimidin-4-yl)-1H-indazol-6-yl)spiro[2.2]pentane-1-carbonitrile 4,6-dichloropyrimidine (3.72 g, 24.97 mmol), racemic-1-(1H-indazol-6-yl)spiro[2.2]pentane-1-carbonitrile (4.75 g, 22.70 mmol) and cesium carbonate (18.49 g, 56.8 mmol) in DMA (227 mL) were heated to 60° C. overnight. The mixture was diluted with EtOAc (200 mL) and the combined organic fractions were washed with brine (3×200 mL), dried over Na$_2$SO$_4$, filtered and concentrated. The residue was purified by column chromatography on silica gel (gradient: 0% to 100% EtOAc/isohexane) to provide 1-(1-(6-chloropyrimidin-4-yl)-1H-indazol-6-yl)spiro[2.2]pentane-1-carbonitrile. MS (ESI) m/z calc'd for C$_{17}$H$_{13}$ClN$_5$ [M+H]$^+$ 322 found 322]. The product coeluted with the minor indazole N2-regioisomer, 4:1 ratio by LCMS.

Step 2-Resolution of 1.2

This material required 2 rounds of SFC to be purified. In the first round the material was purified using Chiral-Prep-SFC [Column: CHIRALPAK IB, 21×250 mm (5 μm); 15% (MeOH/0.25% DMEA)/CO$_2$; Flow rate: 70 mL/min; 220 nm; RT: 4.01 min (racemic peak)]. This material was then subjected to another round of Chiral-Prep-SFC [Column: IG, 21×250 mm (5 μm); 35% (MeOH/0.25% DMEA)/CO$_2$; Flow rate: 70 mL/min; 220 nm; RT1:3.98 (1.2-1), RT2: 4.99 (1.2-2) min].

Step 3A—Synthesis of Example 1.4-1, (R or S)-1-(1-(6-((R)-3-(2-hydroxypropan-2-yl)pyrrolidin-1-yl)pyrimidin-4-yl)-1H-indazol-6-yl)spiro[2.2]pentane-1-carbonitrile DIPEA (891 μL, 5.10 mmol), (R)-2-(pyrrolidin-3-yl)propan-2-ol hydrochloride (422 mg, 2.55 mmol) and (R or S)-1-(1-(6-chloropyrimidin-4-yl)-1H-indazol-6-yl)spiro[2.2]pentane-1-carbonitrile (547 mg, 1.700 mmol) (1.2-1) in DMSO (8.5 mL) were heated to 75° C. for 6 h. The mixture was diluted with EtOAc (20 mL), and the combined organic fractions were washed with brine (3×20 mL), dried over Na$_2$SO$_4$, filtered and concentrated. The residue was purified via column chromatography on silica gel (gradient: 0% to 100% EtOAc/isohexane). This material was further purified by Chiral-Prep-SFC [Column: OJ-H, 21×250 mm (5 μm); 20% (MeOH/0.25% DMEA)/CO$_2$; Flow rate: 70 mL/min; 220 nm; RT: 3.38 min]. This provided (R or S)-1-(1-(6-((R)-3-(2-hydroxypropan-2-yl)pyrrolidin-1-yl)pyrimidin-4-yl)-1H-indazol-6-yl)spiro[2.2]pentane-1-carbonitrile. MS (ESI) m/z calc'd for C$_{24}$H$_{27}$N$_6$O [M+H]$^+$ 415 found 415]. $^1$H NMR (499 MHz, DMSO-d$_6$) δ 8.92 (s, 1H), 8.50 (s, 1H), 8.45 (s, 1H), 7.89 (d, J=8.4 Hz, 1H), 7.17 (d, J=8.3 Hz, 1H), 6.83 (s, 1H), 4.42 (s, 1H), 3.93-3.81 (m, 1H), 3.76-3.66 (m, 1H), 3.59-3.49 (m, 1H), 3.46-3.40 (m, 1H), 2.37 (d, J=5.0 Hz, 1H), 2.30-2.19 (m, 1H), 2.04 (d, J=5.0 Hz, 1H), 1.99-1.78 (m, 2H), 1.32-1.20 (m, 3H), 1.19-1.10 (m, 6H), 1.06-0.97 (m, 1H). LRRK2 IC$_{50}$1.0 nM Step 3B—Synthesis of Example 1.4-2, (R or S)-1-(1-(6-((R)-3-(2-hydroxypropan-2-yl)pyrrolidin-1-yl)pyrimidin-4-yl)-1H-indazol-6-yl)spiro[2.2]pentane-1-carbonitrile DIPEA (858 μLL, 4.91 mmol), (R)-2-(pyrrolidin-3-yl)propan-2-ol hydrochloride (407 mg, 2.46 mmol) and (R or S)-1-(1-(6-chloropyrimidin-4-yl)-1H-indazol-6-yl)spiro[2.2]pentane-1-carbonitrile (527 mg, 1.64 mmol) (1.2-2) in DMSO (8.2 mL) were heated to 75° C. for 6 h. The mixture was diluted with EtOAc (20 mL) and the combined organic fractions were washed with brine (3×20 mL), dried over Na$_2$SO$_4$, filtered and concentrated. The residue was purified via column chromatography on silica gel (gradient: 0% to 100% EtOAc/isohexane). This material was further purified by Chiral-Prep-SFC [Column: OJ-H, 21×250 mm (5 μm); 15% (MeOH/0.25% DMEA)/CO$_2$; Flow rate: 70 mL/min; 220 nm; RT1:4.91 min]. This provided (R or S)-1-(1-(6-((R)-3-(2-hydroxypropan-2-yl)pyrrolidin-1-yl)pyrimidin-4- yl)-1H-indazol-6-yl)spiro[2.2]pentane-1-carbonitrile. MS (ESI) m/z calc'd for $C_{24}H_{27}N_6O$ [M+H]$^+$ 415 found 415]. $^1$H NMR (499 MHz, DMSO-d$_6$) δ 8.92 (s, 1H), 8.50 (s, 1H), 8.46 (s, 1H), 7.89 (d, J=8.4 Hz, 1H), 7.17 (d, J=8.3 Hz, 1H), 6.83 (s, 1H), 4.43 (s, 1H), 3.95-3.82 (m, 1H), 3.77-3.67 (m, 1H), 3.60-3.52 (m, 1H), 3.47-3.40 (m, 1H), 2.37 (d, J=5.0 Hz, 1H), 2.29-2.20 (m, 1H), 2.04 (d, J=5.0 Hz, 1H), 1.98-1.79 (m, 2H), 1.31-1.20 (m, 3H), 1.18-1.13 (m, 6H), 1.04-0.97 (m, 1H). LRRK2 IC$_{50}$ 0.9 nM The following examples were prepared according to General Scheme 1 and Scheme 1 above.

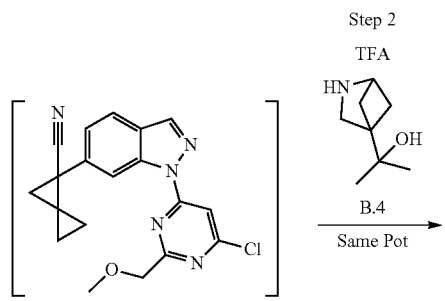

TABLE 5

Examples Prepared According to General Scheme 1 and Scheme 1

| Example | Structure Name | Observed m/z [M + H]$^+$ | LRRK2 IC$_{50}$ (nM) |
|---|---|---|---|
| 1.5 | 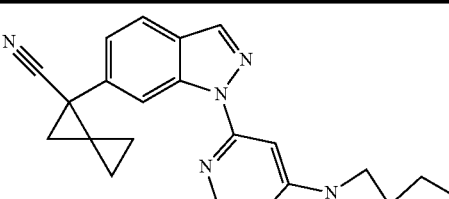<br>1-(1-(6-(6-oxa-2-azaspiro[3.4]octan-2-yl)pyrimidin-4-yl)-1H-indazol-6-yl)spiro[2.2]pentane-1-carbonitrile | 399 | 0.9 |

Preparation of Examples 2.3, 2.3-1 and 2.3-2, 1-(1-(6-chloro-2-(methoxymethyl)pyrimidin-4-yl)-1H-indazol-6-yl)spiro[2.2]pentane-1-carbonitrile, (R or S)-1-(1-(6-(4-(2-hydroxypropan-2-yl)-2-azabicyclo[2.1.1]hexan-2-yl)-2-(methoxymethyl)pyrimidin-4-yl)-1H-indazol-6-yl)spiro[2.2]pentane-1-carbonitrile Scheme 2

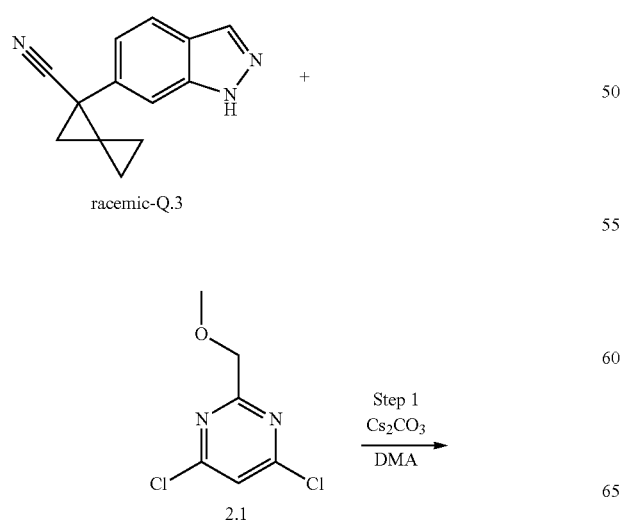

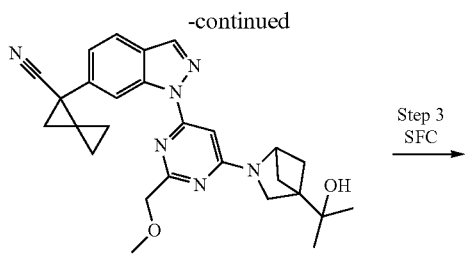

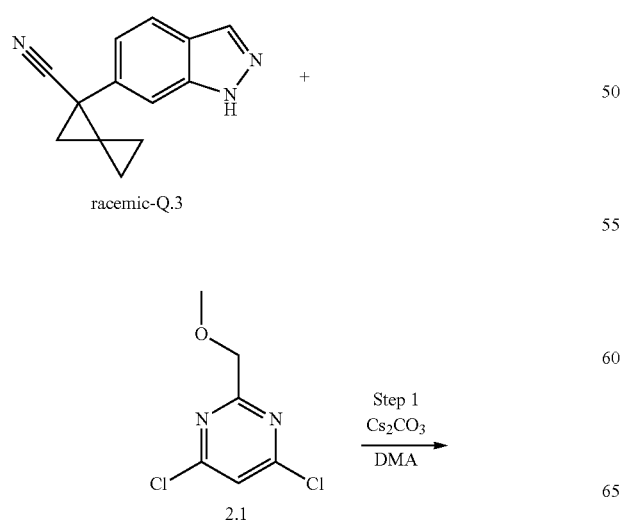

example 2.3-1

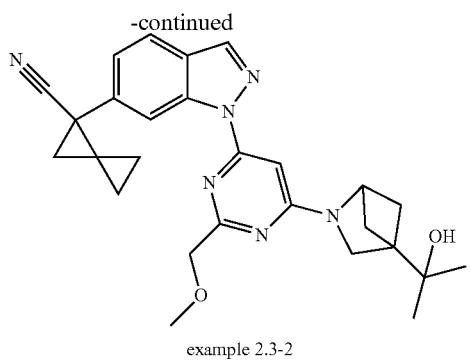

example 2.3-2

Step 1—Synthesis of Intermediate 2.2, 1-(1-(6-chloro-2-(methoxymethyl)pyrimidin-4-yl)-1H-indazol-6-yl)spiro[2.2]pentane-1-carbonitrile Cesium carbonate (490 mg, 1.51 mmol) and 4,6-dichloro-2-(methoxymethyl)pyrimidine (97 mg, 0.50 mmol were added to a solution of racemic 1-(1H-indazol-6-yl)spiro[2.2]pentane-1-carbonitrile (105 mg, 0.502 mmol) (Q.3) in DMA (1.0 mL) at room temperature. The reaction was stirred at room temperature for 2 h.

Step 2—Synthesis of 2.3, 1-(1-(6-(4-(2-hydroxypropan-2-yl)-2-azabicyclo[2.1.1]hexan-2-yl)-2-(methoxymethyl)pyrimidin-4-yl)-1H-indazol-6-yl)spiro[2.2]pentane-1-carbonitrile 2-(2-azabicyclo[2.1.1]hexan-4-yl)propan-2-ol, TFA salt (140 mg, 0.552 mmol) was added as one portion to the reaction above, and the reaction was heated to 45° C. for 20 h. The reaction was cooled to room temperature, water was added (5 mL), and the mixture was extracted with EtOAc (3×5 mL). The combined organic layers were dried over, $Na_2SO_4$, filtered and concentrated.

The crude material was purified by silica gel column chromatography [gradient elution: 15-60% (3:1 EtOAc: EtOH)/hexanes]. The resulting material was further purified via reverse phase prep-HPLC [method A] to provide 1-(1-(6-(4-(2-hydroxypropan-2-yl)-2-azabicyclo[2.1.1]hexan-2-yl)-2-(methoxymethyl)pyrimidin-4-yl)-1H-indazol-6-yl)spiro[2.2]pentane-1-carbonitrile.

Step 3-Resolution of 2.3

Racemic 1-(1-(6-(4-(2-hydroxypropan-2-yl)-2-azabicyclo[2.1.1]hexan-2-yl)-2-(methoxymethyl)pyrimidin-4-yl)-1H-indazol-6-yl)spiro[2.2]pentane-1-carbonitrile was purified by CHIRAL-Prep-SFC [Column: CHIRALPAK IC, 21×250 mm (5 μm); 45%(0.25% DMEA MeOH)/$CO_2$; Flow rate: 70 mL/min; 254 nm; RT1:4.15 min (2.3-1); RT2: 5.26 min (2.3-2)].

Example 2.3-1

MS (ESI) m/z calc'd for $C_{27}H_{31}N_6O_2$ [M+H]$^+$ 471 found 471. $^1$H NMR (499 MHz, DMSO-$d_6$) δ 9.00 (s, 1H), 8.45 (s, 1H), 7.88 (d, J=8.3 Hz, 1H), 7.22 (d, J=8.3 Hz, 1H), 7.00-6.61 (m, 2H), 4.95 (s, 1H), 4.43 (s, 2H), 3.45 (s, 3H), 3.41-3.36 (m, 1H), 3.17 (d, J=5.0 Hz, 1H), 2.39 (d, J=4.7 Hz, 1H), 2.00 (d, J=4.7 Hz, 1H), 1.96-1.87 (m, 2H), 1.46-1.36 (m, 2H), 1.30-1.20 (m, 3H), 1.21-1.09 (m, 6H), 1.06-0.98 (m, 1H). LRRK2 IC$_{50}$ 1.1 nM.

Example 2.3-2

MS (ESI) m/z calc'd for $C_{27}H_{31}N_6O_2$ [M+H]$^+$ 471 found 471. $^1$H NMR (499 MHz, DMSO-$d_6$) δ 9.00 (s, 1H), 8.45 (s, 1H), 7.88 (d, J=8.3 Hz, 1H), 7.22 (d, J=8.3 Hz, 1H), 7.00-6.61 (m, 2H), 4.95 (s, 1H), 4.43 (s, 2H), 3.45 (s, 3H), 3.41-3.36 (m, 1H), 3.17 (d, J=5.0 Hz, 1H), 2.39 (d, J=4.7 Hz, 1H), 2.00 (d, J=4.7 Hz, 1H), 1.96-1.87 (m, 2H), 1.46-1.36 (m, 2H), 1.30-1.20 (m, 3H), 1.21-1.09 (m, 6H), 1.06-0.98 (m, 1H). LRRK2 IC$_{50}$ 1.2 nM.

The following examples were prepared according to General Scheme 1 and Scheme 2 above.

TABLE 6

Examples Prepared According to General Scheme 1 and Scheme 2

| Example | Structure Name | Observed m/z [M + H]$^+$ | LRRK2 IC$_{50}$ (nM) |
| --- | --- | --- | --- |
| 2.4-1 | (R or S)-1-(1-(6-(4-(2-hydroxypropan-2-yl)-2-azabicyclo[2.1.1]hexan-2-yl)-2-methylpyrimidin-4-yl)-1H-indazol-6-yl)spiro[2.2]pentane-1-carbonitrile | 441 | 2.1 |

TABLE 6-continued

Examples Prepared According to General Scheme 1 and Scheme 2

| Example | Structure Name | Observed m/z [M + H]⁺ | LRRK2 IC$_{50}$ (nM) |
|---|---|---|---|
| 2.4-2 | 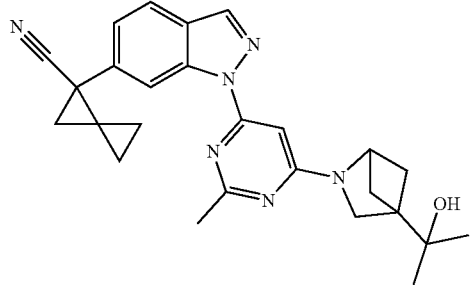<br>(R or S)-1-(1-(6-(4-(2-hydroxypropan-2-yl)-2-azabicyclo[2.1.1]hexan-2-yl)-2-methylpyrimidin-4-yl)-1H-indazol-6-yl)spiro[2.2]pentane-1-carbonitrile | 441 | 0.6 |
| 2.5-1 | 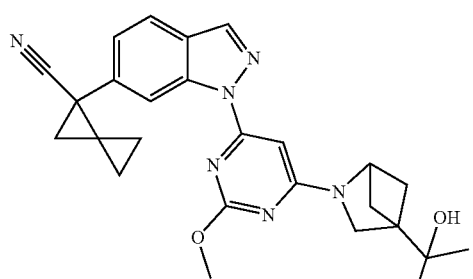<br>(R or S)-1-(1-(6-(4-(2-hydroxypropan-2-yl)-2-azabicyclo[2.1.1]hexan-2-yl)-2-methoxypyrimidin-4-yl)-1H-indazol-6-yl)spiro[2.2]pentane-1-carbonitrile | 457 | 0.9 |
| 2.5-2 | 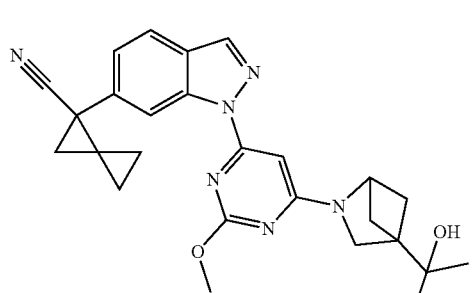<br>(R or S)-1-(1-(6-(4-(2-hydroxypropan-2-yl)-2-azabicyclo[2.1.1]hexan-2-yl)-2-methoxypyrimidin-4-yl)-1H-indazol-6-yl)spiro[2.2]pentane-1-carbonitrile | 457 | 0.8 |
| 2.6-1 | 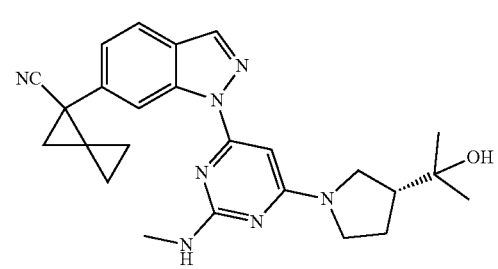<br>(S or R)-1-(1-(6-((R)-3-(2-hydroxypropan-2-yl)pyrrolidin-1-yl)-2-(methylamino)pyrimidin-4-yl)-1H-indazol-6-yl)spiro[2.2]pentane-1-carbonitrile, TFA salt | 444 | 0.8 |

TABLE 6-continued

Examples Prepared According to General Scheme 1 and Scheme 2

| Example | Structure Name | Observed m/z [M + H]+ | LRRK2 IC$_{50}$ (nM) |
|---|---|---|---|
| 2.6-2 | (S or R)-1-(1-(6-((R)-3-(2-hydroxypropan-2-yl)pyrrolidin-1-yl)-2-(methylamino)pyrimidin-4-yl)-1H-indazol-6-yl)spiro[2.2]pentane-1-carbonitrile, TFA salt | 444 | 0.8 |
| 2.7-1 | (R or S)-1-(1-(6-(4-(2-hydroxypropan-2-yl)-2-azabicyclo[2.1.1]hexan-2-yl)-2-(methylamino)pyrimidin-4-yl)-1H-indazol-6-yl)spiro[2.2]pentane-1-carbonitrile, TFA salt | 456 | 3.0 |
| 2.7-2 | (R or S)-1-(1-(6-(4-(2-hydroxypropan-2-yl)-2-azabicyclo[2.1.1]hexan-2-yl)-2-(methylamino)pyrimidin-4-yl)-1H-indazol-6-yl)spiro[2.2]pentane-1-carbonitrile | 456 | 0.6 |
| 2.8-1 | (R or S)-1-(1-(6-((S)-3-(difluoromethyl)pyrrolidin-1-yl)-2-(methylamino)pyrimidin-4-yl)-1H-indazol-6-yl)spiro[2.2]pentane-1-carbonitrile, TFA salt | 436 | 0.7 |

TABLE 6-continued

Examples Prepared According to General Scheme 1 and Scheme 2

| Example | Structure Name | Observed m/z [M + H]⁺ | LRRK2 IC$_{50}$ (nM) |
|---|---|---|---|
| 2.8-2 | 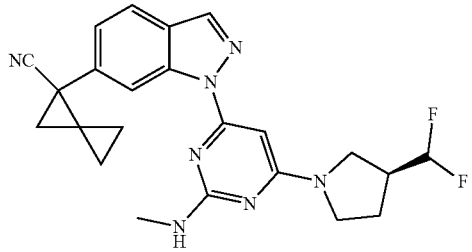 (R or S)-1-(1-(6-((S)-3-(difluoromethyl)pyrrolidin-1-yl)-2-(methylamino)pyrimidin-4-yl)-1H-indazol-6-yl)spiro[2.2]pentane-1-carbonitrile, TFA salt | 436 | 1.1 |

Resolution of Examples 2.4-1/2.4-2

1-(1-(6-(4-(2-hydroxypropan-2-yl)-2-azabicyclo[2.1.1]hexan-2-yl)-2-methylpyrimidin-4-yl)-1H-indazol-6-yl)spiro[2.2]pentane-1-carbonitrile was purified by CHIRAL-Prep-SFC [Column: CCOF4, 21×250 mm; 20%(0.25% DMEA/IPA)/CO$_2$; Flow rate: 70 mL/min; 254 nm; RT1:4.5 min (2.4-1); RT2: 5.6 min (2.4-2)].

Resolution of Examples 2.5-1/2.5-2

1-(1-(6-(4-(2-hydroxypropan-2-yl)-2-azabicyclo[2.1.1]hexan-2-yl)-2-methoxypyrimidin-4-yl)-1H-indazol-6-yl)spiro[2.2]pentane-1-carbonitrile was purified by CHIRAL-Prep-SFC [Column: CCOF4, 21×250 mm; 25%(0.25% DMEA/IPA)/CO$_2$ Flow rate: 70 mL/min; 254 nm; RT1:4.9 min (2.5-1); RT2: 5.9 min (2.5-2)].

Resolution of Examples 2.6-1/2.6-2

1-(1-(6-((R)-3-(2-hydroxypropan-2-yl)pyrrolidin-1-yl)-2-(methylamino)pyrimidin-4-yl)-1H-indazol-6-yl)spiro[1.2.2]pentane-1-carbonitrile was purified by CHIRAL-Prep-SFC [Column: CHIRALPAK IC, 3×25 cm (10 µm); 40% IPA/CO$_2$; Flow rate: 80 mL/min; 220 nm; RT1: 5.7 min (2.6-1); RT2: 6.8 min (2.6-2)]

Resolution of Examples 2.7-1/2.7-2

1-(1-(6-(4-(2-hydroxypropan-2-yl)-2-azabicyclo[2.1.1]hexan-2-yl)-2-(methylamino)pyrimidin-4-yl)-1H-indazol-6-yl)spiro[2.2]pentane-1-carbonitrile was purified by CHIRAL-Prep-SFC [Column: CHIRALPAK IC, 3×25 cm (10 µm); 45% IPA/CO$_2$; Flow rate: 80 mL/min; 220 nm; RT1: 3.8 min (2.7-1); RT2: 5.2 min (2.7-2)].

Resolution of Examples 2.8-1/2.8-2

1-(1-(6-((S)-3-(difluoromethyl)pyrrolidin-1-yl)-2-(methylamino)pyrimidin-4-yl)-1H-indazol-6-yl)spiro[2.2]pentane-1-carbonitrile was purified by separated by CHIRAL-Prep-SFC [Column: CHIRALPAK AD, 3×25 cm (5 µm); 45% EtOH/CO$_2$; Flow rate: 60 mL/min; 220 nm; RT1: 4.8 min (2.8-1); RT2: 6.0 min (2.8-2)]

Preparation of Example 3.1, (R or S)-1-(1-(6-((S)-3-methyl-4-(oxetan-3-yl)piperazin-1-yl)pyrimidin-4-yl)-1H-indazol-6-yl)spiro[2.2]pentane-1-carbonitrile, TFA Salt Scheme 3

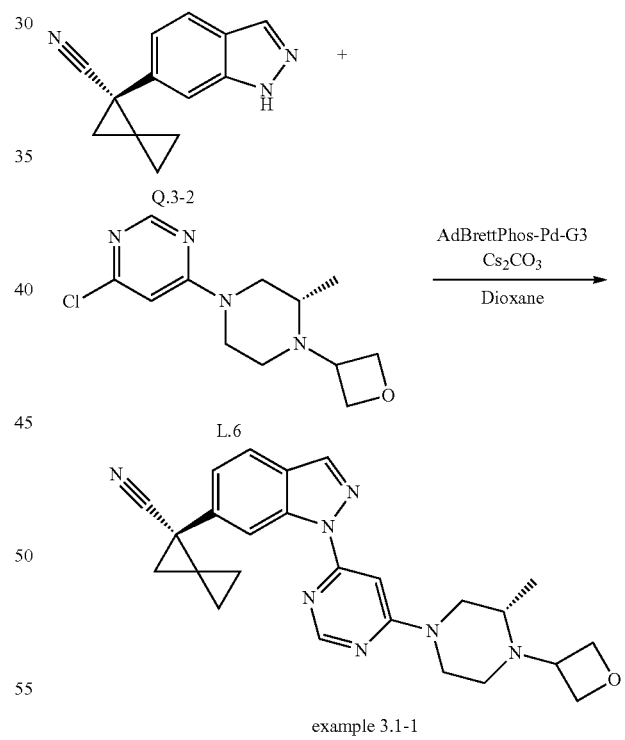

example 3.1-1

A solution of (S)-1-(1H-indazol-6-yl)spiro[2.2]pentane-1-carbonitrile (23 mg, 0.11 mmol) (Q.3-2), (S)-4-chloro-6-(3-methyl-4-(oxetan-3-yl)piperazin-1-yl)pyrimidine (30 mg, 0.11 mmol) (L.6), cesium carbonate (54 mg, 0.17 mmol) in 1,4-Dioxane (1 mL) was degassed by sparging with nitrogen. AdBrettPhos-Pd-G3 (11 mg, 0.011 mmol) was added; the vessel was sealed and purged with nitrogen (3×). The reaction was then stirred at 50° C. overnight. Additional AdBrettPhos-Pd-G3 (13 mg, 0.013 mmol) was added and stirring was continued at 50° C. overnight. The reaction was cooled to room temperature, diluted with EtOAc (5 mL), filtered over a pad of Celite®, and concentrated. The crude material was purified via reverse phase prep-HPLC [method A]. This provided (R or S)-1-(1-(6-((S)-3-methyl-4-(oxetan-3-yl)piperazin-1-yl)pyrimidin-4-yl)-1H-indazol-6-yl)spiro[2.2]pentane-1-carbonitrile, TFA salt. MS (ESI) m/z calc'd for $C_{25}H_{28}N_7O$ [M+H]$^+$ 442 found 442. $^1$H NMR (499 MHz, DMSO-d$_6$) δ 8.91 (s, 1H), 8.65 (s, 1H), 8.52 (s, 1H), 7.92 (d, J=8.4 Hz, 1H), 7.34 (s, 1H), 7.20 (d, J=8.3 Hz, 1H), 5.09-2.83 (m, 12H), 2.39 (d, J=5.0 Hz, 1H), 2.05 (d, J=5.0 Hz, 1H), 1.33-1.09 (m, 5H), 1.03-0.96 (m, 2H). LRRK2 IC$_{50}$ 0.6 nM.

The following examples in Table 7 were prepared according to General Scheme 2 and Scheme 3 above using Q.3-1 or Q.3-2 and the appropriate pyrimidine. Coupling partners are indicated in Table 7. The products were generally purified by silica gel chromatography, reverse phase prep-HPLC.

TABLE 7

Examples Prepared According to General Scheme 2 and Scheme 3

| Example | Structure Name Building Block X (Scheme X) + Building Block Y (Scheme Y) | Observed m/z [M + H]$^+$ | LRRK2 IC$_{50}$ (nM) |
|---|---|---|---|
| 3.1-2 | (S)-1-(1-(6-((R)-3-methyl-4-(oxetan-3-yl)piperazin-1-yl)pyrimidin-4-yl)-1H-indazol-6-yl)spiro[2.2]pentane-1-carbonitrile<br><br>Q.3-2 (Scheme Q) + L.7 (Table 1) | 442 | 0.6 |
| 3.2 | (S)-1-(1-(6-((3S,4S,5R)-4-hydroxy-3,4,5-trimethylpiperidin-1-yl)pyrimidin-4-yl)-1H-indazol-6-yl)spiro[2.2]pentane-1-carbonitrile<br><br>Q.3-2 (Scheme Q) + L.8 (Table 1) | 429 | 1.1 |
| 3.3 | (S)-1-(1-(6-((3S,4S,5R)-4-hydroxy-3,4,5-trimethylpiperidin-1-yl)-2-(methoxymethyl)pyrimidin-4-yl)-1H-indazol-6-yl)spiro[2.2]pentane-1-carbonitrile, TFA salt<br><br>Q.3-2 (Scheme Q) + L.14 (Table 1) | 473 | 1.0 |

TABLE 7-continued

Examples Prepared According to General Scheme 2 and Scheme 3

| Example | Building Block X (Scheme X) + Building Block Y (Scheme Y) | Observed m/z [M + H]⁺ | LRRK2 IC$_{50}$ (nM) |
|---|---|---|---|
| 3.4 | (S)-1-(1-(6-((3S,4S,5R)-4-hydroxy-3,4,5-trimethylpiperidin-1-yl)-2-methoxypyrimidin-4-yl)-1H-indazol-6-yl)spiro[2.2]pentane-1-carbonitrile, TFA salt<br><br>Q.3-2 (Scheme Q) + L.15 (Table 1) | 459 | 1.5 |
| 3.5-1 | (R)-1-(1-(6-((2S or 2R, 3R or 3S)-3-(2-hydroxypropan-2-yl)-2-methylpyrrolidin-1-yl)pyrimidin-4-yl)-1H-indazol-6-yl)spiro[2.2]pentane-1-carbonitrile<br><br>Q.3-1 (Scheme Q) + M.1-1 (Scheme M) | 429 | 122.9 |
| 3.5-2 | (S)-1-(1-(6-((2S or 2R, 3R or 3S)-3-(2-hydroxypropan-2-yl)-2-methylpyrrolidin-1-yl)pyrimidin-4-yl)-1H-indazol-6-yl)spiro[2.2]pentane-1-carbonitrile<br><br>Q.3-2 (Scheme Q) + M.1-1 (Scheme M) | 429 | 31.6 |
| 3.5-3 | (R)-1-(1-(6-((2S or 2R, 3R or 3S)-3-(2-hydroxypropan-2-yl)-2-methylpyrrolidin-1-yl)pyrimidin-4-yl)-1H-indazol-6-yl)spiro[2.2]pentane-1-carbonitrile, TFA salt<br><br>Q.3-1 (Scheme Q) + M.1-2 (Scheme M) | 429 | 1.9 |

TABLE 7-continued

Examples Prepared According to General Scheme 2 and Scheme 3

| Example | Structure / Name / Building Block X (Scheme X) + Building Block Y (Scheme Y) | Observed m/z [M + H]+ | LRRK2 IC$_{50}$ (nM) |
|---|---|---|---|
| 3.5-4 | (S)-1-(1-(6-((2S or 2R, 3R or 3S)-3-(2-hydroxypropan-2-yl)-2-methylpyrrolidin-1-yl)pyrimidin-4-yl)-1H-indazol-6-yl)spiro[2.2]pentane-1-carbonitrile, TFA salt<br><br>Q.3-2 (Scheme Q) + M.1-2 (Scheme M) | 429 | 0.6 |
| 3.5-5 | (R)-1-(1-(6-((2S or 2R, 3R or 3S)-3-(2-hydroxypropan-2-yl)-2-methylpyrrolidin-1-yl)pyrimidin-4-yl)-1H-indazol-6-yl)spiro[2.2]pentane-1-carbonitrile<br><br>Q.3-1 (Scheme Q) + M.1-3 (Scheme M) | 429 | 27.6 |
| 3.5-6 | (S)-1-(1-(6-((2S or 2R, 3R or 3S)-3-(2-hydroxypropan-2-yl)-2-methylpyrrolidin-1-yl)pyrimidin-4-yl)-1H-indazol-6-yl)spiro[2.2]pentane-1-carbonitrile<br><br>Q.3-2 (Scheme Q) + M.1-3 (Scheme M) | 429 | 4.9 |
| 3.5-7 | (R)-1-(1-(6-((2S or 2R, 3R or 3S)-3-(2-hydroxypropan-2-yl)-2-methylpyrrolidin-1-yl)pyrimidin-4-yl)-1H-indazol-6-yl)spiro[2.2]pentane-1-carbonitrile<br><br>Q.3-1 (Scheme Q) + M.1-4 (Scheme M) | 429 | 5.1 |

TABLE 7-continued

Examples Prepared According to General Scheme 2 and Scheme 3

| Example | Structure Name Building Block X (Scheme X) + Building Block Y (Scheme Y) | Observed m/z [M + H]⁺ | LRRK2 IC₅₀ (nM) |
|---|---|---|---|
| 3.5-8 | (S)-1-(1-(6-((2S or 2R, 3R or 3S)-3-(2-hydroxypropan-2-yl)-2-methylpyrrolidin-1-yl)pyrimidin-4-yl)-1H-indazol-6-yl)spiro[2.2]pentane-1-carbonitrile<br><br>Q.3-2 (Scheme Q) + M.1-4 (Scheme M) | 429 | 1.1 |
| 3.6-1 | (R)-1-(1-(6-((3S or 3R, 4R or 4S)-3-(2-hydroxypropan-2-yl)-4-methylpyrrolidin-1-yl)pyrimidin-4-yl)-1H-indazol-6-yl)spiro[2.2]pentane-1-carbonitrile, TFA salt<br><br>Q.3-1 (Scheme Q) + M.2-1 (Table 2) | 429 | 2.2 |
| 3.6-2 | (S)-1-(1-(6-((3S or 3R, 4R or 4S)-3-(2-hydroxypropan-2-yl)-4-methylpyrrolidin-1-yl)pyrimidin-4-yl)-1H-indazol-6-yl)spiro[2.2]pentane-1-carbonitrile, TFA salt<br><br>Q.3-2 (Scheme Q) + M.2-1 (Table 2) | 429 | 0.6 |
| 3.6-3 | (R)-1-(1-(6-((3S or 3R, 4R or 4S)-3-(2-hydroxypropan-2-yl)-4-methylpyrrolidin-1-yl)pyrimidin-4-yl)-1H-indazol-6-yl)spiro[2.2]pentane-1-carbonitrile, TFA salt<br><br>Q.3-1 (Scheme Q) + M.2-2 (Table 2) | 429 | 9.8 |

TABLE 7-continued

Examples Prepared According to General Scheme 2 and Scheme 3

| Example | Structure<br>Name<br>Building Block X (Scheme X) + Building Block Y (Scheme Y) | Observed m/z [M + H]⁺ | LRRK2 IC$_{50}$ (nM) |
|---|---|---|---|
| 3.6-4 | 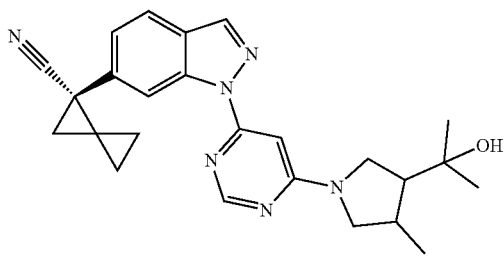<br>(S)-1-(1-(6-((3S or 3R, 4R or 4S)-3-(2-hydroxypropan-2-yl)-4-methylpyrrolidin-1-yl)pyrimidin-4-yl)-1H-indazol-6-yl)spiro[2.2]pentane-1-carbonitrile, TFA salt<br>Q.3-2 (Scheme Q) + M.2-2 (Table 2) | 429 | 2.1 |
| 3.7-1 | 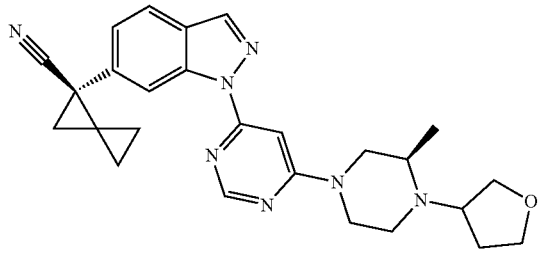<br>(R)-1-(1-(6-((R)-3-methyl-4-((R or S)-tetrahydrofuran-3-yl)piperazin-1-yl)pyrimidin-4-yl)-1H-indazol-6-yl)spiro[2.2]pentane-1-carbonitrile, TFA salt<br>Q.3-1 (Scheme Q) + O.5-1 (Scheme O) | 456 | 8.0 |
| 3.7-2 | 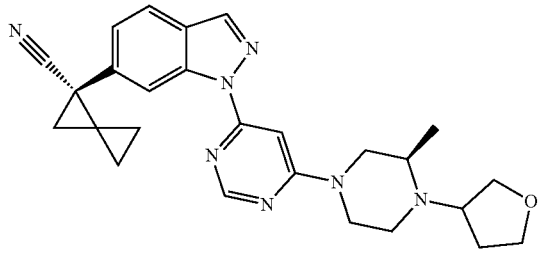<br>(S)-1-(1-(6-((R)-3-methyl-4-((R or S)-tetrahydrofuran-3-yl)piperazin-1-yl)pyrimidin-4-yl)-1H-indazol-6-yl)spiro[2.2]pentane-1-carbonitrile, TFA salt<br>Q.3-2 (Scheme Q) + O.5-1 (Scheme O) | 456 | 1.7 |

TABLE 7-continued

Examples Prepared According to General Scheme 2 and Scheme 3

| Example | Structure<br>Name<br>Building Block X (Scheme X) + Building Block Y (Scheme Y) | Observed<br>m/z [M + H]⁺ | LRRK2<br>IC$_{50}$ (nM) |
|---|---|---|---|
| 3.7-3 | (R)-1-(1-(6-((R)-3-methyl-4-((R or S)-tetrahydrofuran-3-yl)piperazin-1-yl)pyrimidin-4-yl)-1H-indazol-6-yl)spiro[2.2]pentane-1-carbonitrile, TFA salt<br><br>Q.3-1 (Scheme Q) + O.5-2 (Scheme O) | 456 | 9.0 |
| 3.7-4 | (S)-1-(1-(6-((R)-3-methyl-4-((R or S)-tetrahydrofuran-3-yl)piperazin-1-yl)pyrimidin-4-yl)-1H-indazol-6-yl)spiro[2.2]pentane-1-carbonitrile, TFA salt<br><br>Q.3-2 (Scheme Q) + O.5-2 (Scheme O) | 456 | 2.0 |
| 3.8-1 | (R)-1-(1-(6-((S)-3-methyl-4-((R or S)-tetrahydrofuran-3-yl)piperazin-1-yl)pyrimidin-4-yl)-1H-indazol-6-yl)spiro[2.2]pentane-1-carbonitrile, TFA salt<br><br>Q.3-1 (Scheme Q) + O.6-1 (Table 3) | 456 | 1.6 |

TABLE 7-continued

Examples Prepared According to General Scheme 2 and Scheme 3

| Example | Structure<br>Name<br>Building Block X (Scheme X) + Building Block Y (Scheme Y) | Observed<br>m/z [M + H]⁺ | LRRK2<br>IC₅₀ (nM) |
|---|---|---|---|
| 3.8-2 | (R)-1-(1-(6-((S)-3-methyl-4-((R or S)-tetrahydrofuran-3-yl)piperazin-1-yl)pyrimidin-4-yl)-1H-indazol-6-yl)spiro[2.2]pentane-1-carbonitrile, TFA salt<br><br>Q.3-2 (Scheme Q) + O.6-1 (Table 3) | 456 | 0.8 |
| 3.8-3 | (R)-1-(1-(6-((S)-3-methyl-4-((R or S)-tetrahydrofuran-3-yl)piperazin-1-yl)pyrimidin-4-yl)-1H-indazol-6-yl)spiro[2.2]pentane-1-carbonitrile, TFA salt<br><br>Q.3-1 (Scheme Q) + O.6-2 (Table 3) | 456 | 1.3 |
| 3.8-4 | (S)-1-(1-(6-((S)-3-methyl-4-((R or S)-tetrahydrofuran-3-yl)piperazin-1-yl)pyrimidin-4-yl)-1H-indazol-6-yl)spiro[2.2]pentane-1-carbonitrile, TFA salt<br><br>Q.3-2 (Scheme Q) + O.6-2 (Table 3) | 456 | 0.6 |

TABLE 7-continued

Examples Prepared According to General Scheme 2 and Scheme 3

| Example | Structure Name Building Block X (Scheme X) + Building Block Y (Scheme Y) | Observed m/z [M + H]+ | LRRK2 IC$_{50}$ (nM) |
|---|---|---|---|
| 3.9-1 | (R)-1-(1-(6-(6-hydroxy-6-methyl-2-azaspiro[3.3]heptan-2-yl)pyrimidin-4-yl)-1H-indazol-6-yl)spiro[2.2]pentane-1-carbonitrile, TFA salt<br>Q.3-1 (Scheme Q) + L.22 (Table 1) | 413 | 2.5 |
| 3.9-2 | (S)-1-(1-(6-(6-hydroxy-6-methyl-2-azaspiro[3.3]heptan-2-yl)pyrimidin-4-yl)-1H-indazol-6-yl)spiro[2.2]pentane-1-carbonitrile, TFA salt<br>Q.3-2 (Scheme Q) + L.22 (Table 1) | 413 | 1.5 |
| 3.10-1 | (R)-1-(1-(6-((R or S)-3-(2-hydroxypropan-2-yl)-3-methoxypyrrolidin-1-yl)pyrimidin-4-yl)-1H-indazol-6-yl)spiro[2.2]pentane-1-carbonitrile, TFA salt<br>Q.3-1 (Scheme Q) + M.3-1 (Table 2) | 445 | 15.1 |
| 3.10-2 | (S)-1-(1-(6-((R or S)-3-(2-hydroxypropan-2-yl)-3-methoxypyrrolidin-1-yl)pyrimidin-4-yl)-1H-indazol-6-yl)spiro[2.2]pentane-1-carbonitrile, TFA salt<br>Q.3-2 (Scheme Q) + M.3-1 (Table 2) | 445 | 2.1 |

TABLE 7-continued

Examples Prepared According to General Scheme 2 and Scheme 3

| Example | Building Block X (Scheme X) + Building Block Y (Scheme Y) Structure Name | Observed m/z [M + H]⁺ | LRRK2 IC₅₀ (nM) |
|---|---|---|---|
| 3.10-3 | (R)-1-(1-(6-((R or S)-3-(2-hydroxypropan-2-yl)-3-methoxypyrrolidin-1-yl)pyrimidin-4-yl)-1H-indazol-6-yl)spiro[2.2]pentane-1-carbonitrile, TFA salt<br>Q.3-1 (Scheme Q) + M.3-2 (Table 2) | 445 | 3.1 |
| 3.10-4 | (S)-1-(1-(6-((R or S)-3-(2-hydroxypropan-2-yl)-3-methoxypyrrolidin-1-yl)pyrimidin-4-yl)-1H-indazol-6-yl)spiro[2.2]pentane-1-carbonitrile, TFA salt<br>Q.3-2 (Scheme Q) + M.3-2 (Table 2) | 445 | 0.9 |
| 3.11-1 | (R)-1-(1-(6-((R or S)-7-hydroxy-5-azaspiro[2.4]heptan-5-yl)pyrimidin-4-yl)-1H-indazol-6-yl)spiro[2.2]pentane-1-carbonitrile, TFA salt<br>Q.3-1 (Scheme Q) + N.5-1 (Scheme N) | 399 | 6.7 |
| 3.11-2 | (S)-1-(1-(6-((R or S)-7-hydroxy-5-azaspiro[2.4]heptan-5-yl)pyrimidin-4-yl)-1H-indazol-6-yl)spiro[2.2]pentane-1-carbonitrile, TFA salt<br>Q.3-2 (Scheme Q) + N.5-1 (Scheme N) | 399 | 1.4 |

TABLE 7-continued

Examples Prepared According to General Scheme 2 and Scheme 3

| Example | Building Block X (Scheme X) + Building Block Y (Scheme Y) / Structure Name | Observed m/z [M + H]+ | LRRK2 IC$_{50}$ (nM) |
|---|---|---|---|
| 3.11-3 | (R)-1-(1-(6-((R or S)-7-hydroxy-5-azaspiro[2.4]heptan-5-yl)pyrimidin-4-yl)-1H-indazol-6-yl)spiro[2.2]pentane-1-carbonitrile, TFA salt<br>Q.3-1 (Scheme Q) + N.5-2 (Scheme N) | 399 | 6.3 |
| 3.11-4 | (S)-1-(1-(6-((R or S)-7-hydroxy-5-azaspiro[2.4]heptan-5-yl)pyrimidin-4-yl)-1H-indazol-6-yl)spiro[2.2]pentane-1-carbonitrile, TFA salt<br>Q.3-2 (Scheme Q) + N.5-2 (Scheme N) | 399 | 0.6 |

Preparation of Example 1.4-2, (S)-1-(1-(6-((R)-3-(2-hydroxypropan-2-yl)pyrrolidin-1-yl)pyrimidin-4-yl)-1H-indazol-6-yl)spiro[2.2]pentane-1-carbonitrile Scheme 4

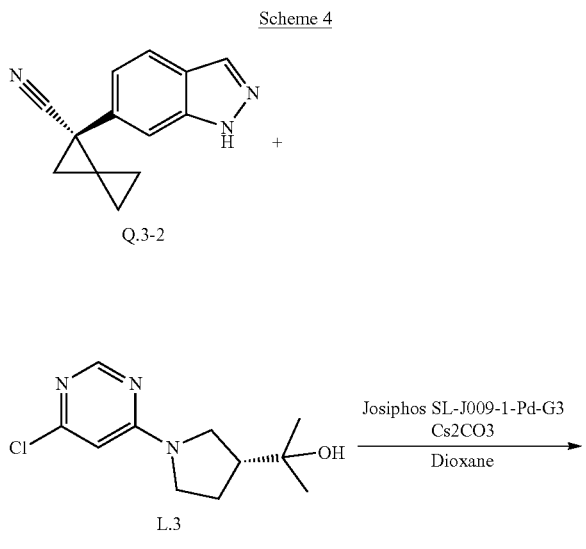

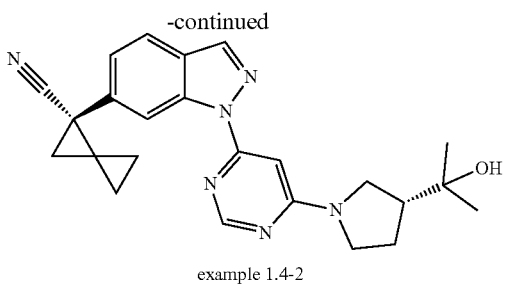

example 1.4-2

Enantiomerically pure (S)-1-(1H-indazol-6-yl)spiro[2.2]pentane-1-carbonitrile (Q.3-2) (250 mg, 1.20 mmol), (R)-2-(1-(6-chloropyrimidin-4-yl)pyrrolidin-3-yl)propan-2-ol (289 mg, 1.20 mmol) (L.3), cesium carbonate (584 mg, 1.80 mmol) and Josiphos SL-J009-1-Pd-G3 (110 mg, 0.12 mmol) were charged in a 2 mL microwave vial. The vial was evacuated and backfilled with argon (3×), dioxane (6.0 mL) was added, and the reaction was heated to 50° C. overnight. The reaction was cooled to room temperature, diluted with EtOAc (5 mL), filtered over a pad of Celite®, and concentrated. The crude material was purified by silica gel column chromatography (gradient elution: 0-100% (3:1 EtOAc:EtOH)/hexanes) to provide (S)-1-(1-(6-((R)-3-(2-hydroxypropan-2-yl)pyrrolidin-1-yl)pyrimidin-4-yl)-1H-indazol-6-yl)spiro[2.2]pentane-1-carbonitrile. MS (ESI) m/z calc'd for $C_{24}H_{24}N_6O$ [M+H]+ 415 found 415. $^1$H NMR (499 MHz, DMSO-d$_6$) δ 8.92 (s, 1H), 8.50 (s, 1H), 8.46 (s, 1H), 7.89 (d, J=8.4 Hz, 1H), 7.17 (d, J=8.3 Hz, 1H), 6.83 (s, 1H), 4.43 (s, 1H), 3.95-3.82 (m, 1H), 3.77-3.67 (m, 1H), 3.60-3.52 (m, 1H), 3.47-3.40 (m, 1H), 2.37 (d, J=5.0 Hz, 1H), 2.29-2.20 (m, 1H), 2.04 (d, J=5.0 Hz, 1H), 1.98-1.79 (m, 2H), 1.31-1.20 (m, 3H), 1.18-1.13 (m, 6H), 1.04-0.97 (m, 1H). LRRK2 IC$_{50}$ 0.9 nM.

The following examples in Table 8 were made according to General scheme 2 and Scheme 4 above. Unless stated otherwise intermediate Q.3-2 was used and combined with the appropriate pyrimidine. The compounds were generally purified by silica gel chromatography, reverse phase prep-HPLC and SFC. Where isomers were separated by SFC, conditions are provided after the table.

TABLE 8

Examples Prepared According to General Scheme 2 and Scheme 4

| Example | Structure Name | Observed m/z [M + H]$^+$ | LRRK2 IC$_{50}$ (nM) |
| --- | --- | --- | --- |
| 4.1 | (S)-1-(1-(6-((3S,5R)-3,5-dimethyl-4-(oxetan-3-yl)piperazin-1-yl)pyrimidin-4-yl)-1H-indazol-6-yl)spiro[2.2]pentane-1-carbonitrile, TFA salt | 456 | 0.6 |
| 4.2 | (S)-1-(1-(6-(3-hydroxy-3-methylazetidin-1-yl)pyrimidin-4-yl)-1H-indazol-6-yl)spiro[2.2]pentane-1-carbonitrile | 373 | 1.3 |
| 4.3-1 | (S)-1-(1-(6-((R or S)-2-(2-hydroxypropan-2-yl)morpholino)pyrimidin-4-yl)-1H-indazol-6-yl)spiro[2.2]pentane-1-carbonitrile | 431 | 1.8 |
| 4.3-2 | (S)-1-(1-(6-((R or S)-2-(2-hydroxypropan-2-yl)morpholino)pyrimidin-4-yl)-1H-indazol-6-yl)spiro[2.2]pentane-1-carbonitrile | 431 | 0.6 |

TABLE 8-continued

Examples Prepared According to General Scheme 2 and Scheme 4

| Example | Structure Name | Observed m/z [M + H]+ | LRRK2 IC50 (nM) |
|---|---|---|---|
| 4.4 | 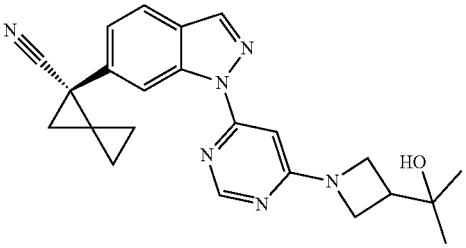<br>(S)-1-(1-(6-(3-(2-hydroxypropan-2-yl)azetidin-1-yl)pyrimidin-4-yl)-1H-indazol-6-yl)spiro[2.2]pentane-1-carbonitrile | 401 | 0.6 |
| 4.5 | 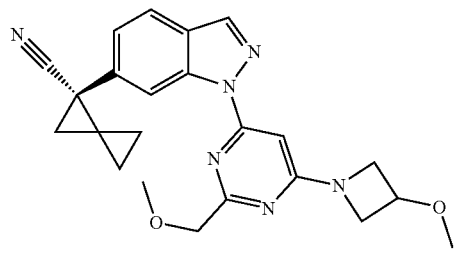<br>(S)-1-(1-(6-(3-methoxyazetidin-1-yl)-2-(methoxymethyl)pyrimidin-4-yl)-1H-indazol-6-yl)spiro[2.2]pentane-1-carbonitrile | 417 | 2.6 |
| 4.6 | 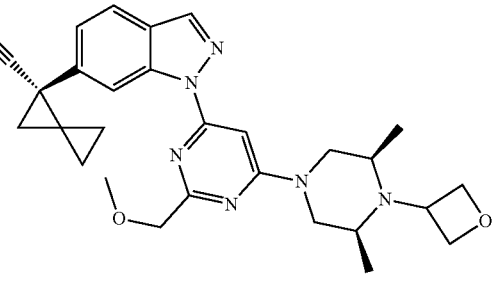<br>(S)-1-(1-(6-((3S,5R)-3,5-dimethyl-4-(oxetan-3-yl)piperazin-1-yl)-2-(methoxymethyl)pyrimidin-4-yl)-1H-indazol-6-yl)spiro[2.2]pentane-1-carbonitrile | 500 | 0.9 |
| 4.7 | 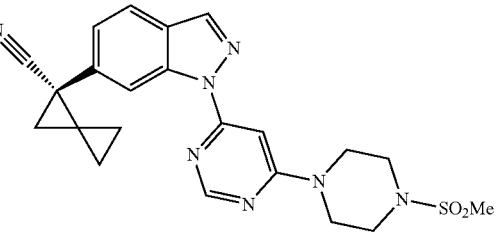<br>(S)-1-(1-(6-(4-(methylsulfonyl)piperazin-1-yl)pyrimidin-4-yl)-1H-indazol-6-yl)spiro[2.2]pentane-1-carbonitrile, TFA salt | 450 | 1.3 |

TABLE 8-continued

Examples Prepared According to General Scheme 2 and Scheme 4

| Example | Structure Name | Observed m/z [M + H]⁺ | LRRK2 IC$_{50}$ (nM) |
|---|---|---|---|
| 4.8 | 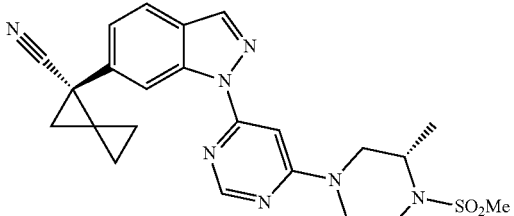<br>(S)-1-(1-(6-((S)-3-methyl-4-(methylsulfonyl)piperazin-1-yl)pyrimidin-4-yl)-1H-indazol-6-yl)spiro[2.2]pentane-1-carbonitrile | 464 | 1.2 |
| 4.9-1 | 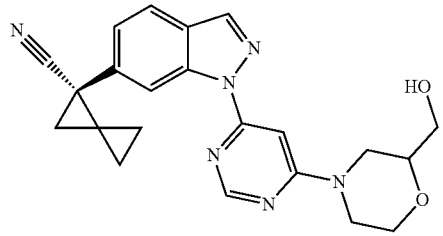<br>(S)-1-(1-(6-((R or S)-2-(hydroxymethyl)morpholino)pyrimidin-4-yl)-1H-indazol-6-yl)spiro[2.2]pentane-1-carbonitrile | 403 | 0.6 |
| 4.9-2 | 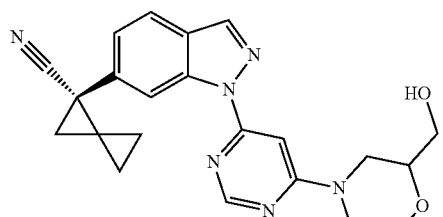<br>(S)-1-(1-(6-((R or S)-2-(hydroxymethyl)morpholino)pyrimidin-4-yl)-1H-indazol-6-yl)spiro[2.2]pentane-1-carbonitrile | 403 | 0.6 |
| 4.10 | 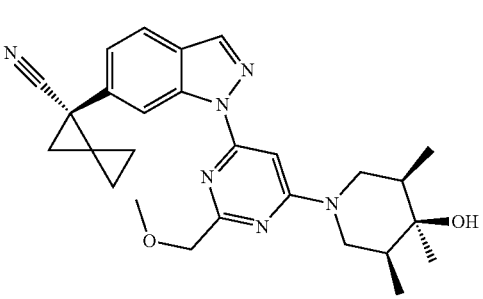<br>(S)-1-(1-(6-((3S,4S,5R)-4-hydroxy-3,4,5-trimethylpiperidin-1-yl)-2-(methoxymethyl)pyrimidin-4-yl)-1H-indazol-6-yl)spiro[2.2]pentane-1-carbonitrile | 473 | 0.6 |

TABLE 8-continued

Examples Prepared According to General Scheme 2 and Scheme 4

| Example | Structure Name | Observed m/z [M + H]+ | LRRK2 IC50 (nM) |
|---|---|---|---|
| 4.11-1 | 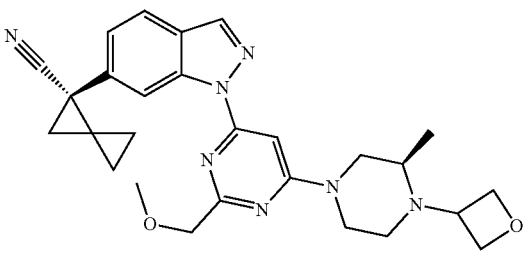 (S)-1-(1-(2-(methoxymethyl)-6-((R)-3-methyl-4-(oxetan-3-yl)piperazin-1-yl)pyrimidin-4-yl)-1H-indazol-6-yl)spiro[2.2]pentane-1-carbonitrile,TFA salt | 486 | 1.3 |
| 4.11-2 | 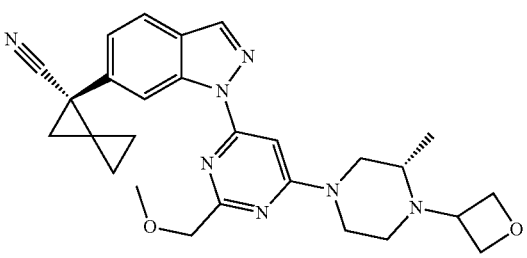 (S)-1-(1-(2-(methoxymethyl)-6-((S)-3-methyl-4-(oxetan-3-yl)piperazin-1-yl)pyrimidin-4-yl)-1H-indazol-6-yl)spiro[2.2]pentane-1-carbonitrile,TFA salt | 486 | 0.7 |
| 4.12-1 | 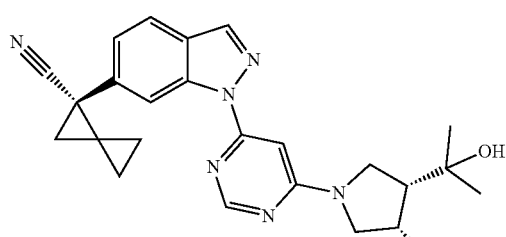 (S)-1-(1-(6-((3S,4R or 4S, 3R)-3-fluoro-4-(2-hydroxypropan-2-yl)pyrrolidin-1-yl)pyrimidin-4-yl)-1H-indazol-6-yl)spiro[2.2]pentane-1-carbonitrile | 433 | 1.2 |
| 4.12-2 | 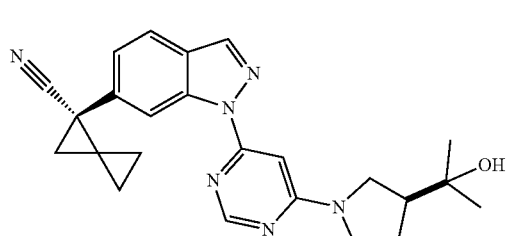 (S)-1-(1-(6-((3S,4R or 4S, 3R)-3-fluoro-4-(2-hydroxypropan-2-yl)pyrrolidin-1-yl)pyrimidin-4-yl)-1H-indazol-6-yl)spiro[2.2]pentane-1-carbonitrile | 433 | 0.6 |

TABLE 8-continued

Examples Prepared According to General Scheme 2 and Scheme 4

| Example | Structure Name | Observed m/z [M + H]+ | LRRK2 IC50 (nM) |
|---|---|---|---|
| 4.13 | 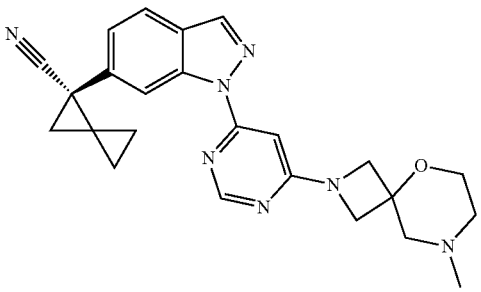<br>(S)-1-(1-(6-(8-methyl-5-oxa-2,8-diazaspiro[3.5]nonan-2-yl)pyrimidin-4-yl)-1H-indazol-6-yl)spiro[2.2]pentane-1-carbonitrile | 428 | 0.6 |
| 4.14 | 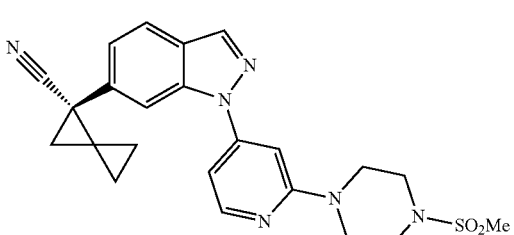<br>(S)-1-(1-(2-(4-(methylsulfonyl)piperazin-1-yl)pyridin-4-yl)-1H-indazol-6-yl)spiro[2.2]pentane-1-carbonitrile | 449 | 2.8 |
| 4.15-1 | 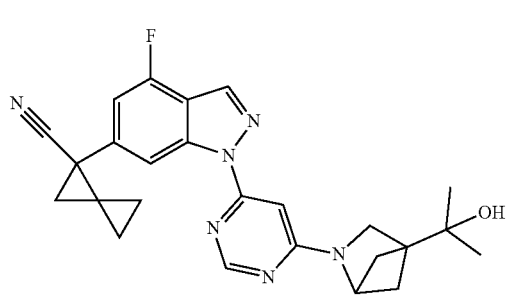<br>(R or S)-1-(4-fluoro-1-(6-(4-(2-hydroxypropan-2-yl)-2-azabicyclo[2.1.1]hexan-2-yl)pyrimidin-4-yl)-1H-indazol-6-yl)spiro[2.2]pentane-1-carbonitrile<br>S.3-1 (Scheme S) used | 445 | 18.4 |
| 4.15-2 | 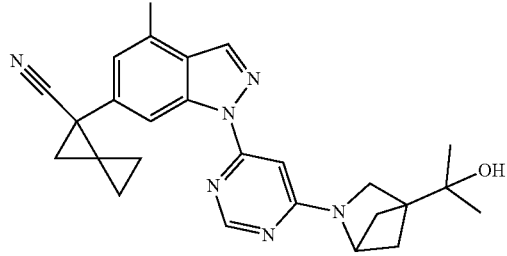<br>(R or S)-1-(4-fluoro-1-(6-(4-(2-hydroxypropan-2-yl)-2-azabicyclo[2.1.1]hexan-2-yl)pyrimidin-4-yl)-1H-indazol-6-yl)spiro[2.2]pentane-1-carbonitrile<br>S.3-2 (Scheme S) used | 445 | 2.3 |

TABLE 8-continued

Examples Prepared According to General Scheme 2 and Scheme 4

| Example | Structure Name | Observed m/z [M + H]+ | LRRK2 IC$_{50}$ (nM) |
|---|---|---|---|
| 4.16 | 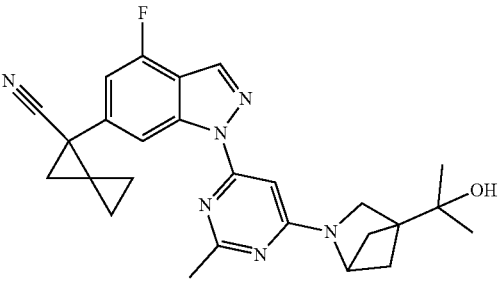<br>(R or S)-1-(4-fluoro-1-(6-(4-(2-hydroxypropan-2-yl)-2-azabicyclo[2.1.1]hexan-2-yl)-2-methylpyrimidin-4-yl)-1H-indazol-6-yl)spiro[2.2]pentane-1-carbonitrile<br>S.3-2 (Scheme S) used | 459 | 0.6 |
| 4.17 | 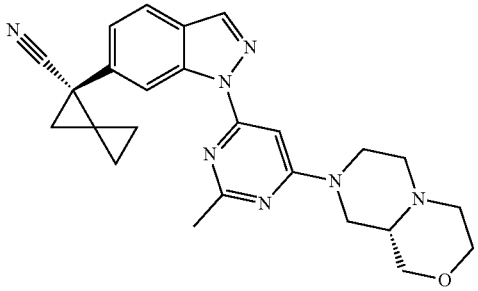<br>(S)-1-(1-(6-((S)-hexahydropyrazino[2,1-c][1,4]oxazin-8(1H)-yl)-2-methylpyrimidin-4-yl)-1H-indazol-6-yl)spiro[2.2]pentane-1-carbonitrile | 442 | 0.6 |
| 4.18 | 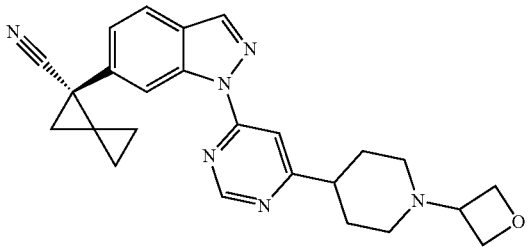<br>(S)-1-(1-(6-(1-(oxetan-3-yl)piperidin-4-yl)pyrimidin-4-yl)-1H-indazol-6-yl)spiro[2.2]pentane-1-carbonitrile | 427 | 18.7 |
| 4.19 | 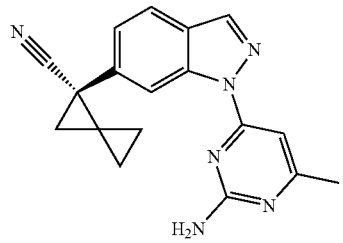<br>(S)-1-(1-(2-amino-6-methylpyrimidin-4-yl)-1H-indazol-6-yl)spiro[2.2]pentane-1-carbonitrile | 317 | 0.6 |

TABLE 8-continued

Examples Prepared According to General Scheme 2 and Scheme 4

| Example | Structure Name | Observed m/z [M + H]+ | LRRK2 IC$_{50}$ (nM) |
|---|---|---|---|
| 4.20 | 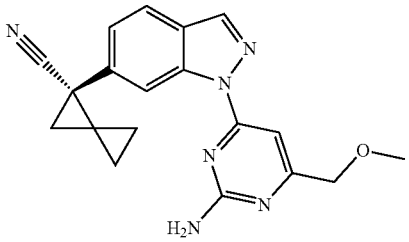 1-(1-(2-amino-6-(methoxymethyl)pyrimidin-4-yl)-1H-indazol-6-yl)spiro[2.2]pentane-1-carbonitrile | 547 | 0.6 |
| 4.21 | 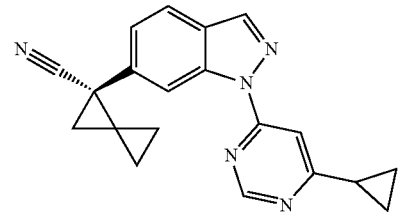 (S)-1-(1-(6-cyclopropylpyrimidin-4-yl)-1H-indazol-6-yl)spiro[2.2]pentane-1-carbonitrile | 328 | 6.5 |
| 4.22 | 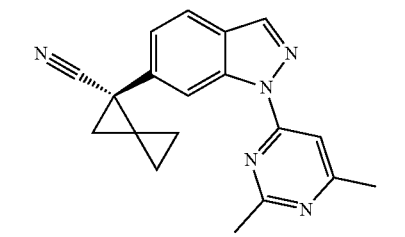 (S)-1-(1-(2,6-dimethylpyrimidin-4-yl)-1H-indazol-6-yl)spiro[2.2]pentane-1-carbonitrile | 316 | 5.2 |
| 4.23 | 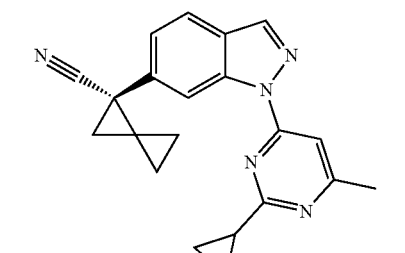 (S)-1-(1-(2-cyclopropyl-6-methylpyrimidin-4-yl)-1H-indazol-6-yl)spiro[2.2]pentane-1-carbonitrile | 342 | 3.2 |

TABLE 8-continued

Examples Prepared According to General Scheme 2 and Scheme 4

| Example | Structure Name | Observed m/z [M + H]$^+$ | LRRK2 IC$_{50}$ (nM) |
|---|---|---|---|
| 4.24 | 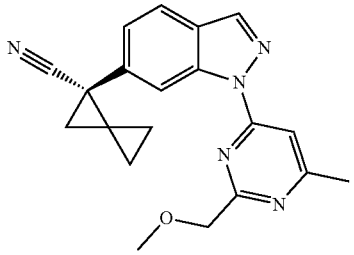<br>(S)-1-(1-(2-(methoxymethyl)-6-methylpyrimidin-4-yl)-1H-indazol-6-yl)spiro[2.2]pentane-1-carbonitrile | 346 | 10.3 |
| 4.25 | 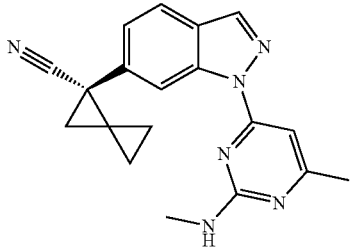<br>(S)-1-(1-(6-methyl-2-(methylamino)pyrimidin-4-yl)-1H-indazol-6-yl)spiro[2.2]pentane-1-carbonitrile | 331 | 3.5 |
| 4.26 | 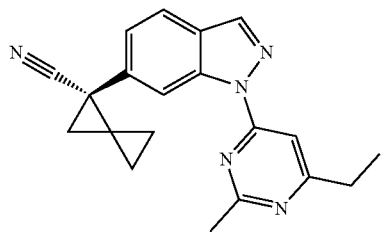<br>(S)-1-(1-(6-ethyl-2-methylpyrimidin-4-yl)-1H-indazol-6-yl)spiro[2.2]pentane-1-carbonitrile | 330 | 3.1 |
| 4.27 | 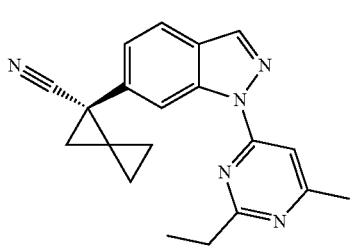<br>(S)-1-(1-(2-ethyl-6-methylpyrimidin-4-yl)-1H-indazol-6-yl)spiro[2.2]pentane-1-carbonitrile | 330 | 3.2 |

TABLE 8-continued

Examples Prepared According to General Scheme 2 and Scheme 4

| Example | Structure Name | Observed m/z [M + H]⁺ | LRRK2 IC₅₀ (nM) |
|---|---|---|---|
| 4.28 | 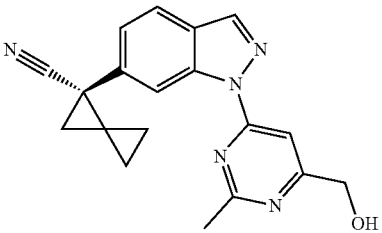<br>(S)-1-(1-(6-(hydroxymethyl)-2-methylpyrimidin-4-yl)-1H-indazol-6-yl)spiro[2.2]pentane-1-carbonitrile | 331 | 0.625 |
| 4.29 | 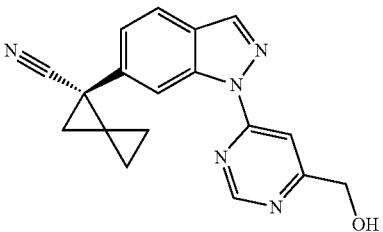<br>(S)-1-(1-(6-(hydroxymethyl)pyrimidin-4-yl)-1H-indazol-6-yl)spiro[2.2]pentane-1-carbonitrile | 317 | 5.2 |
| 4.30 | 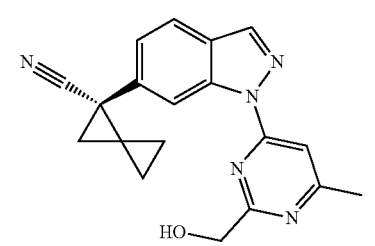<br>(S)-1-(1-(2-(hydroxymethyl)-6-methylpyrimidin-4-yl)-1H-indazol-6-yl)spiro[2.2]pentane-1-carbonitrile | 331 | 0.625 |

Example 4.3-1/4.3-2

1-(1-(6-(2-(2-hydroxypropan-2-yl)morpholino)pyrimidin-4-yl)-1H-indazol-6-yl)spiro[2.2]pentane-1-carbonitrile was purified by CHIRAL-Prep-SFC [Column: CCOF4, 21×250 mm; 20%(0.25% DMEA MeOH)/CO$_2$; Flow rate: 70 mL/min; 220 nm; RT1:5.1 min (4.3-1); RT2: 5.6 min (4.3-2)].

Example 4.9-1/4.9-2

1-(1-(6-(2-(hydroxymethyl)morpholino)pyrimidin-4-yl)-1H-indazol-6-yl)spiro[2.2]pentane-1-carbonitrile was purified by CHIRAL-Prep-SFC [Column: CCA, 21×250 mm; 30%(0.25% DMEA MeOH)/CO$_2$; Flow rate: 70 mL/min; 220 nm; RT1:4.8 (4.9-1) min; RT2: 5.6 min (4.9-2)].

Preparation of Example 5.1-1 and 5.1-2, (R or S)-1-(1-(6-(4-(2-hydroxypropan-2-yl)-2-azabicyclo[2.1.1]hexan-2-yl)pyrimidin-4-yl)-1H-indazol-6-yl)spiro[2.2]pentane-1-carbonitrile

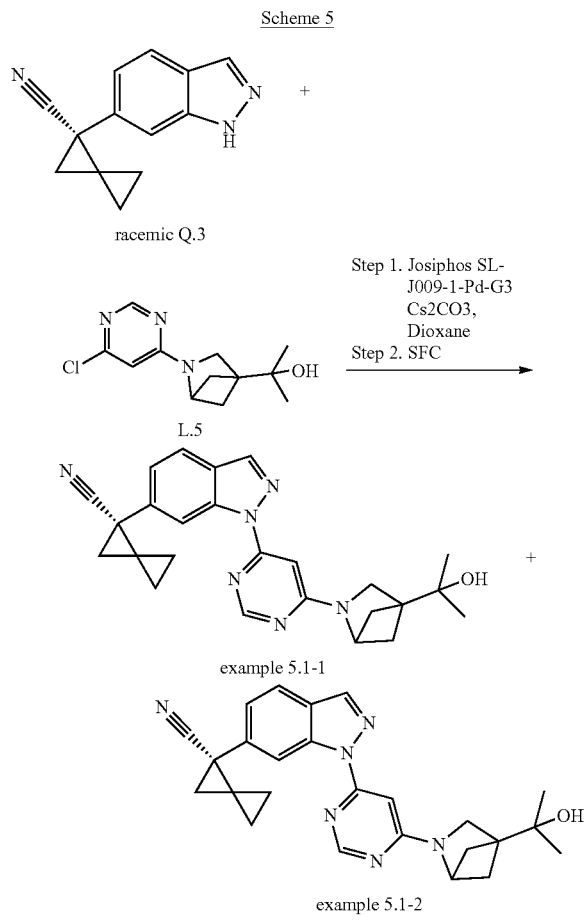

Scheme 5 racemic Q.3

Step 1. Josiphos SL-J009-1-Pd-G3
Cs2CO3,
Dioxane
Step 2. SFC

L.5 example 5.1-1 example 5.1-2

Step 1—Synthesis of Example 5.1, 1-(1-(6-(4-(2-hydroxypropan-2-yl)-2-azabicyclo[2.1.1]hexan-2-yl)pyrimidin-4-yl)-1H-indazol-6-yl)spiro[2.2]pentane-1-carbonitrile Racemic 1-(1H-indazol-6-yl)spiro[2.2]pentane-1-carbonitrile (Q.3) (1.95 g, 9.32 mmol), 2-(2-(6-chloropyrimidin-4-yl)-2-azabicyclo[2.1.1]hexan-4-yl)propan-2-ol (2.37 g, 9.32 mmol) (G.5), cesium carbonate (4.55 g, 14.0 mmol) and Josiphos SL-J009-1-Pd-G3 (110 mg, 0.12 mmol) were charged in a 300 mL schlenk flask. The vessel was evacuated and backfilled with argon (3×), dioxane (47 mL) was added and the reaction was heated to 50° C. overnight. The reaction was cooled to room temperature, diluted with EtOAc (50 mL), filtered over a pad of Celite®, and concentrated. The crude material was purified by silica gel column chromatography (gradient elution: 0-100% EtOAc)/hexanes). LCMS [method B; RT=0.92 min; (ESI) m/z calc'd for $C_{25}H_{27}N_6O$ [M+H]$^+$ 427 found 427].

Step 2—Resolution of 1-(1-(6-(4-(2-hydroxypropan-2-yl)-2-azabicyclo[2.1.1]hexan-2-yl)pyrimidin-4-yl)-1H-indazol-6-yl)spiro[2.2]pentane-1-carbonitrile The material from above was further purified by CHIRAL-Prep-SFC [Column: AD-H; 45%(0.25% DMEA EtOH)/CO$_2$; Flow rate: 70 mL/min; 254 nm; RT1:4.95 min (5.1-1); RT2: 8.70 min (5.1-2)].

Example 5.1-1-(R or S)-1-(1-(6-(4-(2-hydroxypropan-2-yl)-2-azabicyclo[2.1.1]hexan-2-yl)pyrimidin-4-yl)-1H-indazol-6-yl)spiro[2.2]pentane-1-carbonitrile MS (ESI) m/z calc'd for $C_{25}H_{27}N_6O$ [M+H]$^+$ 427 found 427]. $^1$H NMR (499 MHz, DMSO-d$_6$) δ 8.89 (s, 1H), 8.46 (s, 1H), 8.42 (s, 1H), 7.86 (d, J=8.4 Hz, 1H), 7.15 (d, J=8.3 Hz, 1H), 7.07-6.70 (m, 1H), 4.93 (s, 1H), 4.67-4.36 (m, 2H), 3.46-3.35 (m, 1H), 2.36 (d, J=4.8 Hz, 1H), 2.01 (d, J=4.8 Hz, 1H), 1.96-1.87 (m, 2H), 1.50-1.35 (m, 2H), 1.31-1.18 (m, 3H), 1.19-1.11 (m, 6H), 1.07-0.94 (m, 1H). LRRK2 IC$_{50}$ 0.9 nM

Example 5.1-2-(R or S)-1-(1-(6-(4-(2-hydroxypropan-2-yl)-2-azabicyclo[2.1.1]hexan-2-yl)pyrimidin-4-yl)-1H-indazol-6-yl)spiro[2.2]pentane-1-carbonitrile MS (ESI) m/z calc'd for $C_{25}H_{27}N_6O$ [M+H]$^+$ 427 found 427]. $^1$H NMR (499 MHz, DMSO-d$_6$) δ 8.89 (s, 1H), 8.46 (s, 1H), 8.42 (s, 1H), 7.86 (d, J=8.4 Hz, 1H), 7.15 (d, J=8.3 Hz, 1H), 7.07-6.70 (m, 1H), 4.93 (s, 1H), 4.67-4.36 (m, 2H), 3.46-3.35 (m, 1H), 2.36 (d, J=4.8 Hz, 1H), 2.01 (d, J=4.8 Hz, 1H), 1.96-1.87 (m, 2H), 1.50-1.35 (m, 2H), 1.31-1.18 (m, 3H), 1.19-1.11 (m, 6H), 1.07-0.94 (m, 1H). LRRK2 IC$_{50}$ 0.1 nM The following compounds in Table 8 were prepared according to General Scheme 2 and Scheme 5 above using racemic-Q.3, racemic-T.3, and racemic-R.3. The compounds were generally purified by silica gel chromatography, reverse phase prep-HPLC and SFC. Where isomers were separated SFC conditions are provided following the table.

TABLE 9

Compounds Prepared According to General Scheme 2 and Scheme 5

| Example | Structure Name | Observed m/z [M + H]⁺ | LRRK2 IC₅₀ (nM) |
|---|---|---|---|
| 5.2-1 | 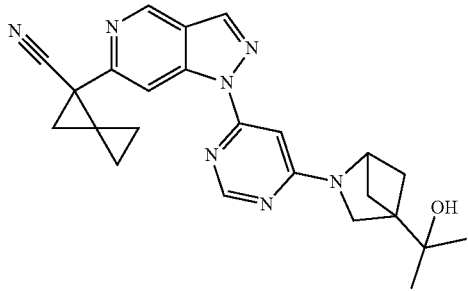<br>((R or S)-1-(1-(6-(4-(2-hydroxypropan-2-yl)-2-azabicyclo[2.1.1]hexan-2-yl)pyrimidin-4-yl)-1H-pyrazolo[4,3-c]pyridin-6-yl)spiro[2.2]pentane-1-carbonitrile | 428 | 9.2 |
| 5.2-2 | 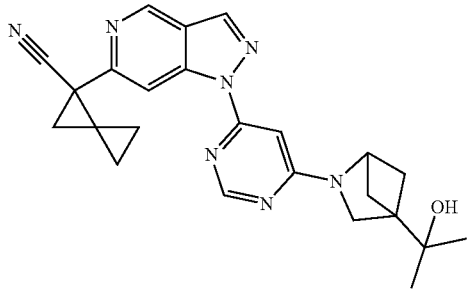<br>((R or S)-1-(1-(6-(4-(2-hydroxypropan-2-yl)-2-azabicyclo[2.1.1]hexan-2-yl)pyrimidin-4-yl)-1H-pyrazolo[4,3-c]pyridin-6-yl)spiro[2.2]pentane-1-carbonitrile | 428 | 1.7 |
| 5.3-1 | 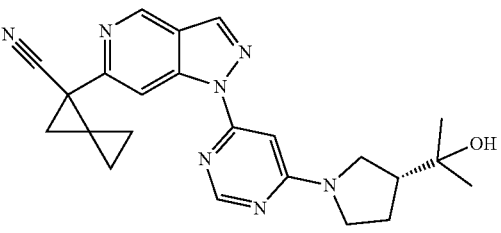<br>(R or S)-1-(1-(6-((R)-3-(2-hydroxypropan-2-yl)pyrrolidin-1-yl)pyrimidin-4-yl)-1H-pyrazolo[4,3-c]pyridin-6-yl)spiro[2.2]pentane-1-carbonitrile | 416 | 7.5 |
| 5.3-2 | 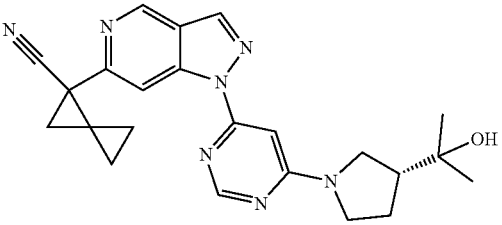<br>(R or S)-1-(1-(6-((R)-3-(2-hydroxypropan-2-yl)pyrrolidin-1-yl)pyrimidin-4-yl)-1H-pyrazolo[4,3-c]pyridin-6-yl)spiro[2.2]pentane-1-carbonitrile | 416 | 0.7 |

TABLE 9-continued

Compounds Prepared According to General Scheme 2 and Scheme 5

| Example | Structure Name | Observed m/z [M + H]$^+$ | LRRK2 IC$_{50}$ (nM) |
|---|---|---|---|
| 5.4-1 | 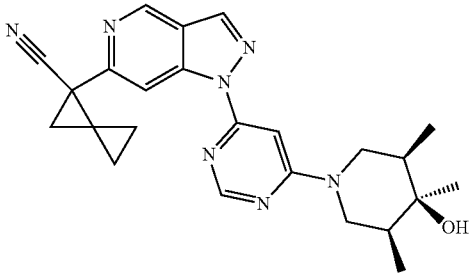<br>(R or S)-1-(1-(6-((3S,4S,5R)-4-hydroxy-3,4,5-trimethylpiperidin-1-yl)pyrimidin-4-yl)-1H-pyrazolo[4,3-c]pyridin-6-yl)spiro[2.2]pentane-1-carbonitrile | 430 | 15.0 |
| 5.4-2 | 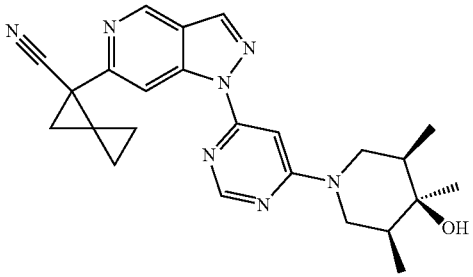<br>(R or S)-1-(1-(6-((3S,4S,5R)-4-hydroxy-3,4,5-trimethylpiperidin-1-yl)pyrimidin-4-yl)-1H-pyrazolo[4,3-c]pyridin-6-yl)spiro[2.2]pentane-1-carbonitrile | 430 | 2.6 |
| 5.5-1 | 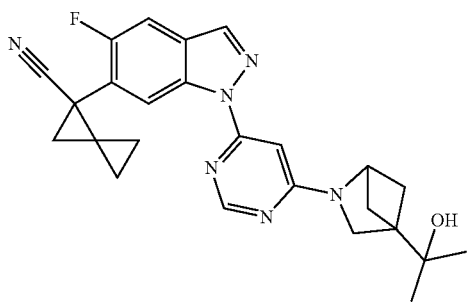<br>(R or S)-1-(5-fluoro-1-(6-(4-(2-hydroxypropan-2-yl)-2-azabicyclo[2.1.1]hexan-2-yl)pyrimidin-4-yl)-1H-indazol-6-yl)spiro[2.2]pentane-1-carbonitrile | 445 | 3.9 |

TABLE 9-continued

Compounds Prepared According to General Scheme 2 and Scheme 5

| Example | Structure Name | Observed m/z [M + H]+ | LRRK2 IC$_{50}$ (nM) |
|---|---|---|---|
| 5.5-2 | (R or S)-1-(5-fluoro-1-(6-(4-(2-hydroxypropan-2-yl)-2-azabicyclo[2.1.1]hexan-2-yl)pyrimidin-4-yl)-1H-indazol-6-yl)spiro[2.2]pentane-1-carbonitrile | 445 | 31.6 |
| 5.6-1 | (R or S)-1-(5-fluoro-1-(6-(4-(2-hydroxypropan-2-yl)-2-azabicyclo[2.1.1]hexan-2-yl)-2-methylpyrimidin-4-yl)-1H-indazol-6-yl)spiro[2.2]pentane-1-carbonitrile | 459 | 20.9 |
| 5.6-2 | (R or S)-1-(5-fluoro-1-(6-(4-(2-hydroxypropan-2-yl)-2-azabicyclo[2.1.1]hexan-2-yl)-2-methylpyrimidin-4-yl)-1H-indazol-6-yl)spiro[2.2]pentane-1-carbonitrile | 459 | 1.3 |

TABLE 9-continued
Compounds Prepared According to General Scheme 2 and Scheme 5
| Example | Structure Name | Observed m/z [M + H]+ | LRRK2 IC$_{50}$ (nM) |
|---|---|---|---|
| 5.7-1 | 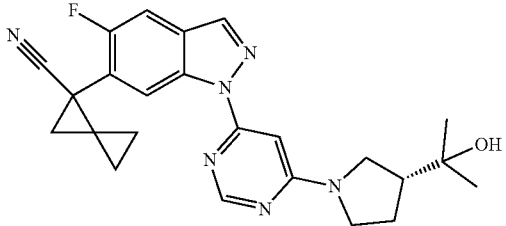<br>(R or S)-1-(5-fluoro-1-(6-((R)-3-(2-hydroxypropan-2-yl)pyrrolidin-1-yl)pyrimidin-4-yl)-1H-indazol-6-yl)spiro[2.2]pentane-1-carbonitrile | 433 | 21.7 |
| 5.7-2 | 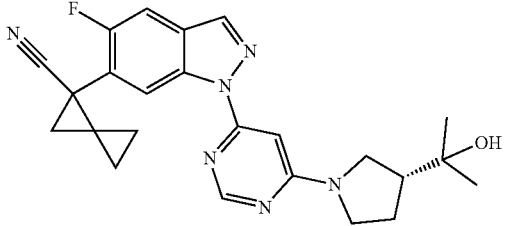<br>(R or S)-1-(5-fluoro-1-(6-((R)-3-(2-hydroxypropan-2-yl)pyrrolidin-1-yl)pyrimidin-4-yl)-1H-indazol-6-yl)spiro[2.2]pentane-1-carbonitrile | 433 | 2.6 |

Example 5.2-1/5.2-2

1-(1-(6-(4-(2-hydroxypropan-2-yl)-2-azabicyclo[2.1.1]hexan-2-yl)pyrimidin-4-yl)-1H-pyrazolo[4,3-c]pyridin-6-yl)spiro[2.2]pentane-1-carbonitrile was purified via CHIRAL-Prep-SFC [Column: CCA, 21×250 mm; 30% MeOH with 0.25% DMEA/CO$_2$; Flow rate: 70 mL/min; 254 nm; RT1: 3.5 min (5.2-1); RT2: 5.4 min (5.2-2)].

Example 5.3-1/5.3-2

1-(1-(6-((R)-3-(2-hydroxypropan-2-yl)pyrrolidin-1-yl)pyrimidin-4-yl)-1H-pyrazolo[4,3-c]pyridin-6-yl)spiro[2.2]pentane-1-carbonitrile was purified via CHIRAL-Prep-SFC [Column: Lux-2, 21×250 mm; 40% Isopropanol with 0.25% DMEA/CO$_2$; Flow rate: 70 mL/min; 240 nm; RT1: 3.5 min (5.3-1); RT2: 4.1 min (5.3-2)].

Example 5.4-1/5.4-2

1-(1-(6-((3S,4s,5R)-4-hydroxy-3,4,5-trimethylpiperidin-1-yl)pyrimidin-4-yl)-1H-pyrazolo[4,3-c]pyridin-6-yl)spiro[2.2]pentane-1-carbonitrile was purified via CHIRAL-Prep-SFC [Column: CCC, 21×250 mm; 25% 2-propanol with 0.25% DMEA/CO$_2$; Flow rate: 70 mL/min; 254 nm; RT1: 4.3 min (5.4-1); RT2: 5.3 min (5.4-2)].

Example 5.5-1/5.5-2

1-(5-fluoro-1-(6-(4-(2-hydroxypropan-2-yl)-2-azabicyclo[2.1.1]hexan-2-yl)pyrimidin-4-yl)-1H-indazol-6-yl)spiro[2.2]pentane-1-carbonitrile was purified via CHIRAL-Prep-SFC [Column: OJ-H, 21×250 mm; 15% Methanol with 0.25% DMEA/CO$_2$; Flow rate: 70 mL/min; 254 nm; RT1: 5.5 min (5.5-1); RT2: 6.7 min (5.5-2)].

Example 5.6-1/5.6-2

1-(5-fluoro-1-(6-(4-(2-hydroxypropan-2-yl)-2-azabicyclo[2.1.1]hexan-2-yl)-2-methylpyrimidin-4-yl)-1H-indazol-6-yl)spiro[2.2]pentane-1-carbonitrile was purified via CHIRAL-Prep-SFC [Column: Lux-4, 21×250 mm; 20% Methanol with 0.25% DMEA/CO$_2$; Flow rate: 70 mL/min; 220 nm; RT1: 9.0 min (5.6-1); RT2: 9.6 min (5.6-2)].

Example 5.7-1/5.7-2

1-(5-fluoro-1-(6-(4-(2-hydroxypropan-2-yl)-2-azabicyclo[2.1.1]hexan-2-yl)-2-methylpyrimidin-4-yl)-1H-indazol-6-yl)spiro[2.2]pentane-1-carbonitrile was purified via CHIRAL-Prep-SFC [Column: IC, 21×250 mm; 45% Methanol with 0.25% DMEA/CO$_2$; Flow rate: 70 mL/min; 254 nm; RT1: 4.2 min (5.7-1); RT2: 5.4 min (5.7-2)].

Preparation of example 6.1, (R or S)-1-(1-(2-(4-(2-hydroxypropan-2-yl)-2-azabicyclo[2.1.1]hexan-2-yl)pyridin-4-yl)-1H-indazol-6-yl)spiro[2.2]pentane-1-carbonitrile Scheme 6

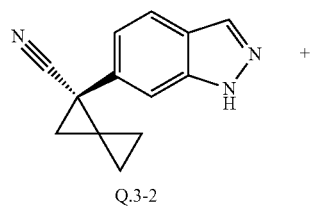

Q.3-2

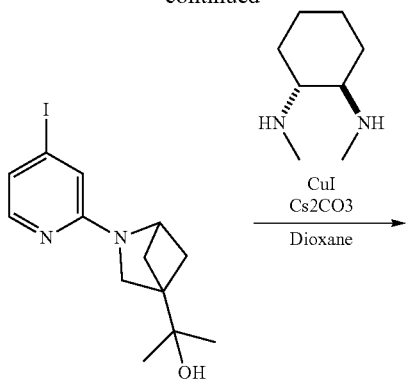

P.2

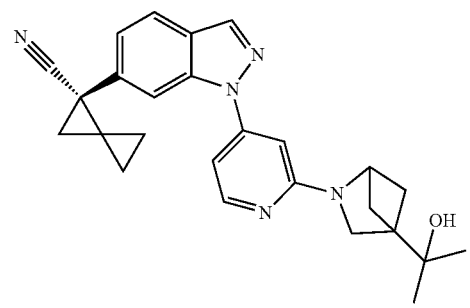

example 6.1-1

Enantiomerically pure 1-(1H-indazol-6-yl)spiro[2.2]pentane-1-carbonitrile (Q.3-2) (41.8 mg, 0.2 mmol), 2-(2-(4-iodopyridin-2-yl)-2-azabicyclo[2.1.1]hexan-4-yl)propan-2-ol (83 mg, 0.24 mmol), copper(I) iodide (7.62 mg, 0.04 mmol), cesium carbonate (195 mg, 0.600 mmol), and trans-N1,N2-dimethylcyclohexane-1,2-diamine (12.62 μl, 0.080 mmol) were added to a flask with septum and stir bar. The flask was sealed and its contents were placed under an inert atmosphere by evacuating and backfilling with nitrogen (3×). Dioxane (1.0 mL) was added through the septum and the resulting mixture was allowed to stir overnight at 90° C. The reaction mixture was filtered and purified by reverse phase prep-HPLC [method B] to provide (R or S)-1-(1-(2-(4-(2-hydroxypropan-2-yl)-2-azabicyclo[2.1.1]hexan-2-yl)pyridin-4-yl)-1H-indazol-6-yl)spiro[2.2]pentane-1-carbonitrile. MS (ESI) m/z calc'd for $C_{26}H_{28}N_5O$ [M+H]$^+$ 426 found 426]. $^1$H NMR (499 MHz, DMSO-d$_6$) δ 8.44 (s, 1H), 8.20 (d, J=5.4 Hz, 1H), 7.94 (d, J=8.4 Hz, 1H), 7.86 (s, 1H), 7.23 (d, J=8.3 Hz, 1H), 7.01 (d, J=4.8 Hz, 1H), 6.90 (s, 1H), 5.76 (s, 1H), 4.73 (s, 1H), 4.43 (s, 1H), 3.37 (s, 2H), 2.36 (d, J=5.0 Hz, 1H), 2.12 (d, J=5.0 Hz, 1H), 1.93-1.82 (m, 2H), 1.43-1.33 (m, 2H), 1.30-1.19 (m, 3H), 1.10-1.04 (m, 1H). LRRK2 IC$_{50}$ 1.2 nM.

The following examples in Table 10 were made according to General Scheme 2 and Scheme 6 above. Intermediates Q.3-1, Q.3-2 and racemic-R.3 were used. The building block used is indicated in the table. Purification was generally carried out by reverse phase prep-HPLC and when necessary further purification using prep-SFC. Where SFC was carried out to resolve isomers the conditions are reported following the table.

TABLE 10

Examples Prepared According to General Scheme 2 and Scheme 6

| Example | Structure<br>Name<br>Building Block X(Scheme X) | Observed m/z [M + H]+ | LRRK2 IC$_{50}$ (nM) |
|---|---|---|---|
| 6.1-2 | (R)-1-(1-(2-(4-(2-hydroxypropan-2-yl)-2-azabicyclo[2.1.1]hexan-2-yl)pyridin-4-yl)-1H-indazol-6-yl)spiro[2.2]pentane-1-carbonitrile.<br>Q.3-1(Scheme Q) | 426 | 5.3 |
| 6.2-1 | (R)-1-(1-(2-((R)-3-(2-hydroxypropan-2-yl)pyrrolidin-1-yl)pyridin-4-yl)-1H-indazol-6-yl)spiro[2.2]pentane-1-carbonitrile<br>Q.3-1(Scheme Q) | 414 | 1.8 |
| 6.2-2 | (S)-1-(1-(2-((R)-3-(2-hydroxypropan-2-yl)pyrrolidin-1-yl)pyridin-4-yl)-1H-indazol-6-yl)spiro[2.2]pentane-1-carbonitrile<br>Q.3-2(Scheme Q) | 414 | 0.9 |
| 6.3 | (S)-1-(1-(2-fluoro-6-(4-(2-hydroxypropan-2-yl)-2-azabicyclo[2.1.1]hexan-2-yl)pyridin-4-yl)-1H-indazol-6-yl)spiro[2.2]pentane-1-carbonitrile<br>Q.3-2(Scheme Q) | 444 | 15.0 |

TABLE 10-continued

Examples Prepared According to General Scheme 2 and Scheme 6

| Example | Structure<br>Name<br>Building Block X(Scheme X) | Observed m/z [M + H]⁺ | LRRK2 IC$_{50}$ (nM) |
|---|---|---|---|
| 6.4 | (S)-1-(1-(2-fluoro-6-((S)-3-methyl-4-(oxetan-3-yl)piperazin-1-yl)pyridin-4-yl)-1H-indazol-6-yl)spiro[2.2]pentane-1-carbonitrile<br>Q.3-2(Scheme Q) | 459 | 6.8 |
| 6.5 | (S)-1-(1-(2-((S)-3-methyl-4-(methylsulfonyl)piperazin-1-yl)pyridin-4-yl)-1H-indazol-6-yl)spiro[2.2]pentane-1-carbonitrile<br>Q.3-2(Scheme Q) | 463 | 1.5 |
| 6.6-1 | (R or S)-1-(1-(2-((R)-3-(2-hydroxypropan-2-yl)pyrrolidin-1-yl)pyridin-4-yl)-1H-pyrazolo[4,3-c]pyridin-6-yl)spiro[2.2]pentane-1-carbonitrile<br>Racemic-R.3(Scheme R) | 415 | 28.5 |
| 6.6-2 | (R or S)-1-(1-(2-((R)-3-(2-hydroxypropan-2-yl)pyrrolidin-1-yl)pyridin-4-yl)-1H-pyrazolo[4,3-c]pyridin-6-yl)spiro[2.2]pentane-1-carbonitrile<br>Racemic-R.3(Scheme R) | 415 | 3.4 |

TABLE 10-continued

Examples Prepared According to General Scheme 2 and Scheme 6

| Example | Structure Name Building Block X(Scheme X) | Observed m/z [M + H]+ | LRRK2 IC50 (nM) |
|---|---|---|---|
| 6.7-1 | (R or S)-1-(1-(2-(4-(2-hydroxypropan-2-yl)-2-azabicyclo[2.1.1]hexan-2-yl)pyridin-4-yl)-1H-pyrazolo[4,3-c]pyridin-6-yl)spiro[2.2]pentane-1-carbonitrile Racemic-R.3(Scheme R) | 427 | 59.0 |
| 6.7-2 | (R or S)-1-(1-(2-(4-(2-hydroxypropan-2-yl)-2-azabicyclo[2.1.1]hexan-2-yl)pyridin-4-yl)-1H-pyrazolo[4,3-c]pyridin-6-yl)spiro[2.2]pentane-1-carbonitrile Racemic-R.3(Scheme R) | 427 | 7.8 |

Example 6.6-1/6.6-2

1-(1-(2-((R)-3-(2-hydroxypropan-2-yl)pyrrolidin-1-yl)pyridin-4-yl)-1H-pyrazolo[4,3-c]pyridin-6-yl)spiro[2.2]pentane-1-carbonitrile was purified via CHIRAL-Prep-SFC [Column: AD-H, 21×250 mm; 40% Methanol with 0.25% DMEA/CO2; Flow rate: 70 mL/min; 254 nm; RT1: 3.1 min (6.6-1); RT2: 4.6 min (6.6-2)].

Example 6.7-1/6.7-2

1-(1-(2-(4-(2-hydroxypropan-2-yl)-2-azabicyclo[2.1.1]hexan-2-yl)pyridin-4-yl)-1H-pyrazolo[4,3-c]pyridin-6-yl)spiro[2.2]pentane-1-carbonitrile was purified via CHIRAL-Prep-SFC [Column: AD-H, 21×250 mm; 35% 2-Propanol with 0.25% DMEA/C02; Flow rate: 70 mL/min; 220 nm; RT1: 2.5 min (6.7-1); RT2: 3.7 min(6.7-2)].

Preparation of Example 7.3-1 and 7.3-2, (R or S)-1-(1-(2-(4-(2-hydroxypropan-2-yl)-2-azabicyclo[2.1.1]hexan-2-yl)-6-methylpyridin-4-yl)-1H-indazol-6-yl)spiro[2.2]pentane-1-carbonitrile Scheme 7

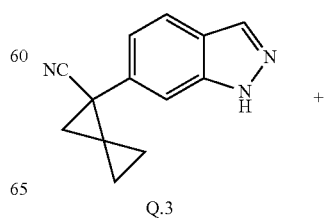

Q.3

-continued

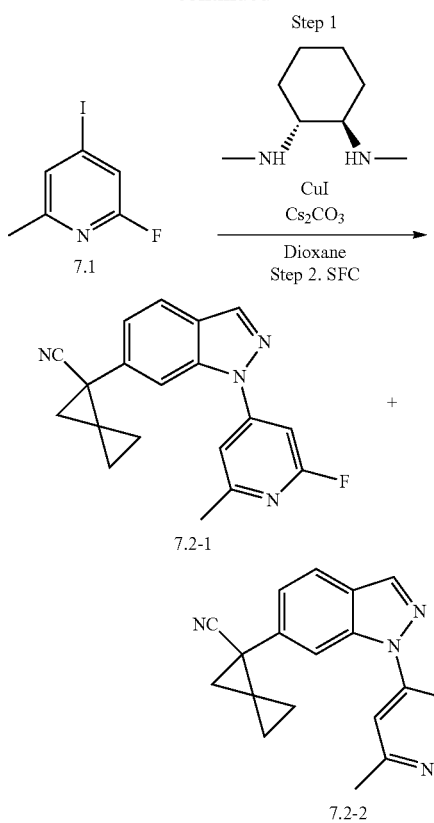

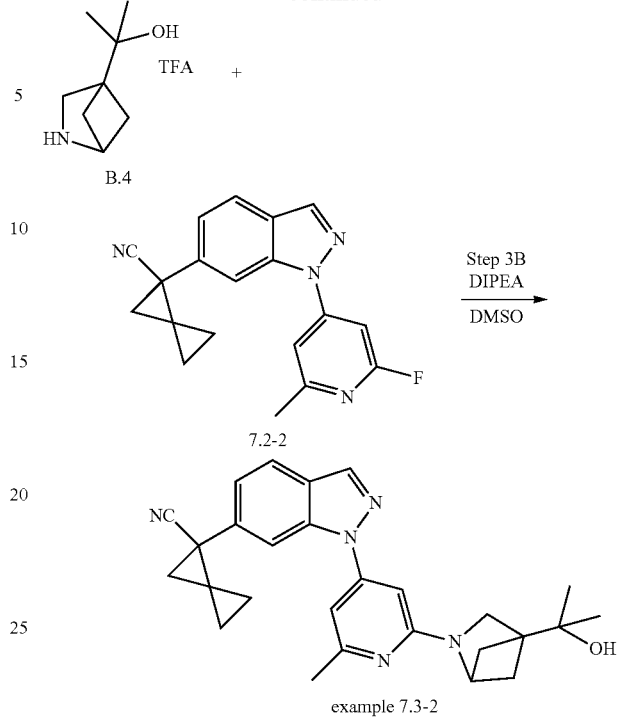

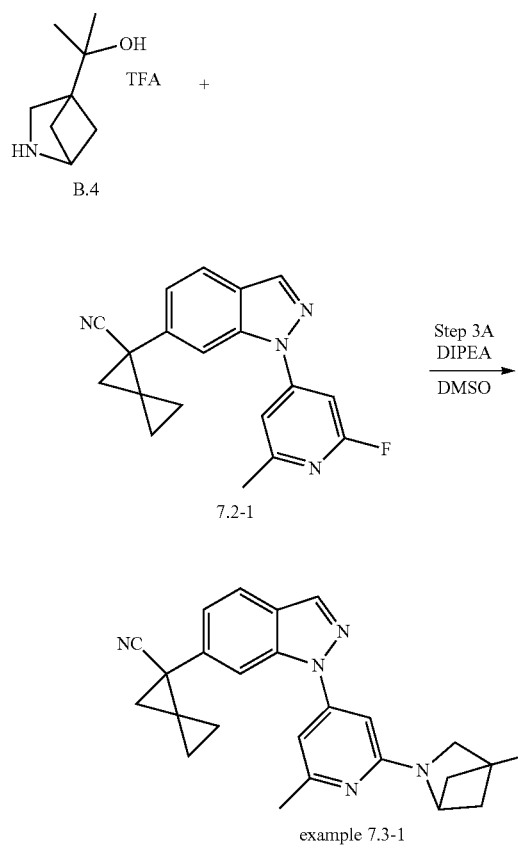

Step 1—Synthesis of Intermediate 7.2, (R or S)-1-(1-(2-fluoro-6-methylpyridin-4-yl)-1H-indazol-6-yl)spiro[2.2]pentane-1-carbonitrile To a mixture of racemic 1-(1H-indazol-6-yl)spiro[2.2]pentane-1-carbonitrile (300 mg, 1.43 mmol) (Q.3), 2-fluoro-4-iodo-6-methylpyridine (510 mg, 2.15 mmol), trans-N,N'-dimethyl-1,2-cyclohexanediamine (61.2 mg, 0.430 mmol), copper(I) iodide (82 mg, 0.43 mmol), and cesium carbonate (934 mg, 2.87 mmol) in a 20 mL microwave vial, was added DMSO (2 mL). The vial was sealed, degassed and backfilled with nitrogen (3×) and stirred at 50° C. overnight. The mixture was diluted with water (5 mL), and extracted with DCM (3×5 mL). The organic extracts were combined, dried over $MgSO_4$ and concentrated to dryness. The residue was purified by silica gel column chromatography (gradient elution: 0-50% EtOAc/hexanes).

Step 2—Resolution

The material from above was further purified by CHIRAL-Prep-SFC [Column: CHIRALPAK AS-H, 4.6×250 mm (5 μm); 25% (IPA/0.1% DIPA)/$CO_2$; Flow rate: 50 mL/min; 210 nm; Analytical Column: CHIRALPAK AS-H, 6×250 mm (5 μm); IPA/0.1% DIPA/$CO_2$; Flow rate: 3 mL/min; 254 nm RT1:2.28 min (7.2-1); RT2: 2.97 min (7.2-2)]. MS (ESI) m/z calc'd for $C_{19}H_{15}FN_4$ [M+H]$^+$ 319 found 319.

Step 3A—Synthesis of Example 7.3-1, (R or S)-1-(1-(2-(4-(2-hydroxypropan-2-yl)-2-azabicyclo[2.1.1]hexan-2-yl)-6-methylpyridin-4-yl)-1H-indazol-6-yl)spiro[2.2]pentane-1-carbonitrile, TFA Salt To a solution of (R or S)-1-(1-(2-fluoro-6-methylpyridin-4-yl)-1H-indazol-6-yl)spiro[2.2]pentane-1-carbonitrile (7.2-

1) (50 mg, 0.16 mmol) and 2-(2-azabicyclo[2.1.1]hexan-4-yl)propan-2-ol (44.4 mg, 0.314 mmol) (B.4) in DMSO (1 mL) was added DIEA (0.055 ml, 0.31 mmol). The vial was sealed and heated at 80° C. for 2 h and then at 100° C. overnight. The temperature was increased to 120° C., and stirring was continued for 8 h. The mixture was cooled, filtered, and the filtrate was purified by reverse phase prep-HPLC (Method A) to provide (R or S)-1-(1-(2-(4-(2-hydroxypropan-2-yl)-2-azabicyclo[2.1.1]hexan-2-yl)-6-methylpyridin-4-yl)-1H-indazol-6-yl)spiro[2.2]pentane-1-carbonitrile, TFA salt. MS (ESI) m/z calc'd for $C_{27}H_{30}N_5O$ [M+H]$^+$ 440 found 440. $^1$H NMR (499 MHz, CDCl$_3$) δ 8.30 (s, 1H), 8.22 (s, 1H), 7.92 (d, J=8.3 1H), 7.20 (s, 1H), 7.11 (m, 2H), 3.80 (m, 3H), 2.63 (s, 3H), 2.57 (d, J=5.0 Hz, 1H), 1.78 (d, J=5.0 Hz, 1H), 1.60-1.85 (m, 4H), 1.43-1.25 (m, 2H), 1.23-1.33 (s, 6H), 1.05 (m, 2H).
LRRK2 IC50 nM 54.2 nM Step 3B—Synthesis of Example 7.3-2, (R or S)-1-(1-(2-(4-(2-hydroxypropan-2-yl)-2-azabicyclo[2.1.1] hexan-2-yl)-6-methylpyridin-4-yl)-1H-indazol-6-yl) spiro[2.2]pentane-1-carbonitrile, TFA Salt To a solution of (R or S)-1-(1-(2-fluoro-6-methylpyridin-4-yl)-1H-indazol-6-yl)spiro[2.2]pentane-1-carbonitrile (7.2-2) (50 mg, 0.16 mmol) and 2-(2-azabicyclo[2.1.1]hexan-4-yl)propan-2-ol (44.4 mg, 0.314 mmol) (B.4) in DMSO (1 mL) was added DIEA (0.055 ml, 0.31 mmol). The vial was sealed and heated at 80° C. for 2 h and then at 100° C. overnight. The temperature was increased to 120° C., and stirring was continued for 8 h. The mixture was cooled, filtered, and the filtrate was purified by reverse phase prep-HPLC (Method A) to provide (R or S)-1-(1-(2-(4-(2-hydroxypropan-2-yl)-2-azabicyclo[2.1.1]hexan-2-yl)-6-methylpyridin-4-yl)-1H-indazol-6-yl)spiro[2.2]pentane-1-carbonitrile, TFA salt. MS (ESI) m/z calc'd for $C_{27}H_{30}N_5O$ [M+H]$^+$ 440 found 440. $^1$H NMR (499 MHz, CDCl$_3$) δ 8.30 (s, 1H), 8.22 (s, 1H), 7.92 (d, J=8.3 1H), 7.20 (s, 1H), 7.11 (m, 2H), 3.80 (m, 3H), 2.63 (s, 3H), 2.57 (d, J=5.0 Hz, 1H), 1.78 (d, J=5.0 Hz, 1H), 1.60-1.85 (m, 4H), 1.43-1.25 (m, 2H), 1.23-1.33 (s, 6H), 1.05 (m, 2H).
LRRK2 IC50 4.6 nM Preparation of Example 8.5, (S)-1-(1-(2-(azetidin-1-yl)-6-(4-(2-hydroxypropan-2-yl)-2-azabicyclo[2.1.1] hexan-2-yl)pyrimidin-4-yl)-1H-indazol-6-yl)spiro [2.2]pentane-1-carbonitrile Scheme 8

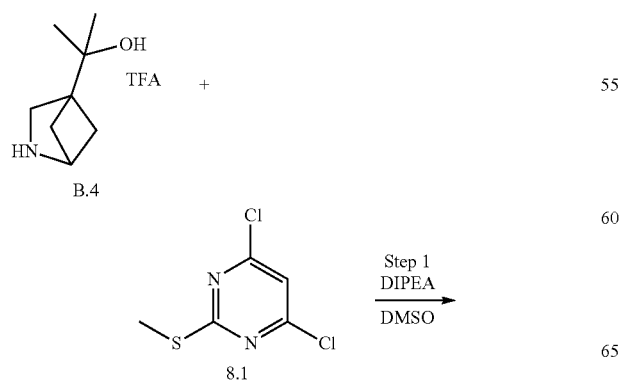

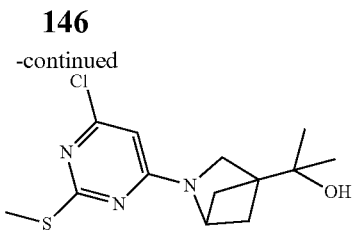

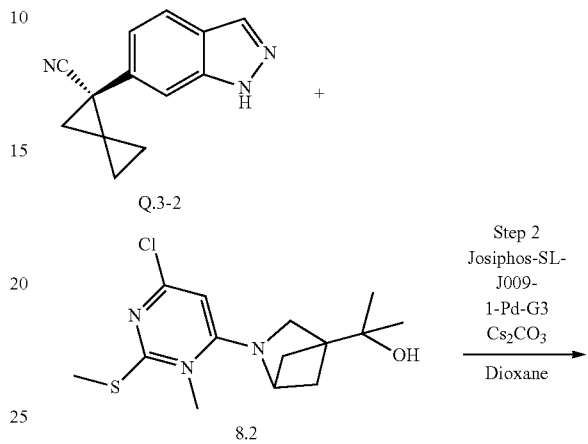

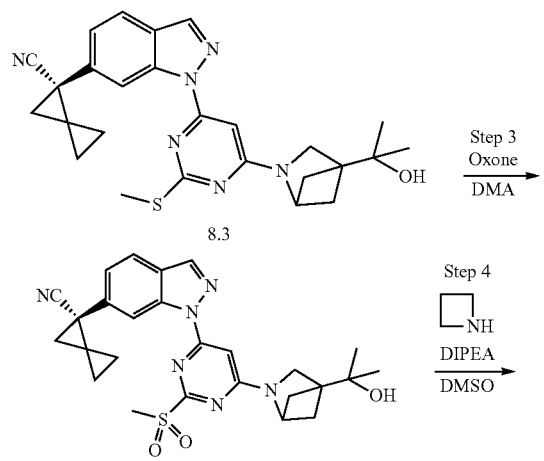

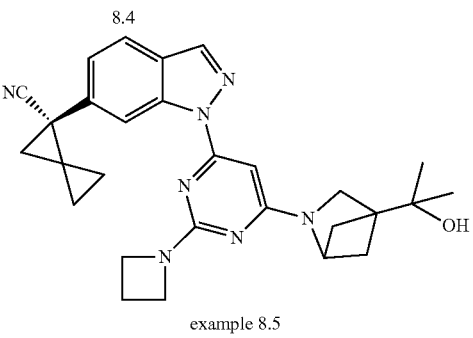

example 8.5

Step 1—Synthesis of Intermediate 8.2, 2-(2-(6-chloro-2-(methylthio)pyrimidin-4-yl)-2-azabicyclo [2.1.1]hexan-4-yl)propan-2-ol To a suspension of 4,6-dichloro-2-(methylthio)pyrimidine (382 mg, 1.96 mmol) and 2-(2-azabicyclo[2.1.1]hexan-4-yl)propan-2-ol, TFA salt (B.4) (500 mg, 1.96 mmol) in DMSO (2 mL) was added DIPEA (1.37 ml, 7.84 mmol). The mixture was stirred at 80° C. overnight. The mixture was diluted with saturated aqueous ammonium chloride (5 mL) and extracted with DCM (3×5 mL). The extracts were combined, dried over MgSO₄, filtered and concentrated. The residue was purified by silica gel column chromatography (gradient elution: 0-100% EtOAc/hexanes) to provide 2-(2-(6-chloro-2-(methylthio)pyrimidin-4-yl)-2-azabicyclo[2.1.1]hexan-4-yl)propan-2-ol.

Step 2—Synthesis of Intermediate 8.3, (S)-1-(1-(6-(4-(2-hydroxypropan-2-yl)-2-azabicyclo[2.1.1]hexan-2-yl)-2-(methylthio)pyrimidin-4-yl)-1H-indazol-6-yl)spiro[2.2]pentane-1-carbonitrile 2-(2-(6-chloro-2-(methylthio)pyrimidin-4-yl)-2-azabicyclo[2.1.1]hexan-4-yl)propan-2-ol (287 mg, 0.956 mmol), enantiomerically pure (S)-1-(1H-indazol-6-yl)spiro[2.2]pentane-1-carbonitrile (200 mg, 0.956 mmol) (Q.3-2), Cs₂CO₃ (934 mg, 2.87 mmol) and Josiphos-SL-J009-1-Pd-G3 (88 mg, 0.096 mmol) were charged in a vessel, the vessel was evacuated and backfilled nitrogen (3×). Dioxane (5 mL) was added, the reaction was degassed again (3×) and stirred at 65° C. overnight. The reaction mixture was cooled to room temperature, diluted with saturated aqueous ammonium chloride (5 mL) and extracted with ethyl acetate (3×5 mL). The organic layer was washed with water (2×10 mL), dried over sodium sulfate, filtered and concentrated. The crude residue was purified silica gel column chromatography (gradient elution: 0-100% EtOAc/hexanes) to provide (R or S)-1-(1-(6-(4-(2-hydroxypropan-2-yl)-2-azabicyclo[2.1.1]hexan-2-yl)-2-(methylthio)pyrimidin-4-yl)-1H-indazol-6-yl)spiro[2.2]pentane-1-carbonitrile.

Step 3—Synthesis of Intermediate 8.4, (S)-1-(1-(6-(4-(2-hydroxypropan-2-yl)-2-azabicyclo[2.1.1]hexan-2-yl)-2-(methylsulfonyl)pyrimidin-4-yl)-1H-indazol-6-yl)spiro[2.2]pentane-1-carbonitrile (S)-1-(1-(6-(4-(2-hydroxypropan-2-yl)-2-azabicyclo[2.1.1]hexan-2-yl)-2-(methylthio)pyrimidin-4-yl)-1H-indazol-6-yl)spiro[2.2]pentane-1-carbonitrile (400 mg, 0.846 mmol) was suspended in DMA (3 mL). Oxone (1.67 g, 2.71 mmol) was added, followed by water (1.0 mL). The mixture was stirred at room temperature overnight. The reaction was quenched with saturated aqueous ammonium chloride (10 mL) and the resulting suspension was stirred at room temperature for 2 h, and then filtered. The material was used for next step without further purification.

Step 4—Synthesis of Example 8.5, (S)-1-(1-(2-(azetidin-1-yl)-6-(4-(2-hydroxypropan-2-yl)-2-azabicyclo[2.1.1]hexan-2-yl)pyrimidin-4-yl)-1H-indazol-6-yl)spiro[2.2]pentane-1-carbonitrile (S)-1-(1-(6-(4-(2-hydroxypropan-2-yl)-2-azabicyclo[2.1.1]hexan-2-yl)-2-(methylsulfonyl)pyrimidin-4-yl)-1H-indazol-6-yl)spiro[2.2]pentane-1-carbonitrile (80 mg, 0.16 mmol), azetidine hydrochloride (119 mg, 1.27 mmol) and cesium carbonate (517 mg, 1.59 mmol), were charged in a vial, and DMSO (1 mL) was added. The vial was sealed and stirred at 80° C. for 4 h. The mixture was filtered and purified by reverse phase prep-HPLC (Method A) to provide (S)-1-(1-(2-(azetidin-1-yl)-6-(4-(2-hydroxypropan-2-yl)-2-azabicyclo[2.1.1]hexan-2-yl)pyrimidin-4-yl)-1H-indazol-6-yl)spiro[2.2]pentane-1-carbonitrile. MS (ESI) m/z calc'd for $C_{28}H_{32}N_7O$ [M+H]⁺ 482 found 482. ¹H NMR (499 MHz, CD₃OD) δ 8.86 (s, 1H), 8.30 (s, 1H), 7.81 (d, J=8.3 1H), 7.18 (d, J=8.3, 1H), 4.47 (m, 4H), 3.63 (m, 2H), 2.53 (m, 3H), 2.14 (m, 4H), 1.60-1.85 (m, 4H), 1.43-1.25 (m, 2H), 1.23-1.33 (s, 6H), 1.05 (m, 2H). LRRK2 IC₅₀ 9.8 nM Preparation of Example 9.4, 1-(1-(2-((3S,4s,5R)-4-hydroxy-3,4,5-trimethylpiperidin-1-yl)pyridin-4-yl)-1H-indazol-6-yl)spiro[2.2]pentane-1-carbonitrile, TFA Salt

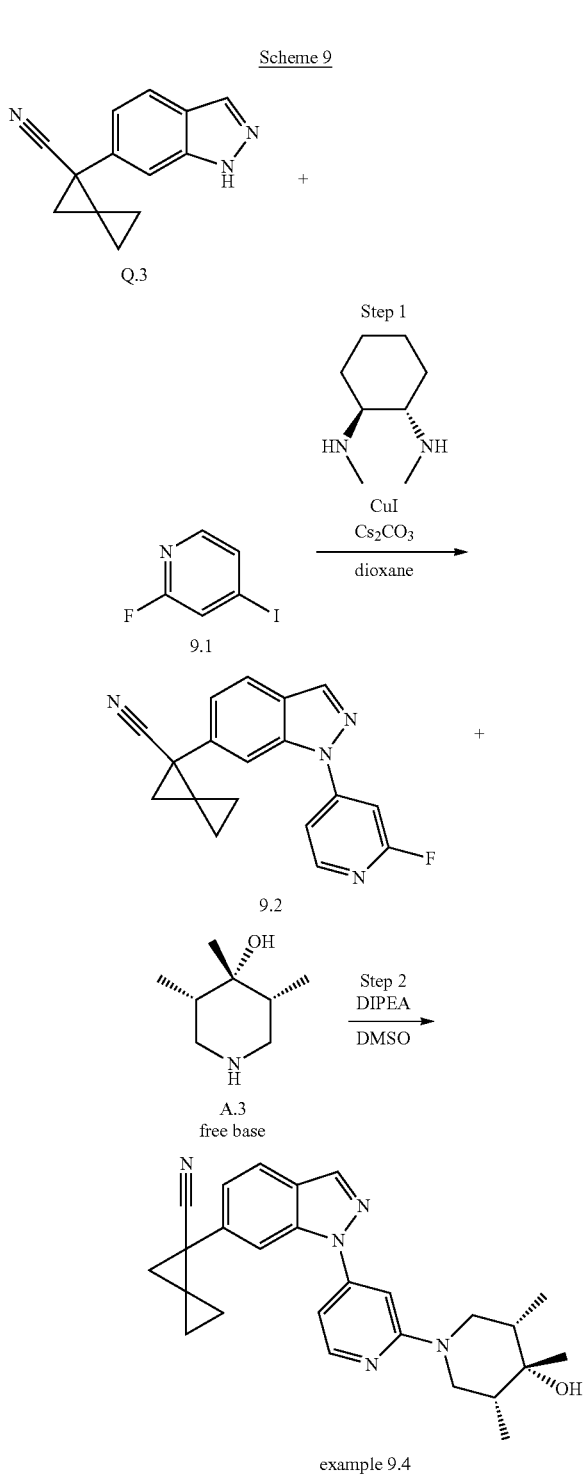

Scheme 9 example 9.4

Step 1—Synthesis of Intermediate 9.2, 1-(1-(2-fluoropyridin-4-yl)-1H-indazol-6-yl)spiro[2.2]pentane-1-carbonitrile To a solution of 1-(1H-indazol-6-yl)spiro[2.2]pentane-1-carbonitrile (50 mg, 0.239 mmol) (Q.3) in anhydrous toluene (4 mL) was added 2-fluoro-4-iodopyridine (80 mg, 0.36 mmol), trans-N1,N2-dimethylcyclohexane-1,2-diamine (6.8 mg, 0.048 mmol), $Cs_2CO_3$ (234 mg, 0.717 mmol) and copper(I) iodide (4.55 mg, 0.024 mmol), and the resulting mixture was stirred at 90° C. under $N_{2(g)}$ for 16 h. The reaction was filtered and concentration and the residue was purified by silica gel prep-TLC (EtOAc/Hexanes) to provide 1-(1-(2-fluoropyridin-4-yl)-1H-indazol-6-yl)spiro[2.2]pentane-1-carbonitrile.

Step 2—Synthesis of Example 9.4, 1-(1-(2-((3S,4s,5R)-4-hydroxy-3,4,5-trimethylpiperidin-1-yl)pyridin-4-yl)-1H-indazol-6-yl)spiro[2.2]pentane-1-carbonitrile, TFA Salt To a solution of 1-(1-(2-fluoropyridin-4-yl)-1H-indazol-6-yl)spiro[2.2]pentane-1-carbonitrile (17 mg, 0.056 mmol) in anhydrous DMSO (2 mL) was added (3R,4S,5S)-3,4,5-trimethylpiperidin-4-ol (16.0 mg, 0.112 mmol) and DIPEA (0.1 mL, 0.573 mmol), and the resulting mixture was stirred at 100° C. for 8 h. The reaction was concentrated and the residue was purified by pre-HPLC (Column: YMC-Actus Pro C18, 30×150 mm; 30-50% MeCN/water with 0.1% TFA; Flow rate: 40 mL/min) to provide 1-(1-(2-((3R,4S,5S)-4-hydroxy-3,4,5-trimethylpiperidin-1-yl)pyridin-4-yl)-1H-indazol-6-yl)spiro[2.2]pentane-1-carbonitrile. MS (ESI) m/z calc'd for $C_{26}H_{30}N_5O$ [M+H]$^+$ 428 found 428. $^1$H NMR (400 MHz, $CD_3OD$) δ 8.46 (s, 1H), 8.05-8.11 (m, 2H), 7.96 (d, J=8.14 Hz, 1H), 7.60 (d, J=1.87 Hz, 1H), 7.52 (dd, J=1.87, 6.93 Hz, 1H), 7.29 (dd, J=1.32, 8.47 Hz, 1H), 3.87 (m, J=4.18, 13.09 Hz, 2H), 3.23-3.29 (m, 2H), 2.38 (d, J=5.17 Hz, 1H), 2.11 (d, J=5.17 Hz, 1H), 1.79-1.88 (m, 2H), 1.29-1.33 (m, 3H), 1.27 (s, 3H), 1.09 (d, J=6.71 Hz, 7H). LRRK2 $IC_{50}$ 14.2 nM Preparation of Examples 10.3-1 and 10.3-2, (R or S)-1-(1-(6-(4-(2-hydroxypropan-2-yl)-2-azabicyclo[2.1.1]hexan-2-yl)pyridazin-4-yl)-1H-indazol-6-yl)spiro[2.2]pentane-1-carbonitrile Scheme 10

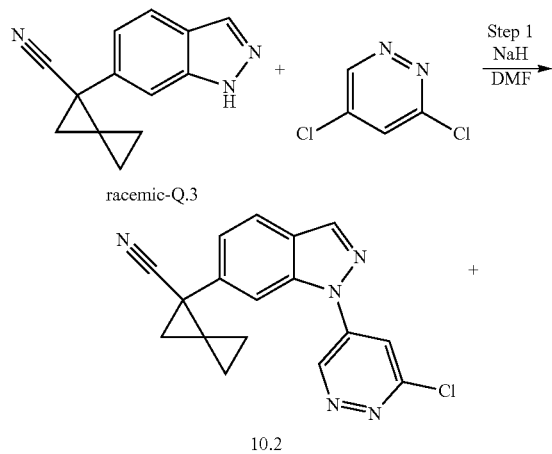

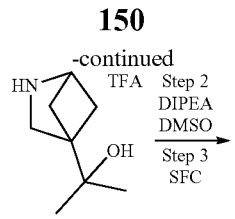

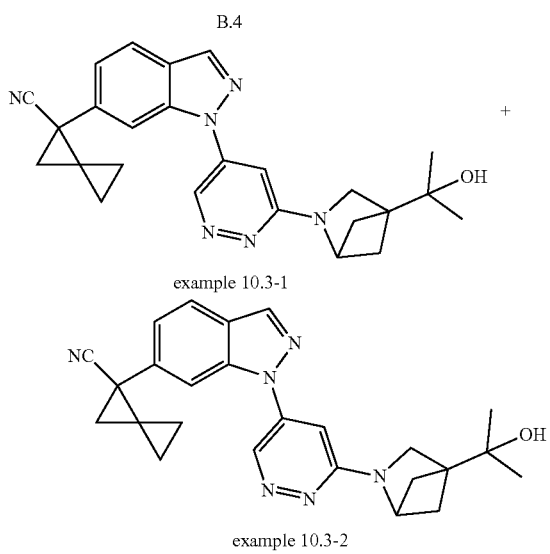

example 10.3-1 example 10.3-2

Step 1—Synthesis of Intermediate 10.2, 1-(1-(6-chloropyridazin-4-yl)-1H-indazol-6-yl)spiro[2.2]pentane-1-carbonitrile To a solution of racemic 1-(1H-indazol-6-yl)spiro[2.2]pentane-1-carbonitrile (150 mg, 0.717 mmol) (Q.3) in anhydrous DMF (4 mL) was added NaH (43.0 mg, 1.08 mmol) at 0° C., and the reaction was stirred for 20 min. Then 3,5-dichloropyridazine (128 mg, 0.860 mmol) was added to the mixture. The resulting mixture was stirred at 0° C. for 1 hour. The reaction mixture was poured into water (10 mL) and extracted with EtOAc (3×30 mL). The organic layer was washed with water (10 mL), dried over $Na_2SO_4$ filtered and concentrated. The residue was purified via silica gel chromatography (gradient elution: 0-22% EtOAc/Hexanes) to provide 1-(1-(6-chloropyridazin-4-yl)-1H-indazol-6-yl)spiro[2.2]pentane-1-carbonitrile.

Step 2—Synthesis of Example 10.3-1 and 10.3-2, (R or S)-1-(1-(6-(4-(2-hydroxypropan-2-yl)-2-azabicyclo[2.1.1]hexan-2-yl)pyridazin-4-yl)-1H-indazol-6-yl)spiro[2.2]pentane-1-carbonitrile To a solution of 1-(1-(6-chloropyridazin-4-yl)-1H-indazol-6-yl)spiro[2.2]pentane-1-carbonitrile (30 mg, 0.093 mmol) in anhydrous DMSO (2 mL) was added DIPEA (0.1 mL, 0.6 mmol) and 2-(2-azabicyclo[2.1.1]hexan-4-yl)propan-2-ol, TFA salt (19.75 mg, 0.140 mmol) (B.4). The resulting mixture was stirred at 80° C. for 5 h. LCMS showed the reaction was complete. The reaction mixture was poured into water (10 mL) and extracted with EtOAc (3×20 mL). The organic layer was washed with water (10 mL), dried over $Na_2SO_4$, filtered and concentrated. The residue was purified by reverse phase prep-HPLC (Column: YMC-Actus Pro C18, 30×150 mm; 20-50% MeCN/water with 0.1% TFA; Flow rate: 40 mL/min) to provide 1-(1-(6-(4-(2- hydroxypropan-2-yl)-2-azabicyclo[2.1.1]hexan-2-yl)pyridazin-4-yl)-1H-indazol-6-yl)spiro[2.2]pentane-1-carbonitrile, TFA salt.

Step 3-Resolution

Racemic (R)-1-(1H-indazol-6-yl)spiro[2.2]pentane-1-carbonitrile was resolved by the SFC [Column: CHIRALPAK AS, 3×25 cm (5 µm); 40% IPA/CO$_2$; Flow rate: 60 mL/min; 220 nm; RT1:5.29 min (10.3-1); RT2: 5.70 min (10.3-2)] to afford two peaks.

Example 10.3-1, (R or S)-1-(1-(6-(4-(2-hydroxypropan-2-yl)-2-azabicyclo[2.1.1]hexan-2-yl)pyridazin-4-yl)-1H-indazol-6-yl)spiro[2.2]pentane-1-carbonitrile MS (ESI) m/z calc'd for C$_{25}$H$_{27}$N$_6$O [M+H]$^+$ 427 found 427. $^1$H NMR (400 MHz, CD$_3$OD) δ 9.02 (s, 1H), 8.35 (s, 1H), 7.98 (s, 1H), 7.89 (d, J=8.77 Hz, 1H), 7.21-7.30 (m, 2H), 3.56 (s, 2H), 2.33 (d, J=5.26 Hz, 1H), 2.04-2.10 (m, 3H), 1.58 (m, 2H), 1.28-1.34 (m, 10H), 1.09-1.14 (m, 1H). LRRK2 IC$_{50}$ 35.2 nM.

Example 10.3-2, (R or S)-1-(1-(6-(4-(2-hydroxypropan-2-yl)-2-azabicyclo[2.1.1]hexan-2-yl)pyridazin-4-yl)-1H-indazol-6-yl)spiro[2.2]pentane-1-carbonitrile MS (ESI) m/z calc'd for C$_{25}$H$_{27}$N$_6$O [M+H]$^+$ 427 found 427. $^1$H NMR (400 MHz, METHANOL-d$_4$) δ 9.01 (d, J=1.75 Hz, 1H), 8.34 (s, 1H), 7.98 (s, 1H), 7.89 (d, J=8.3 Hz, 1H), 7.20-7.30 (m, 2H), 3.56 (s, 2H), 2.33 (d, J=5.3 Hz, 1H), 2.04-2.08 (m, 3H), 1.58 (m, 2H), 1.28-1.32 (m, 10H), 1.07-1.14 (m, 1H). LRRK2 IC$_{50}$ 15.4 nM.

TABLE 11

Compounds Prepared According to Scheme 10

| Example | Structure Name | Observed m/z [M + H]$^+$ | LRRK2 IC$_{50}$ (nM) |
|---|---|---|---|
| 10.4-1 | 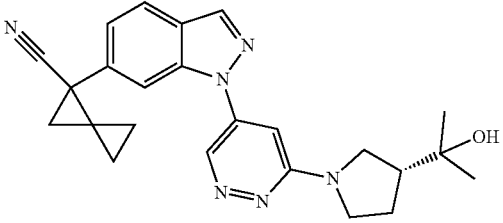<br>(R or S)-1-(1-(6-((R)-3-(2-hydroxypropan-2-yl)pyrrolidin-1-yl)pyridazin-4-yl)-1H-indazol-6-yl)spiro[2.2]pentane-1-carbonitrile | 415 | 18.7 |
| 10.4-2 | 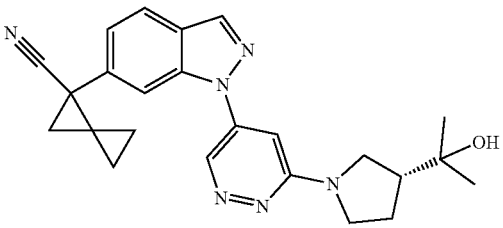<br>(R or S)-1-(1-(6-((R)-3-(2-hydroxypropan-2-yl)pyrrolidin-1-yl)pyridazin-4-yl)-1H-indazol-6-yl)spiro[2.2]pentane-1-carbonitrile | 415 | 2.7 |

Example 10.4-1/10.4-2

1-(1-(6-((R)-3-(2-hydroxypropan-2-yl)pyrrolidin-1-yl)pyridazin-4-yl)-1H-indazol-6-yl)spiro[2.2]pentane-1-carbonitrile was separated by CHIRAL-Prep-SFC [Column: CHIRALPAK AS, 3×25 cm (5 µm); 40% IPA/CO$_2$; Flow rate: 50 mL/min; 220 nm; RT1: 5.3 min (10.4-1); peak 2: 5.6 min (10.4-2)].

Preparation of Example 11.1, (S)-1-(1-(2-methyl-6-(4-(3-methyloxetan-3-yl)piperazin-1-yl)pyrimidin-4-yl)-1H-indazol-6-yl)spiro[2.2]pentane-1-carbonitrile Scheme 11

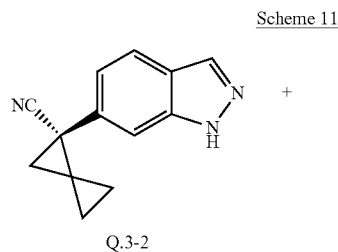

Q.3-2

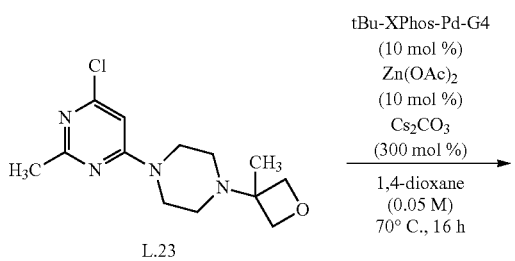

L.23

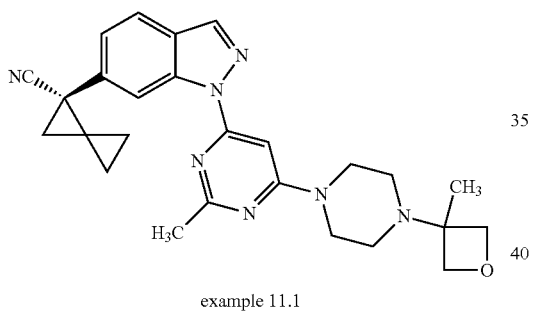

example 11.1

A 20 mL vial was charged with (S)-1-(1H-indazol-6-yl)spiro[2.2]pentane-1-carbonitrile (67 mg, 0.318 mmol), 4-chloro-2-methyl-6-(4-(3-methyloxetan-3-yl)piperazin-1-yl)pyrimidine (90 mg, 0.318 mmol), cesium carbonate (311 mg, 0.955 mmol), diacetoxyzinc (6 mg, 0.032 mmol), $^t$Bu-Xphos-Pd-G4 (26 mg, 0.032 mmol), and a magnetic stirrer. The vial was sealed with a rubber septum, then evacuated and purged with inert atmosphere on the manifold (3×). 1,4-Dioxane (5 mL) was added. The reaction mixture was heated to 70° C. and maintained at this temperature under a positive pressure of $N_2$. At 16 hours the vial was removed from the heat. Upon cooling to room temperature, the mixture was diluted with EtOAc, filtered over a pad of Celite®, and concentrated to dryness in vacuo. The crude residue was submitted for purification by preparative reverse phase HPLC (Method B). This provided (S)-1-(1-(2-methyl-6-(4-(3-methyloxetan-3-yl)piperazin-1-yl)pyrimidin-4-yl)-1H-indazol-6-yl)spiro[2.2]pentane-1-carbonitrile (80 mg, 55% yield). MS (ESI) m/z calc'd for $C_{26}H_{30}N_7O$ $[M+H]^+$ 456, found 456; $^1$H NMR (500 MHz, DMSO-$d_6$) δ 9.03 (s, 1H), 8.43 (s, 1H), 7.88 (d, J=8.4 Hz, 1H), 7.17 (dd, J=8.4, 1.5 Hz, 1H), 6.98 (s, 1H), 4.45 (d, J=5.5 Hz, 2H), 4.15 (d, J=5.5 Hz, 2H), 3.69 (s, 4H), 2.38 (m, 5H), 1.98 (d, J=5.1 Hz, 1H), 1.30 (m, 1H), 1.25 (m, overlap, 5H), 1.04 (m, 1H).

LRRK2 $IC_{50}$ 0.6 nM.

The following examples in Table 12 were made according to General scheme 2 and Scheme 11 above. Unless stated otherwise intermediate Q.3-2 was used and combined with the appropriate pyrimidine. The compounds were generally purified by silica gel chromatography, reverse phase prep-HPLC and SFC. Where isomers were separated by SFC, conditions are provided after the table.

TABLE 12

| | Compounds Prepared According to Scheme 11 | | |
|---|---|---|---|
| Example | Structure Name | Observed m/z [M + H]$^+$ | LRRK2 IC$_{50}$ (nM) |
| 11.2 | 1-(S)-(1-(2-methyl-6-((4aR,7aS or 4aS,7aR)-4-methylhexahydropyrrolo[3,4-b][1,4]oxazin-6(2H)-yl)pyrimidin-4-yl)-1H-indazol-6-yl)spiro[2.2]pentane-1-carbonitrile, TFA | 441 | 0.6 |

TABLE 12-continued

Compounds Prepared According to Scheme 11

| Example | Structure Name | Observed m/z [M + H]+ | LRRK2 IC50 (nM) |
|---|---|---|---|
| 11.3 | 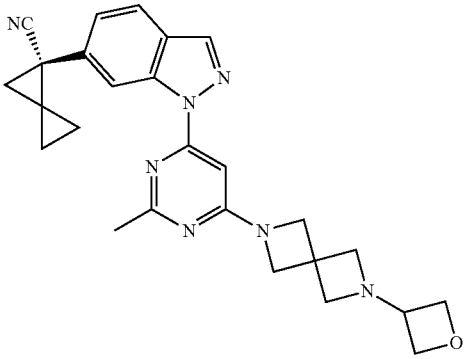<br>1-(S)-(1-(2-methyl-6-(6-(oxetan-3-yl)-2,6-diazaspiro[3.3]heptan-2-yl)pyrimidin-4-yl)-1H-indazol-6-yl)spiro[2.2]pentane-1-carbonitrile | 454 | 454 |
| 11.4 | 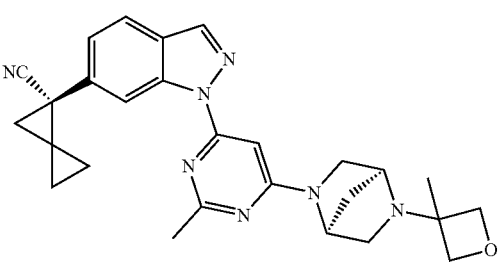<br>1-(S)-(1-(2-methyl-6-((1S,4S)-5-(3-methyloxetan-3-yl)-2,5-diazabicyclo[2.2.1]heptan-2-yl)pyrimidin-4-yl)-1H-indazol-6-yl)spiro[2.2]pentane-1-carbonitrile, TFA | 468 | 8.6 |
| 11.5 | 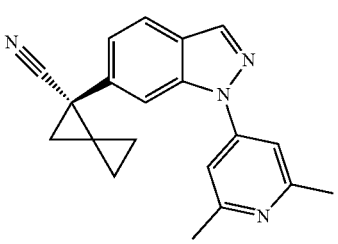<br>(S)-1-(1-(2,6-dimethylpyridin-4-yl)-1H-indazol-6-yl)spiro[2.2]pentane-1-carbonitrile | 315 | 7.8 |
| 11.6 | 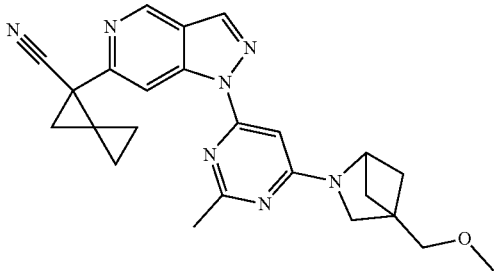<br>(R or S)-1-(1-(6-(4-(methoxymethyl)-2-azabicyclo[2.1.1]hexan-2-yl)-2-methylpyrimidin-4-yl)-1H-pyrazolo[4,3-c]pyridin-6-yl)spiro[2.2]pentane-1-carbonitrile<br>R.3-1 (Scheme R) + Z.6 (Scheme Z) | 427 | 1.0 |

TABLE 12-continued

Compounds Prepared According to Scheme 11

| Example | Structure Name | Observed m/z [M + H]⁺ | LRRK2 IC$_{50}$ (nM) |
|---|---|---|---|
| 11.7 | 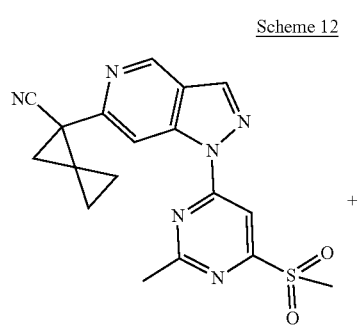

(S)-1-(1-(6-methylpyrimidin-4-yl)-1H-indazol-6-yl)spiro[2.2]pentane-1-carbonitrile | 302 | 7.4 |

Preparation of Example 12.1, (S or R)-1-(1-(2-methyl-6-(6-(2,2,2-trifluoroethyl)-2,6-diazaspiro[3.3]heptan-2-yl)pyrimidin-4-yl)-1H-pyrazolo[4,3-c]pyridin-6-yl)spiro[2.2]pentane-1-carbonitrile Scheme 12

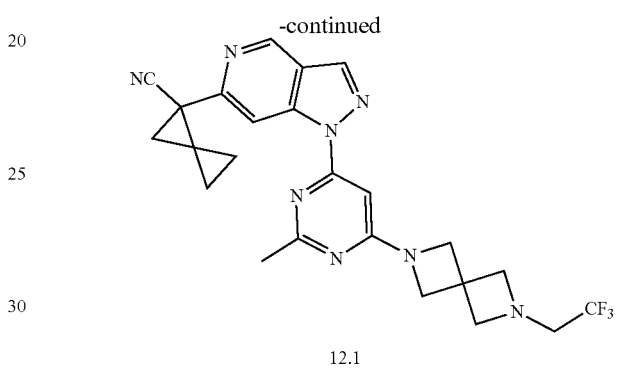

12.1

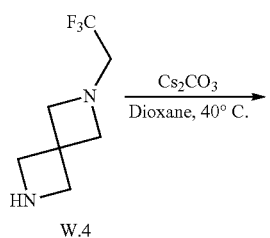

A solution of (S or R)-1-(1-(2-methyl-6-(methylsulfonyl)pyrimidin-4-yl)-1H-pyrazolo[4,3-c]pyridin-6-yl)spiro[2.2]pentane-1-carbonitrile (V.4-1) (380 mg, 1 mmol) in Dioxane (5000 µl) was added to a vial containing cesium carbonate (977 mg, 3.00 mmol) and 2-(2,2,2-trifluoroethyl)-2,6-diazaspiro[3.3]heptane (W.4) (360 mg, 2.000 mmol). The resulting mixture was allowed to stir overnight at 40° C. The residue was purified by column chromatography on silica (0-100% 3:1 Ethyl Acetate:Ethanol/Hexane). The desired fractions were pooled and concentrated under reduced pressure to afford (S or R)-1-(1-(2-methyl-6-(6-(2,2,2-trifluoroethyl)-2,6-diazaspiro[3.3]heptan-2-yl)pyrimidin-4-yl)-1H-pyrazolo[4,3-c]pyridin-6-yl)spiro[2.2]pentane-1-carbonitrile. MS (ESI) m/z calc'd for C$_{24}$H$_{23}$F$_3$N$_8$ [M+H]⁺ 481 found 481. ¹H NMR (499 MHz, DMSO-d6) δ 9.15 (s, 1H), 8.81 (s, 1H), 8.65 (s, 1H), 6.56 (s, 1H), 4.20 (s, 4H), 3.56 (s, 4H), 3.20 (q, J=10.2 Hz, 2H), 2.49 (s, 3H), 2.37 (d, J=4.4 Hz, 1H), 2.27 (d, J=4.4 Hz, 1H), 1.29-1.19 (m, 3H), 1.03-0.98 (m, 1H). LRRK2 IC$_{50}$ 2.1 nM

TABLE 13

Compounds Prepared According to Scheme 12

| Example | Structure Name Building Block X(Scheme X) | Observed m/z [M + H]+ | LRRK2 IC$_{50}$ (nM) |
|---|---|---|---|
| 12.2 | 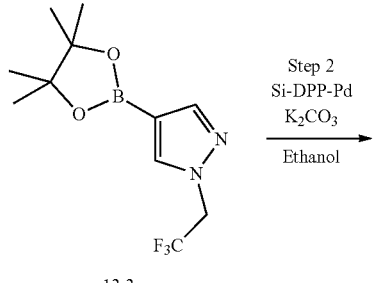<br>(R or S)-1-(1-(2-methyl-6-(6-(2,2,2-trifluoroethyl)-2,6-diazaspiro[3.3]heptan-2-yl)pyrimidin-4-yl)-1H-indazol-6-yl)spiro[2.2]pentane-1-carbonitrile<br>V.4-2(Scheme V) | 480 | 28.4 |

Preparation of Example 13.4, 1-(S)-(1-(2-(1-(2,2,2-trifluoroethyl)-1H-pyrazol-4-yl)pyridin-4-yl)-1H-indazol-6-yl)spiro[2.2]pentane-1-carbonitrile

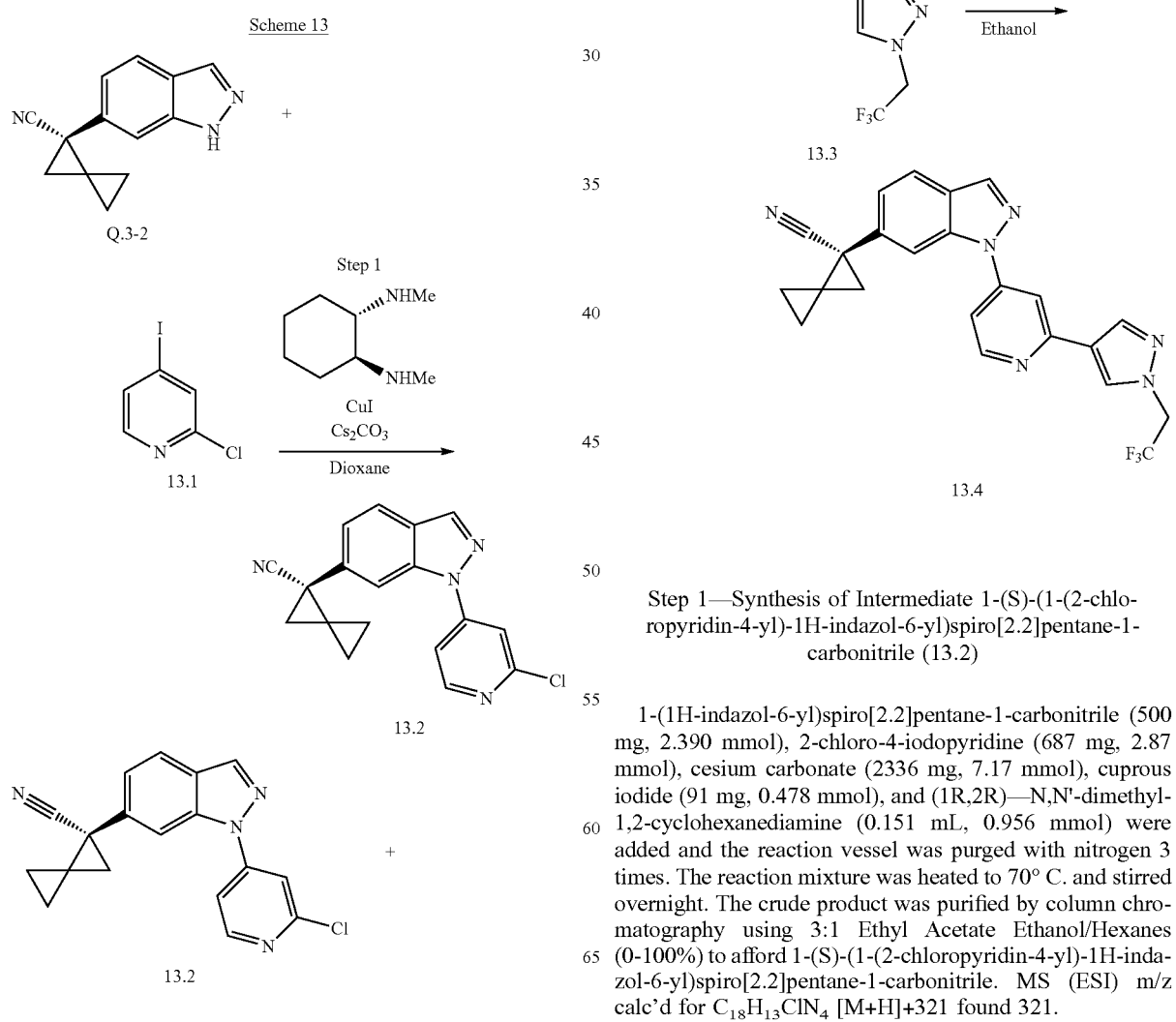

Step 1—Synthesis of Intermediate 1-(S)-(1-(2-chloropyridin-4-yl)-1H-indazol-6-yl)spiro[2.2]pentane-1-carbonitrile (13.2)

1-(1H-indazol-6-yl)spiro[2.2]pentane-1-carbonitrile (500 mg, 2.390 mmol), 2-chloro-4-iodopyridine (687 mg, 2.87 mmol), cesium carbonate (2336 mg, 7.17 mmol), cuprous iodide (91 mg, 0.478 mmol), and (1R,2R)—N,N'-dimethyl-1,2-cyclohexanediamine (0.151 mL, 0.956 mmol) were added and the reaction vessel was purged with nitrogen 3 times. The reaction mixture was heated to 70° C. and stirred overnight. The crude product was purified by column chromatography using 3:1 Ethyl Acetate Ethanol/Hexanes (0-100%) to afford 1-(S)-(1-(2-chloropyridin-4-yl)-1H-indazol-6-yl)spiro[2.2]pentane-1-carbonitrile. MS (ESI) m/z calc'd for $C_{18}H_{13}ClN_4$ [M+H]+321 found 321.

Step 2—Synthesis of Example 1-(S)-(1-(2-(1-(2,2,2-trifluoroethyl)-1H-pyrazol-4-yl)pyridin-4-yl)-1H-indazol-6-yl)spiro[2.2]pentane-1-carbonitrile (13.4)

1-(S)-(1-(2-chloropyridin-4-yl)-1H-indazol-6-yl)spiro[2.2]pentane-1-carbonitrile (32.1 mg, 0.1 mmol), 4-(4,4,5,5-tetramethyl-1,3,2-dioxaborolan-2-yl)-1-(2,2,2-trifluoroethyl)-1H-pyrazole (41.4 mg, 0.150 mmol), Si-DPP-Pd (80 mg, 0.020 mmol), potassium carbonate (100 µl, 0.200 mmol), and ethanol (1000 µl) were added to a microwave vial. The contents of the vial were microwaved at 120° C. for 20 minutes. The reaction mixture was filtered and the resulting material was further purified via reverse phase prep-HPLC [method A]. This provided 1-(S)-(1-(2-(1-(2,2,2-trifluoroethyl)-1H-pyrazol-4-yl)pyridin-4-yl)-1H-indazol-6-yl)spiro[2.2]pentane-1-carbonitrile, TFA (13.4). MS (ESI) m/z calc'd for $C_{23}H_{17}F_3N_6$ [M+H]+435 found 435. 1H NMR (499 MHz, DMSO-d6) δ 8.74 (d, J=5.7 Hz, 1H), 8.62 (s, 1H), 8.58 (s, 1H), 8.34 (s, 1H), 8.24 (d, J=1.8 Hz, 1H), 8.00 (d, J=8.4 Hz, 1H), 7.94 (s, 1H), 7.79 (dd, J=5.7, 2.0 Hz, 1H), 7.32 (dd, J=8.4, 1.4 Hz, 1H), 5.26 (q, J=9.0 Hz, 2H), 2.37 (d, J=5.2 Hz, 1H), 2.21 (d, J=5.2 Hz, 1H), 1.31-1.20 (m, 3H), 1.14-1.08 (m, 1H).

Reverse Phase Prep-HPLC Methods:
Method A-TFA Modifier
Reverse-phase Prep-HPLC [Waters SunFire OBD C18, 19 mm×150 mm (5 µm); gradient elution, MeCN/H₂O/0.1% TFA). Electrospray (ESI) Mass-triggered fraction collected was employed using positive ion polarity scanning to monitor for the target mass.
HPLC Gradient:

| Time (min) | % Acetonitrile | Mobile Phase Flowrate (mL/min) | Modifier Flowrate (mL/min) |
| --- | --- | --- | --- |
| 0.0 | 2 | 25 | 0.25 |
| 3.0 | 2 | 35 | 0.35 |
| 33.0 | 95 | 35 | 0.35 |
| 33.1 | 100 | 40 | 0.4 |
| 36.1 | 100 | 50 | 0.5 |
| 36.8/end | 2 | 25 | 0.2 |

Method B—NH₄OH Modifier
reverse-phase Prep-HPLC [Waters XBridge OBD C18, 19 mm×150 mm (5 µm); gradient elution, MeCN/H₂O/0.1% NH₄OH). Electrospray (ESI) Mass-triggered fraction collected was employed using positive ion polarity scanning to monitor for the target mass

| Time (min) | % Acetonitrile | Mobile Phase Flowrate (mL/min) | Modifier Flowrate (mL/min) |
| --- | --- | --- | --- |
| 0.0 | 2 | 25 | 0.25 |
| 3.0 | 2 | 35 | 0.35 |
| 33.0 | 95 | 35 | 0.35 |
| 33.1 | 100 | 40 | 0.4 |
| 36.1 | 100 | 50 | 0.5 |
| 36.8/end | 2 | 25 | 0.2 |

The compounds of the invention, surprisingly and advantageously, exhibit exceptional potency as inhibitors of LRRK2 kinase. The $IC_{50}$ values reported herein were measured as follows.

Biological Assay: LRRK2 Km ATP LanthaScreen™ Assay

The LRRK2 kinase activity reported herein as IC50 values was determined with LanthaScreen™ technology from Life Technologies Corporation (Carlsbad, Calif.) using GST-tagged truncated human mutant G2019S LRRK2 in the presence of the fluorescein-labeled peptide substrate LRRKtide, also from Life Technologies. The data presented for the Km ATP LanthaScreen™ Assay represents mean $IC_{50}$ values based on several test results and may have reasonable deviations depending on the specific conditions and reagents used. Assays were performed in the presence of 134 µM ATP (Km ATP). Upon completion, the assay was stopped and phosphorylated substrate detected with a terbium (Tb)-labeled anti-pERM antibody (cat. no. PV4898). The compound dose response was prepared by diluting a 10 mM stock of compound to a maximum concentration of 9.99 M in 100% dimethylsulfoxide followed by custom fold serial dilution in dimethylsulfoxide nine times. Twenty nanoliters of each dilution was spotted via a Labcyte Echo onto a 384-well black-sided plate (Corning 3575) followed by 15 µl of a 1.25 nM enzyme solution in 1× assay buffer (50 mM Tris pH 8.5, 10 mM MgCl2, 0.01% Brij-35, 1 mM EGTA, 2 mM dithiothreitol, 0.05 mM sodium orthovanadate). Following a 15-minute incubation at room temperature, the kinase reaction was started with the addition of 5 µl of 400 nM fluorescein-labeled LRRKtide peptide substrate and 134 µM ATP solution in 1× assay buffer. The reaction was allowed to progress at ambient temperature for 90 minutes. The reaction was then stopped by the addition of 20 µl of TR-FRET Dilution Buffer (Life Technologies, Carlsbad, Calif.) containing 2 nM Tb-labeled anti-phospho LRRKtide antibody and 10 mM EDTA (Life Technologies, Carlsbad, Calif.). After an incubation of 1 hour at room temperature, the plate was read on an EnVision multimode plate reader (Perkin Elmer, Waltham, Mass.) with an excitation wavelength of 337 nm (Laser) and a reading emission at both 520 and 495 nm. Compound IC50s were interpolated from nonlinear regression best fits of the log of the final compound concentration, plotted as a function of the 520/495-nm emission ratio using Activity base. Abase uses a 4 parameter (4P) logistic fit based on the Levenberg-Marquardt algorithm.

While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. For example, effective dosages other than the particular dosages as set forth herein above may be applicable as a consequence of variations in the responsiveness of the mammal being treated for any of the indications with the compounds of the invention indicated above. Likewise, the specific pharmacological responses observed may vary according to and depending upon the particular active compounds selected or whether there are present pharmaceutical carriers, as well as the type of formulation and mode of administration employed, and such expected variations or differences in the results are contemplated in accordance with the objects and practices of the present invention. It is intended, therefore, that the invention be defined by the scope of the claims which follow and that such claims be interpreted as broadly as is reasonable.

What is claimed:

1. A compound having a structural Formula (I):

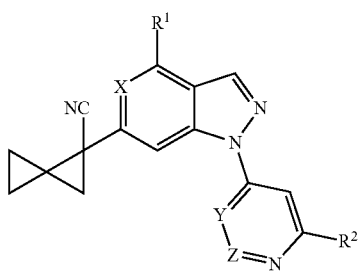

or a pharmaceutically acceptable salt thereof, wherein:
$R^1$ is H or F;
X is $C(R^x)$ or N;
$R^x$ is H, F, Cl, or —($C_1$-$C_6$)alkyl;
=Y—Z= is =N—C($R^Z$)=, =C(H)—C($R^Z$)=, or =C(H)—N=;
$R^z$ is H, F, —($C_1$-$C_6$)alkyl, —$NH_2$, —NH($C_1$-$C_6$)alkyl, —N((C-$C_6$)alkyl)$_2$, —O($C_1$-$C_6$)alkyl, —S($C_1$-

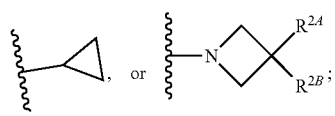

$C_6$)alkyl, —($C_1$-$C_6$)alkyl-OH, —($C_1$-$C_6$)alkyl—O—($C_1$-$C_6$)alkyl,

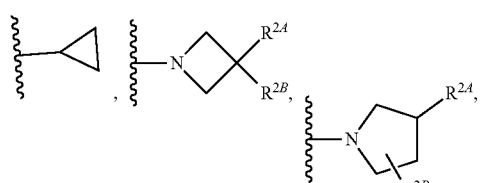

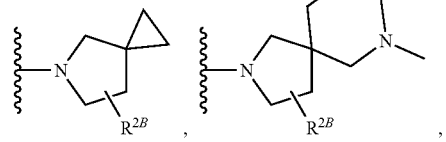

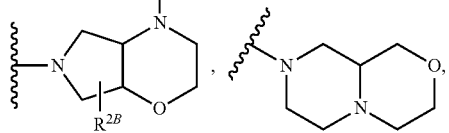

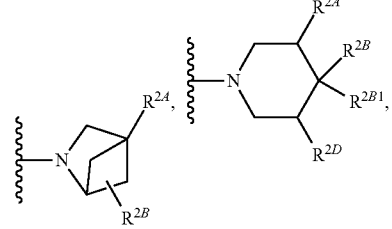

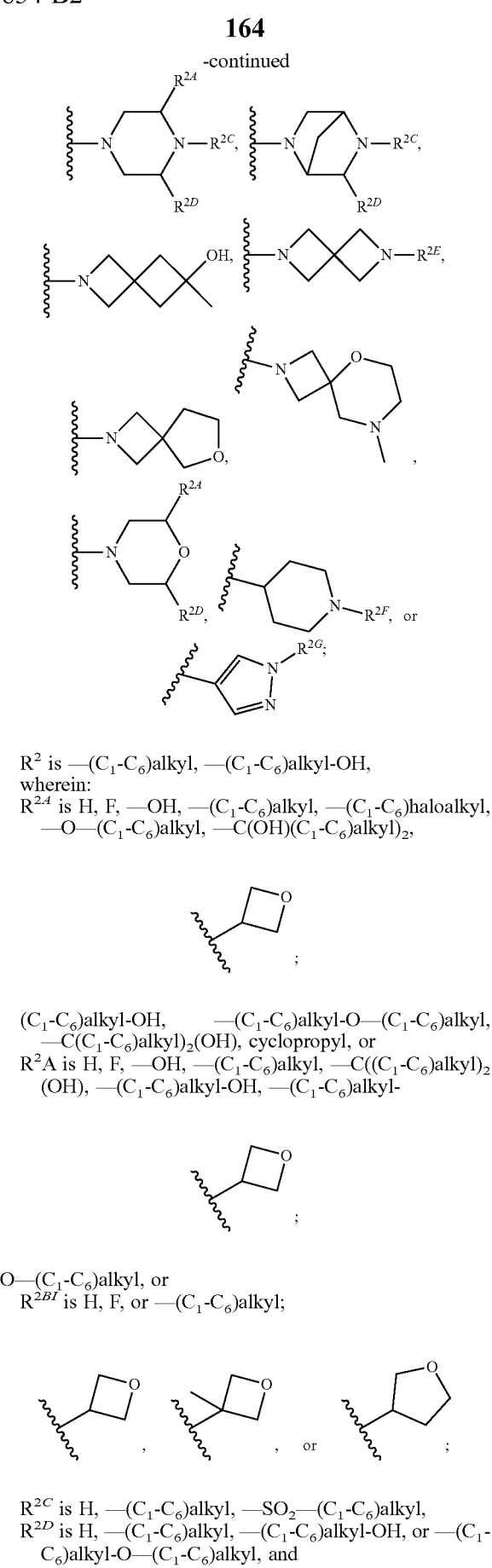

$R^2$ is —($C_1$-$C_6$)alkyl, —($C_1$-$C_6$)alkyl-OH,
wherein:
$R^{2A}$ is H, F, —OH, —($C_1$-$C_6$)alkyl, —($C_1$-$C_6$)haloalkyl, —O—($C_1$-$C_6$)alkyl, —C(OH)($C_1$-$C_6$)alkyl)$_2$, ($C_1$-$C_6$)alkyl-OH, —($C_1$-$C_6$)alkyl—O—($C_1$-$C_6$)alkyl, —C(($C_1$-$C_6$)alkyl)$_2$(OH), cyclopropyl, or
$R^{2}A$ is H, F, —OH, —($C_1$-$C_6$)alkyl, —C(($C_1$-$C_6$)alkyl)$_2$(OH), —($C_1$-$C_6$)alkyl-OH, —($C_1$-$C_6$)alkyl- O—($C_1$-$C_6$)alkyl, or
$R^{2BI}$ is H, F, or —($C_1$-$C_6$)alkyl;

$R^{2C}$ is H, —($C_1$-$C_6$)alkyl, —$SO_2$—($C_1$-$C_6$)alkyl,
$R^{2D}$ is H, —($C_1$-$C_6$)alkyl, —($C_1$-$C_6$)alkyl-OH, or —($C_1$-$C_6$)alkyl-O—($C_1$-$C_6$)alkyl, and

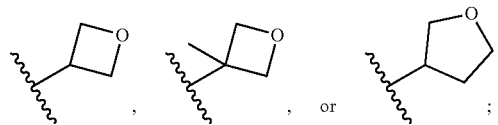

$R^{2E}$ is H, —($C_1$-$C_6$)alkyl, —($C_1$-$C_6$)haloalkyl,

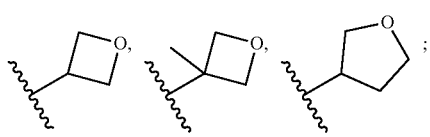

$R^{2F}$ is H, —($C_1$-$C_6$)alkyl, —($C_1$-$C_6$)fluoroalkyl, —($C_1$-$C_6$)alkyl-O—($C_1$-$C_6$)alkyl, and $R^{2G}$ is H, —($C_1$-$C_6$)alkyl, or —($C_1$-$C_6$)haloalkyl.

2. The compound of claim 1, or a pharmaceutically acceptable salt thereof, wherein X is C($R^x$) and Formula has a structural Formula (IA):

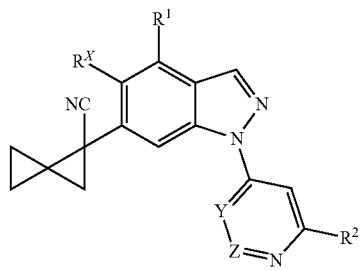

(IA)

wherein:

$R^X$ is H, F, Cl, or $CH_3$.

3. The compound of claim 1, or a pharmaceutically acceptable salt thereof, wherein X is N and Formula (I) has a structural Formula (IB):

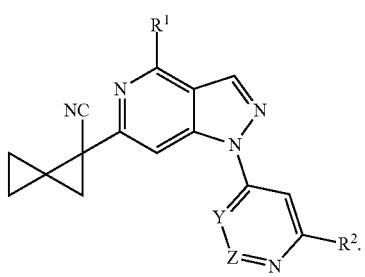

(IB)

4. The compound according to claim 1, or a pharmaceutically acceptable salt thereof, wherein:
=Y—Z= is =N—C($R^z$)=.

5. The compound according to claim 1, or a pharmaceutically acceptable salt thereof, wherein:
=Y—Z= is =C(H)—C($R^z$)=.

6. The compound according to claim 1, or a pharmaceutically acceptable salt thereof, wherein:
=Y—Z= is =C(H)—N=.

7. The compound of claim 1, or a pharmaceutically acceptable salt thereof, wherein said compound is selected from;

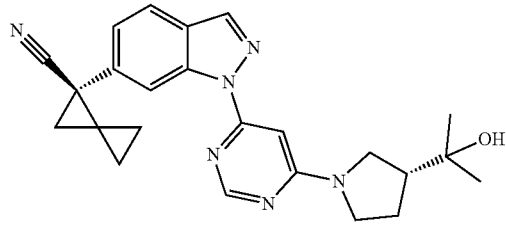

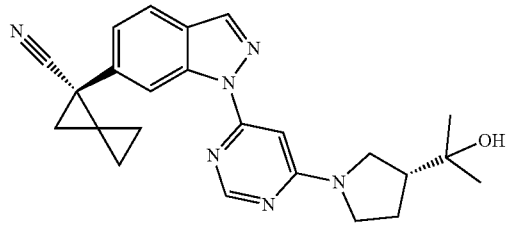

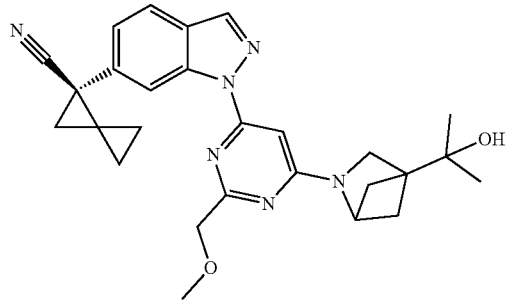

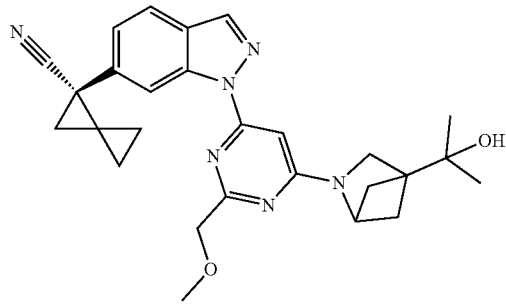

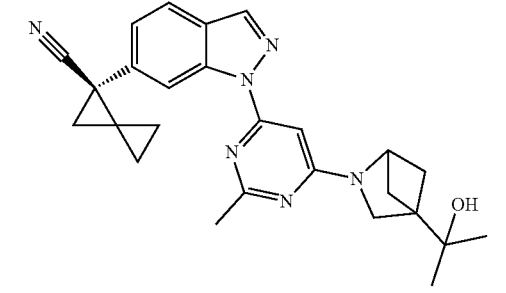

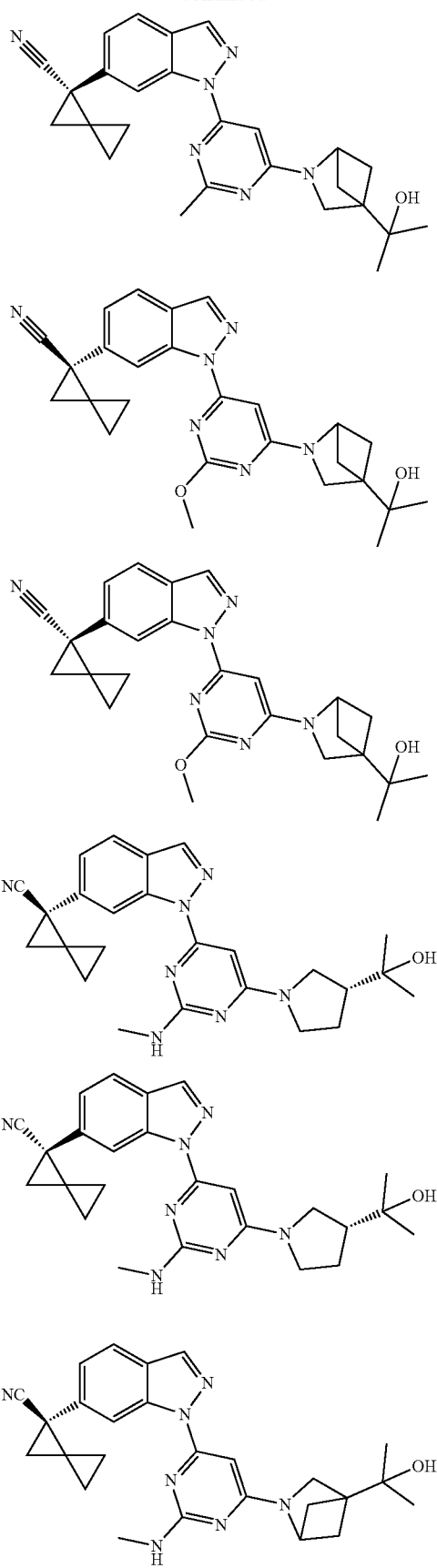
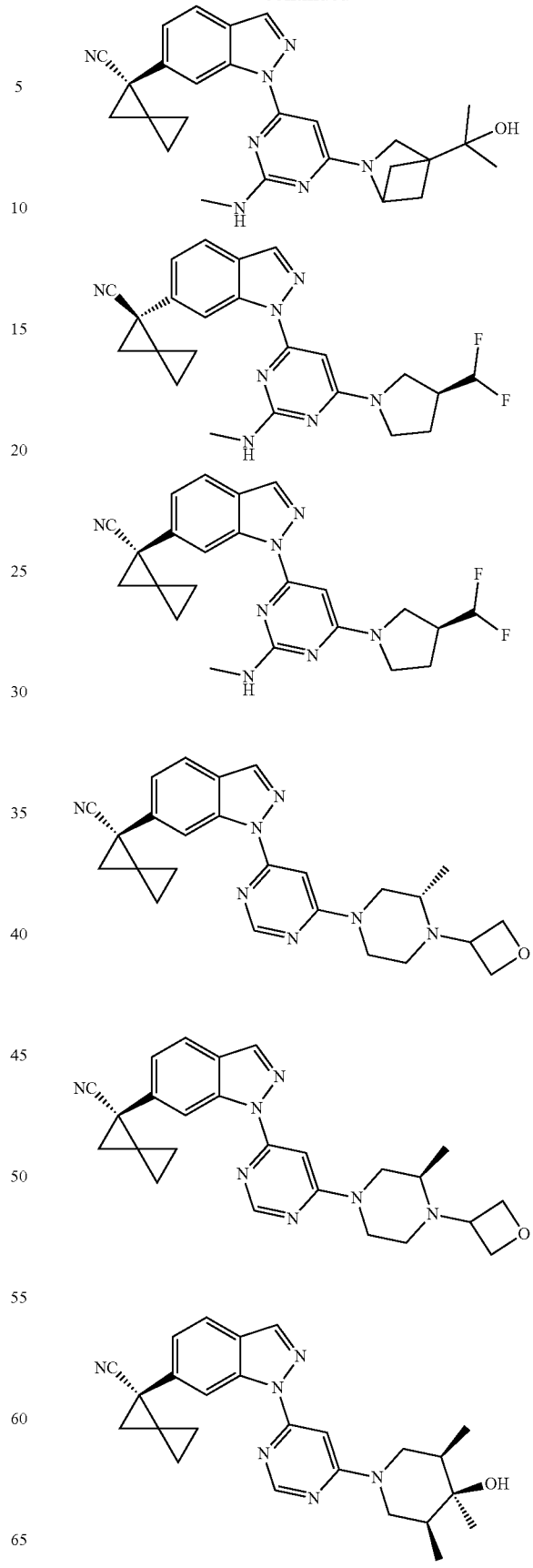

169
-continued
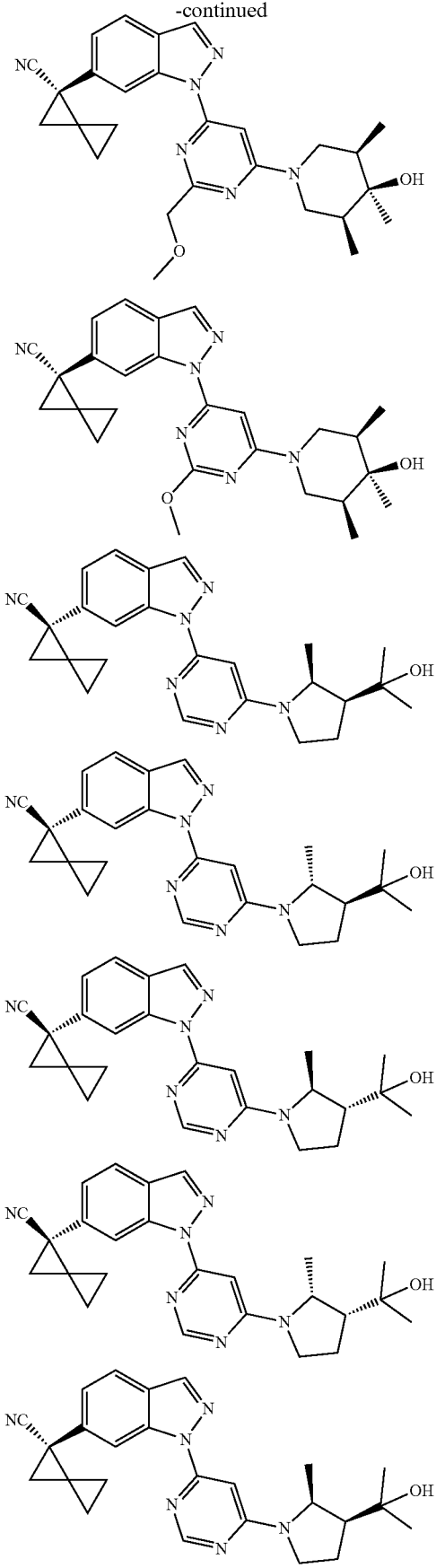
170
-continued
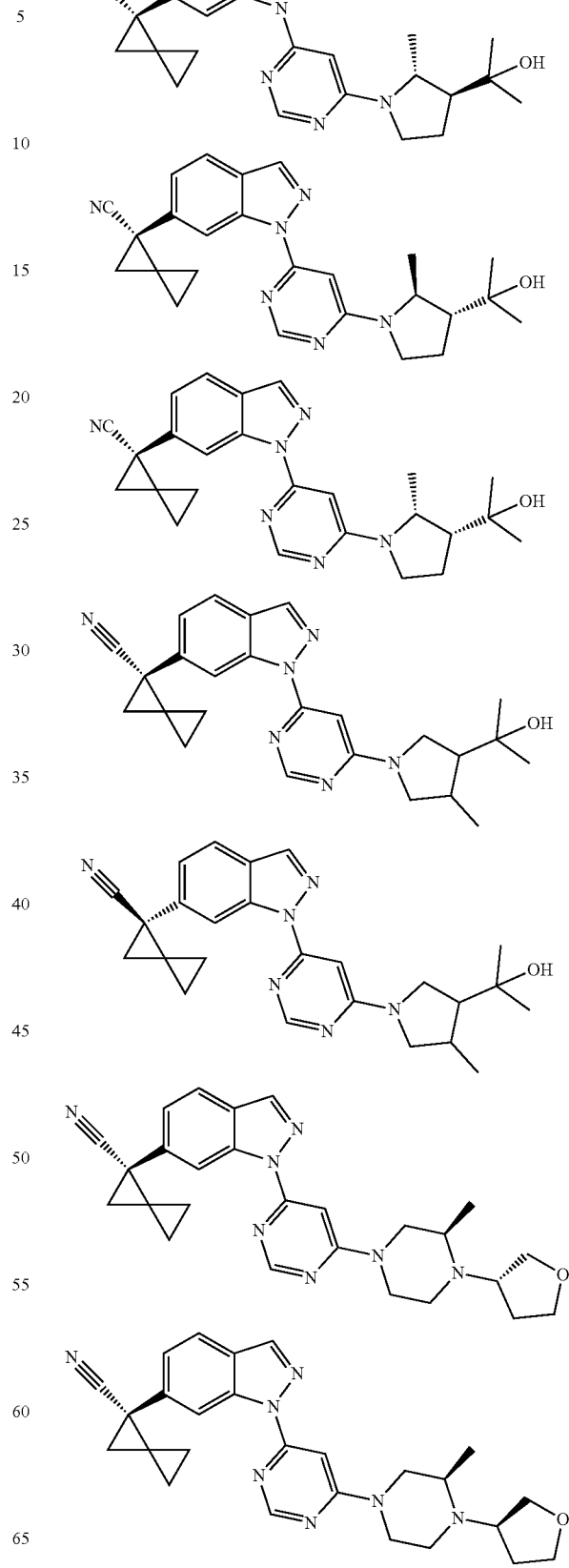

171
-continued
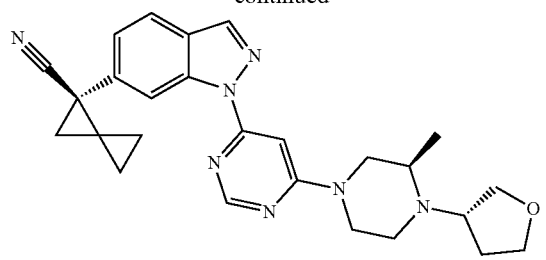
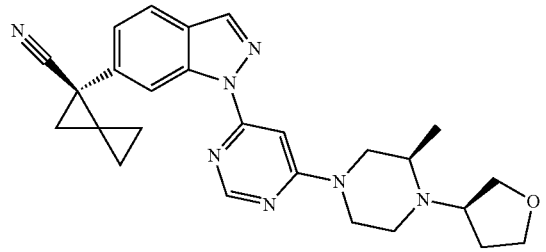
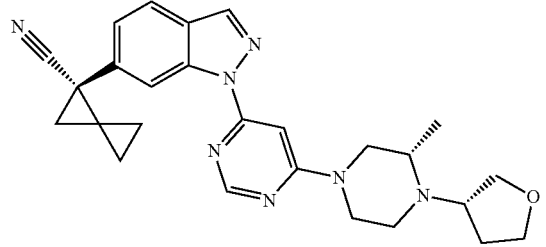
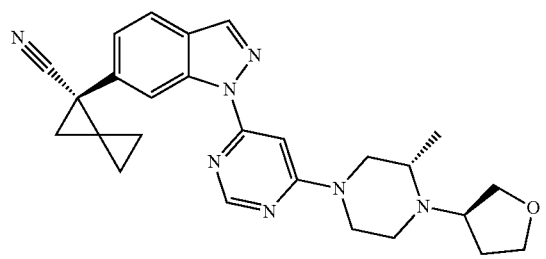
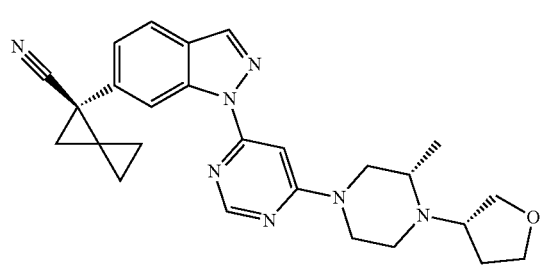
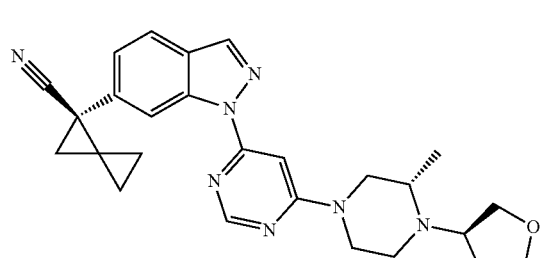
172
-continued
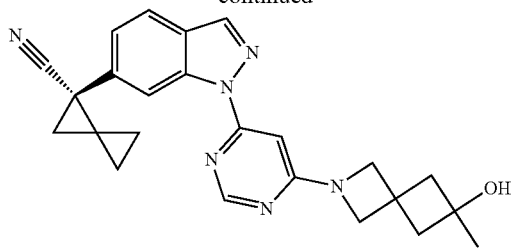
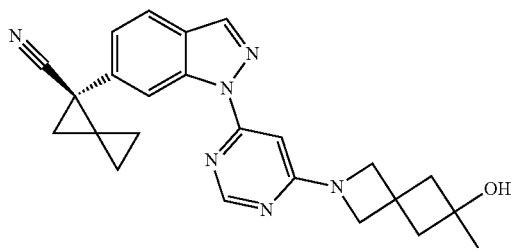
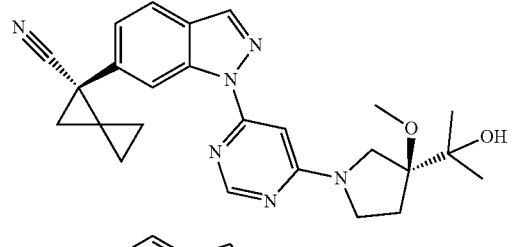
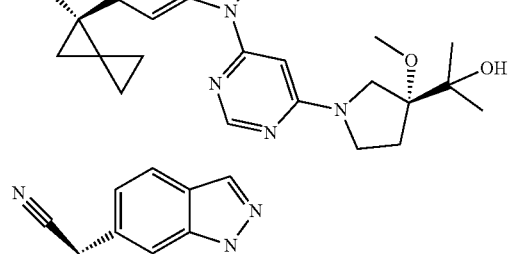
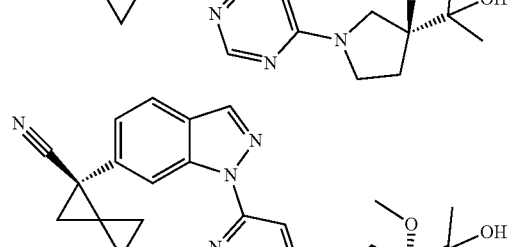
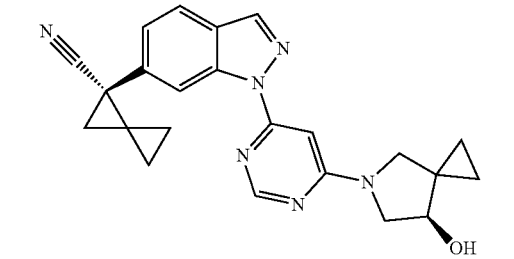

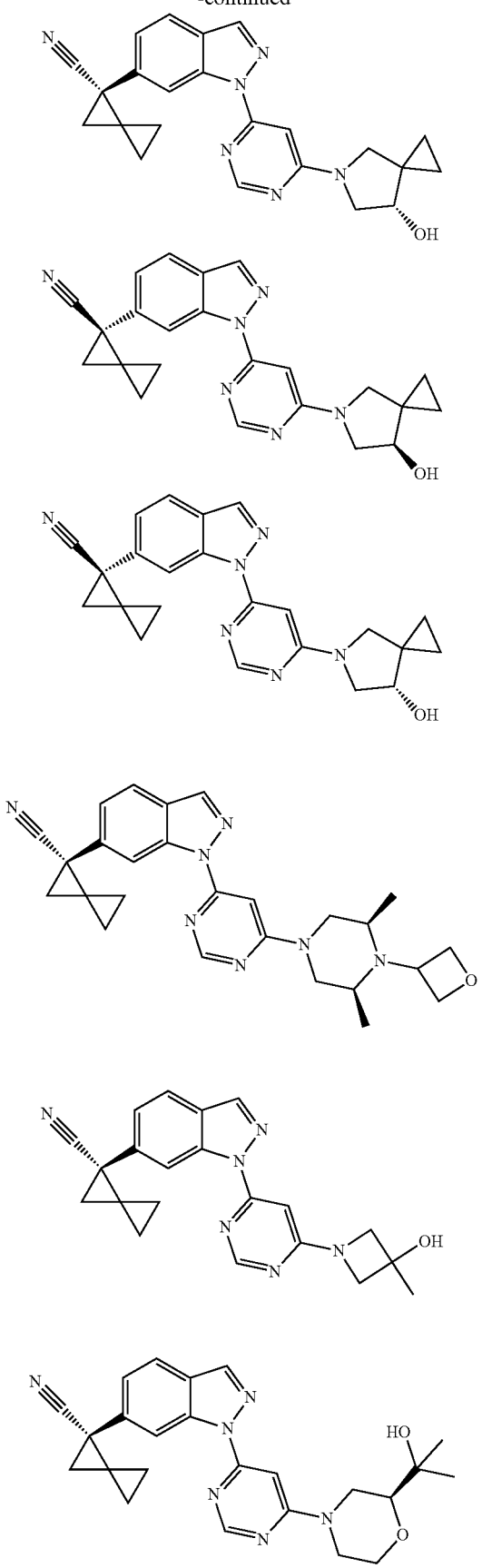
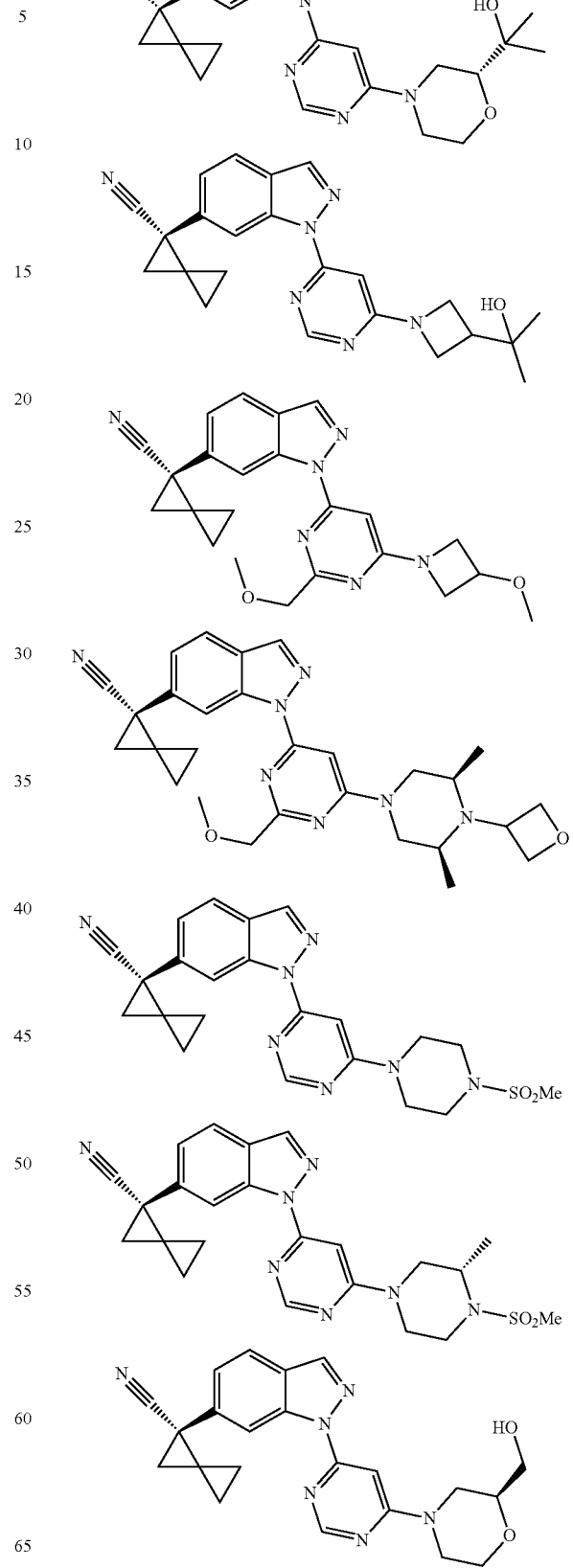

175
-continued
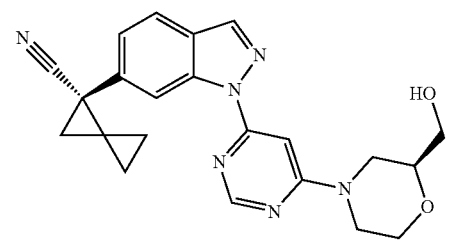
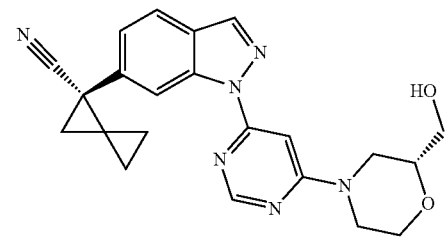
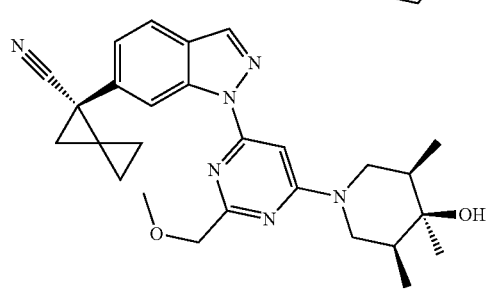
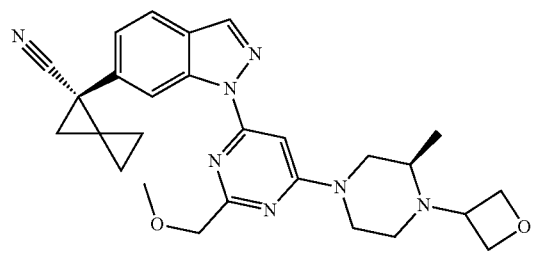
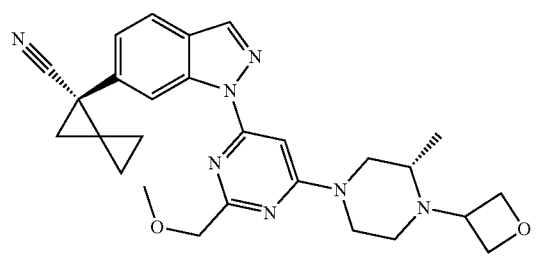
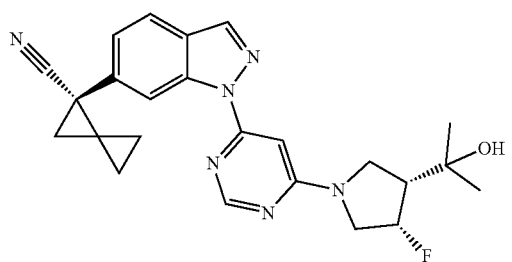
176
-continued
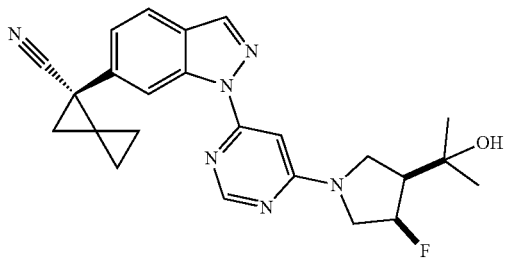
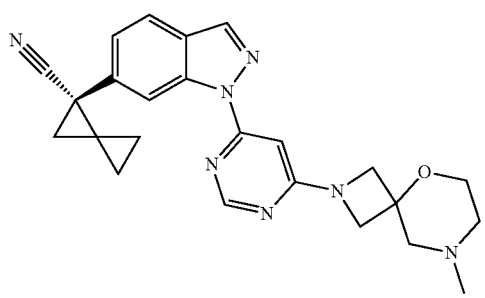
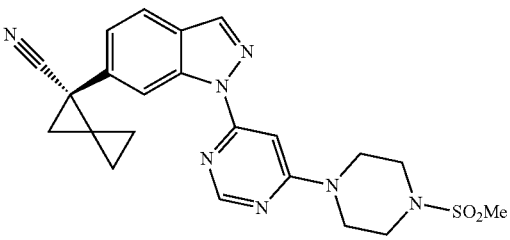
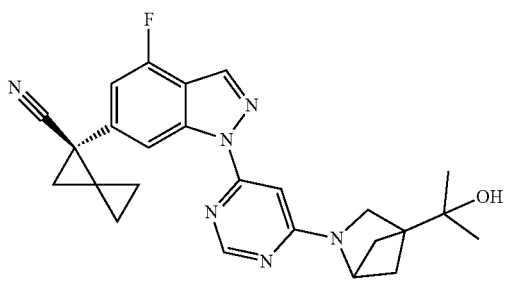
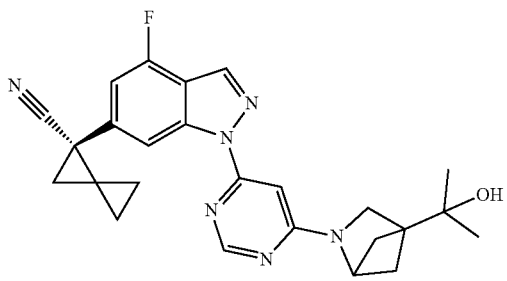
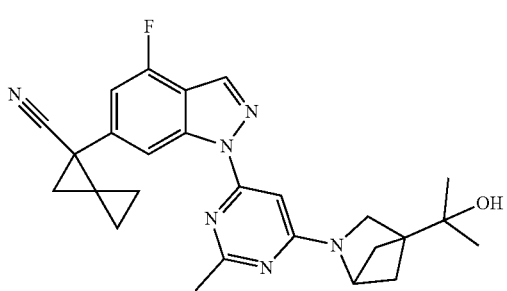

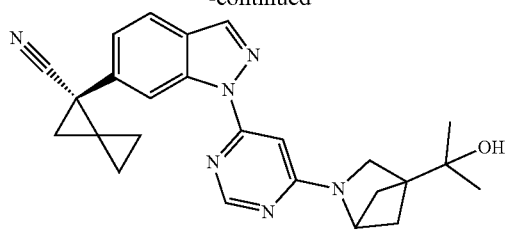
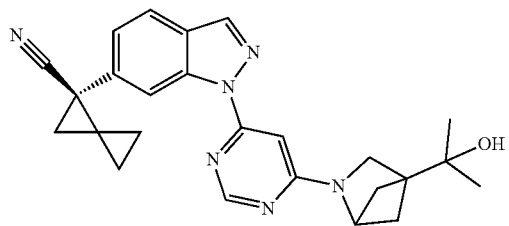
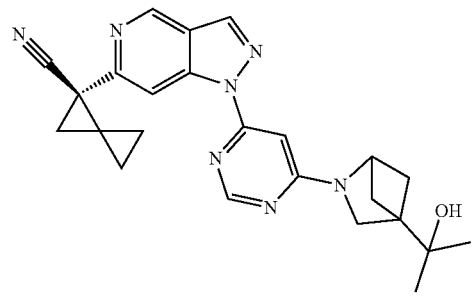
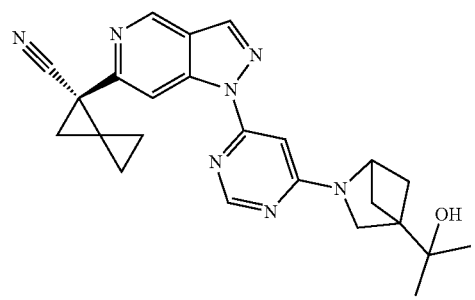
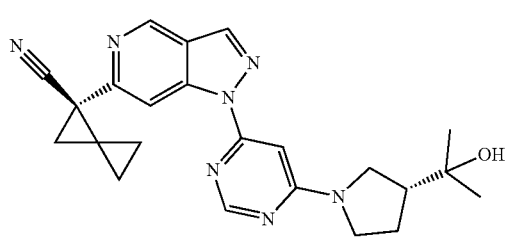
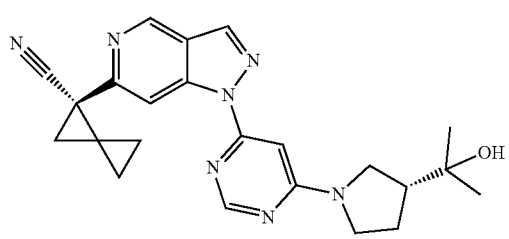
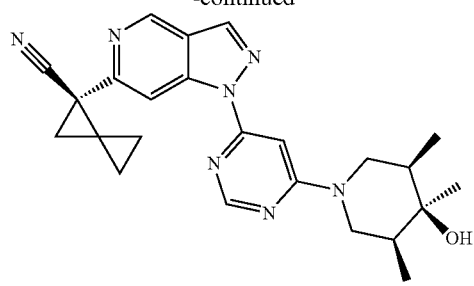
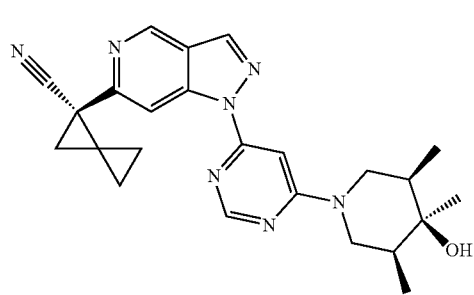
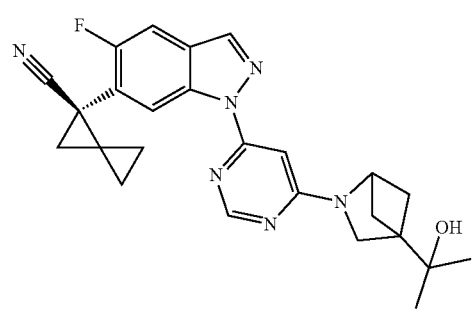
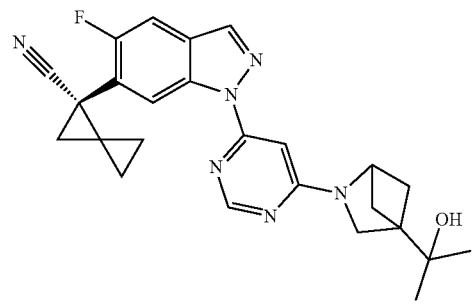
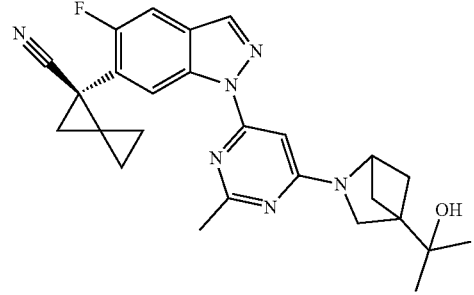

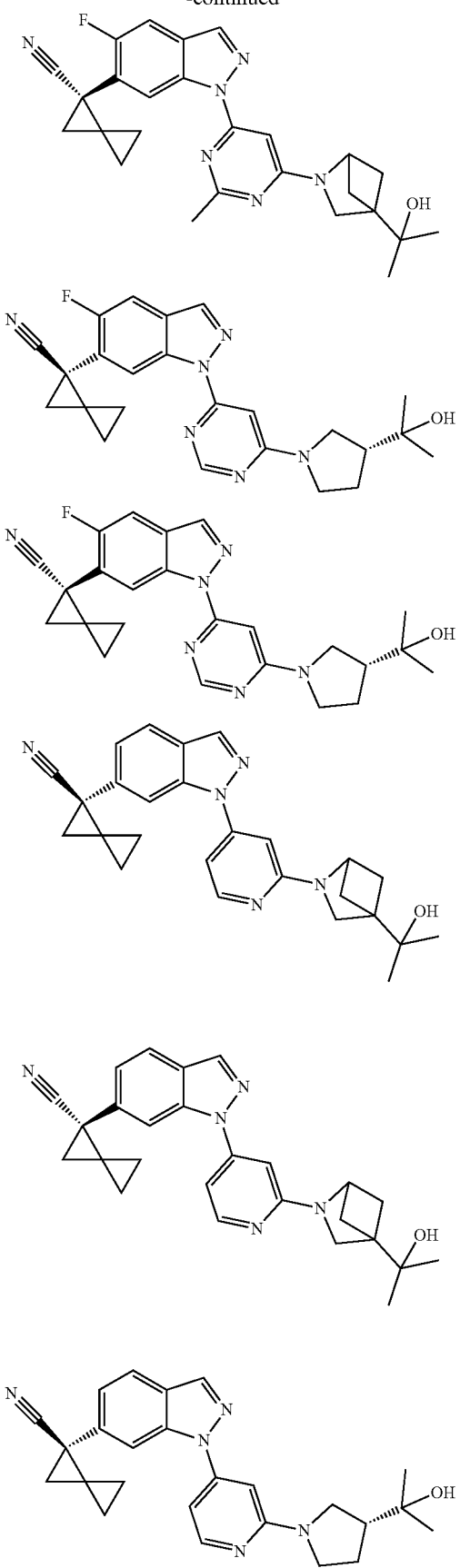
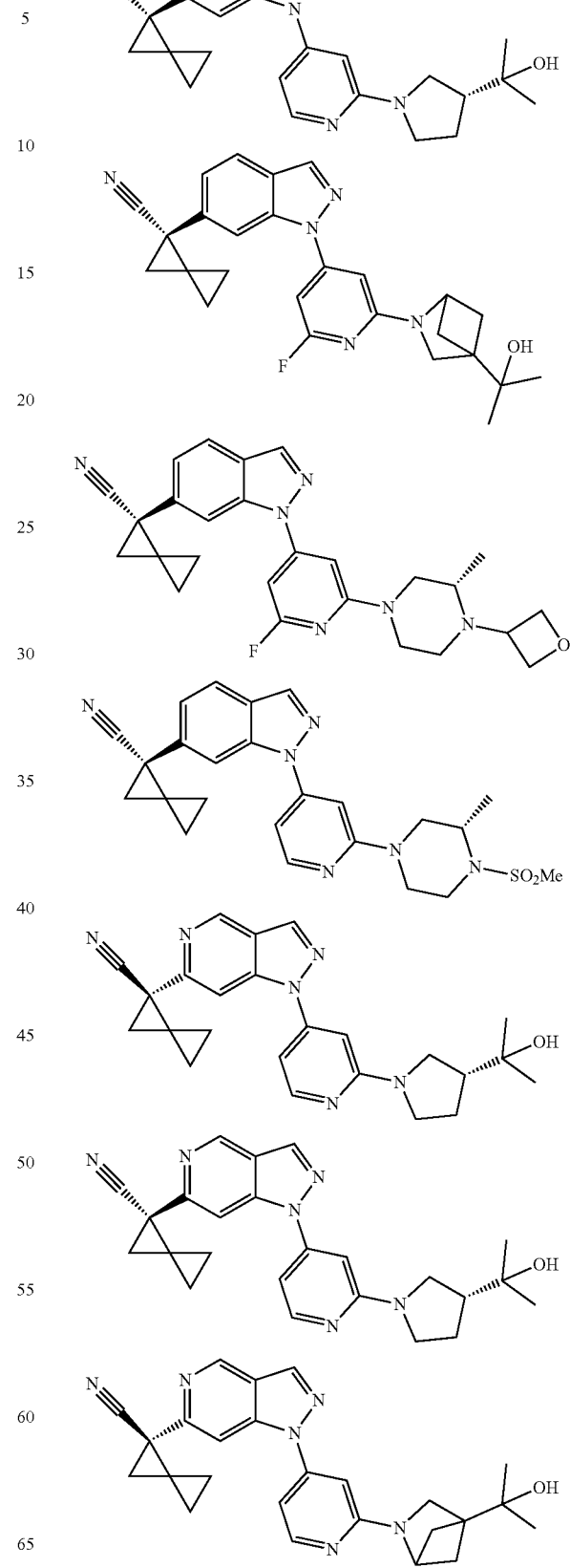

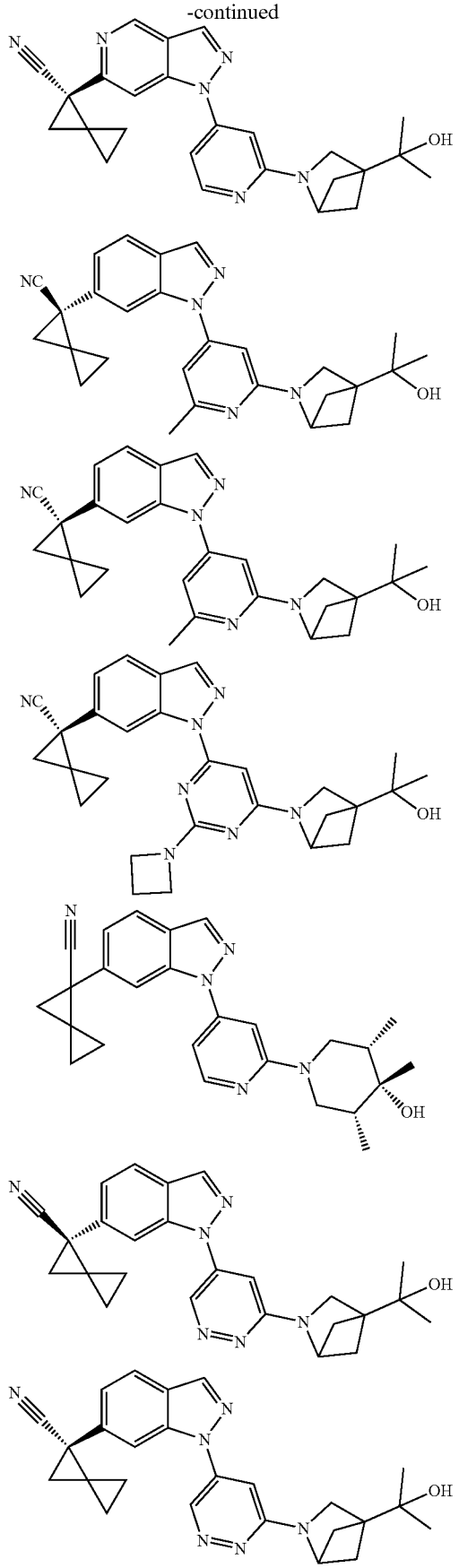
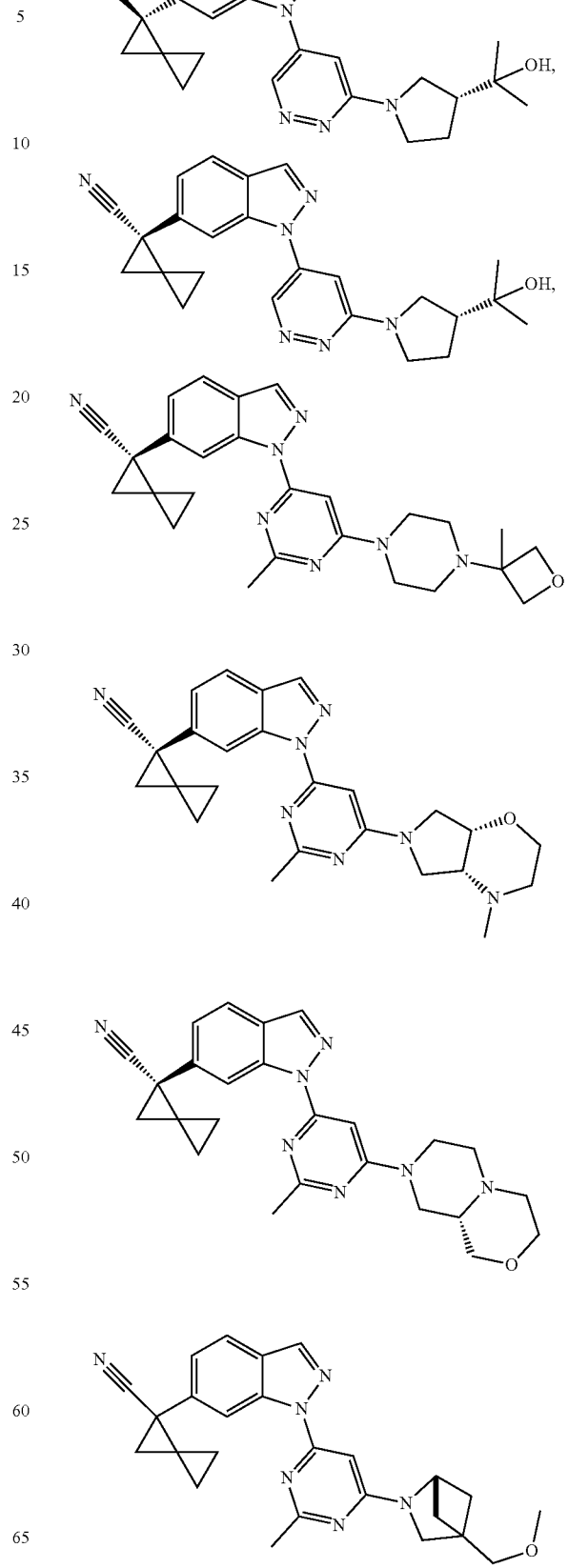

183
-continued
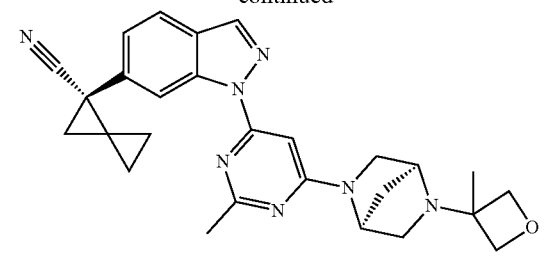
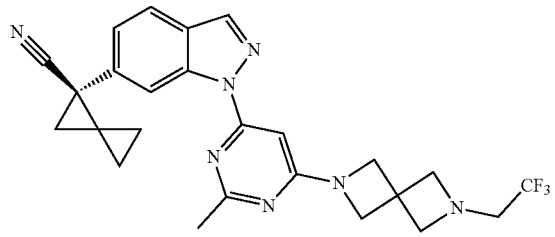
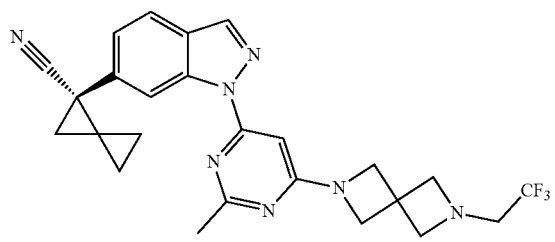
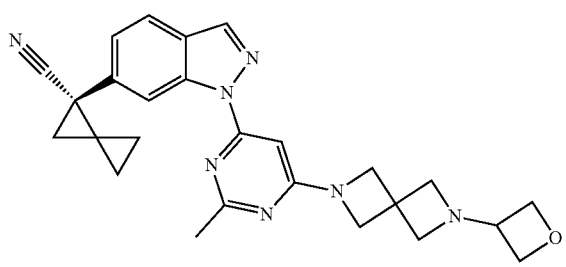
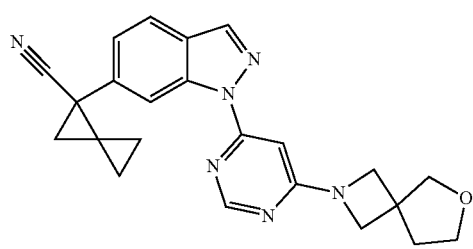
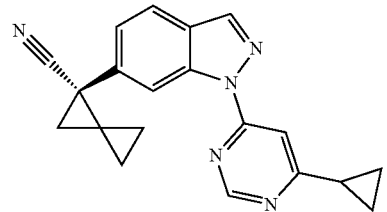
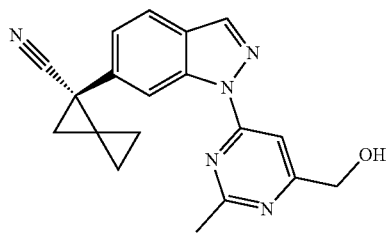
184
-continued
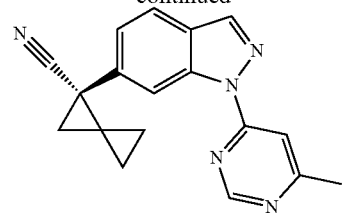
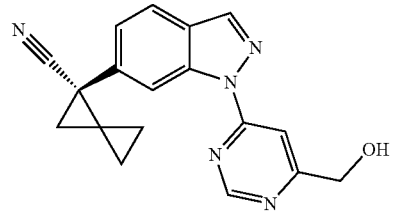
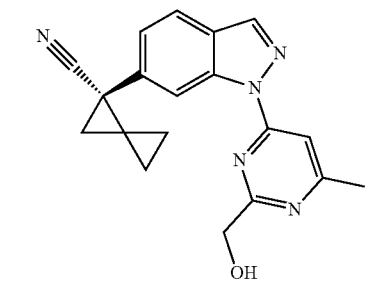
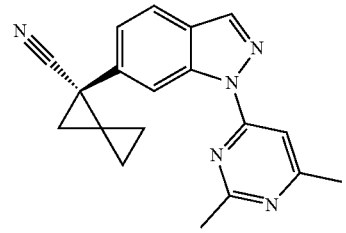
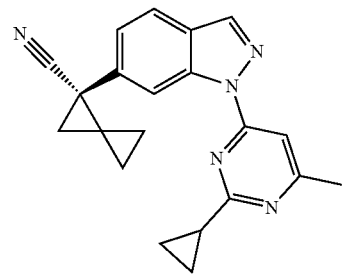
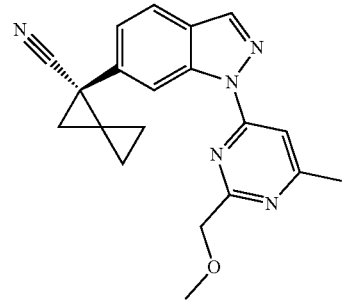

-continued

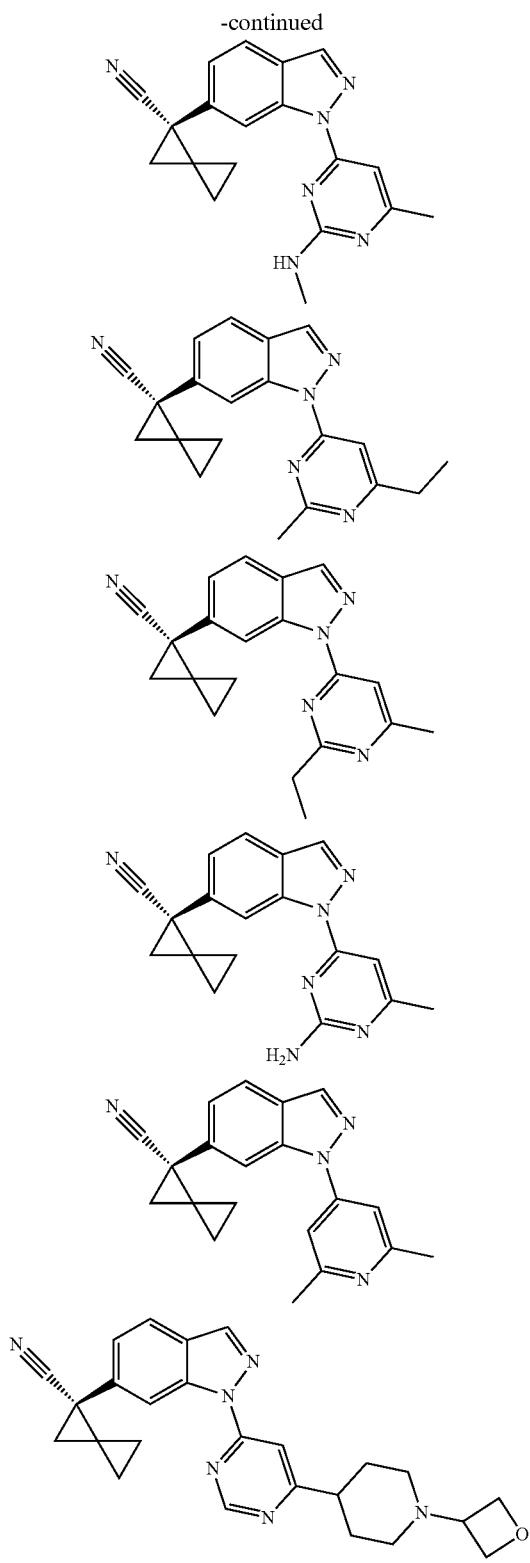

-continued

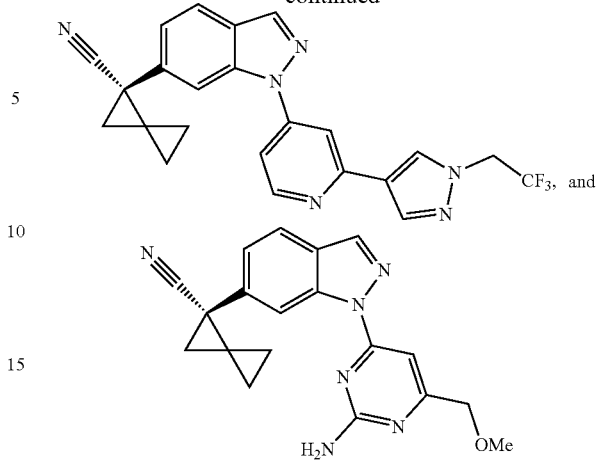

8. A pharmaceutical composition comprising a compound of claim 1, and pharmaceutically acceptable carrier.

9. A method of treating Parkinson's, Disease comprising administrating an effective amount of compound of claim 1, or a pharmaceutically acceptable salt thereof, to a person in need thereof.

10. A method for the treatment of an indication in which LRRK2 kinase is involved comprising administering a subject in need thereof an effective amount of a compound according to claim 1, or pharmaceutically acceptable salt thereof, said indication selected from:

abnormal motor symptoms associated with Parkinson's disease, non-motor symptoms associated with Parkinson's disease, Lewy body dementia, L-Dopa induced dyskinesias, Alzheimer's disease, mild cognitive impairment, the transition from mild cognitive impairment to Alzheimer's disease, tanopathy disorders characterized by hyperphosphorylation of tau such as argyrophilic grain disease, Picks disease, corticobasal degeneration, progressive supranuclear palsy, inherited frontotemporal dementia, and Parkinson's disease linked to chromosome 17, neuroinflammation associated with microglial inflammatory responses associated with multiple sclerosis, HIV-induced dementia, ALS, ischemic stroke, traumatic brain injury and spinal cord injury, lymphomas, leukemia, multiple sclerosis, rheumatoid arthritis, systemic lupus erythematosus, autoimmune hemolytic anemia, pure red cell aplasia, idiopathic thrombocytopenic pupura (ITP), Evans Syndrome, vasculitis bullous skin disorder, type I diabetes mellitus, Sjorgen's syndrome, Delvic's disease, inflammatory myopathies, and ankylosing spondylitis, renal cancer, breast cancer, lung cancer, prostate cancer, and acute myelogenous leukemia (AML) in subjects expressing the LRRK2 G2019S mutation, papillary renal and thyroid carcinomas in a subject in whom LRRK2 is amplified or overexpressed, Crohn's disease and leprosy.

\* \* \* \* \*